US008569054B2

(12) United States Patent
Goldenberg et al.

(10) Patent No.: US 8,569,054 B2
(45) Date of Patent: *Oct. 29, 2013

(54) MAMMALIAN CELL LINES FOR INCREASING LONGEVITY AND PROTEIN YIELD FROM A CELL CULTURE

(71) Applicant: Immunomedics, Inc., Morris Plains, NJ (US)

(72) Inventors: David M. Goldenberg, Mendham, NJ (US); Zhengxing Qu, Warren, NJ (US); Chien-Hsing Chang, Downington, PA (US); Edmund A. Rossi, Woodland Park, NJ (US); Jeng-Dar Yang, Bedminster, NJ (US); Diane Nordstrom, Rockaway, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/735,244

(22) Filed: Jan. 7, 2013

(65) Prior Publication Data

US 2013/0164783 A1 Jun. 27, 2013

Related U.S. Application Data

(60) Division of application No. 13/413,871, filed on Mar. 7, 2012, now Pat. No. 8,372,603, which is a division of application No. 13/287,395, filed on Nov. 2, 2011, now Pat. No. 8,153,433, which is a division of application No. 12/819,533, filed on Jun. 21, 2010, now Pat. No. 8,076,140, which is a division of application No. 12/405,733, filed on Mar. 17, 2009, now Pat. No. 7,785,880, which is a division of application No. 11/487,215, filed on Jul. 14, 2006, now Pat. No. 7,537,930, which is a continuation-in-part of application No. 11/187,863, filed on Jul. 25, 2005, now Pat. No. 7,531,327.

(60) Provisional application No. 60/590,349, filed on Jul. 23, 2004.

(51) Int. Cl.
*C12N 5/00* (2006.01)
*C12N 15/00* (2006.01)

(52) U.S. Cl.
USPC ............................ 435/325; 435/70.1; 435/455

(58) Field of Classification Search
None
See application file for complete search history.

(56) References Cited

U.S. PATENT DOCUMENTS

| 6,586,206 | B1 | 7/2003 | Dixit et al. |
|---|---|---|---|
| 6,635,448 | B2 | 10/2003 | Bucciarelli et al. |
| 6,635,802 | B1 | 10/2003 | Piedrahita et al. |
| 6,964,199 | B2 | 11/2005 | Lee et al. |
| 7,531,327 | B2 | 5/2009 | Goldenberg et al. |
| 7,537,930 | B2 | 5/2009 | Goldenberg et al. |
| 7,785,880 | B2 | 8/2010 | Goldenberg et al. |
| 8,076,140 | B2 | 12/2011 | Goldenberg et al. |
| 8,153,433 | B1 | 4/2012 | Goldenberg et al. |
| 2003/0064510 | A1 | 4/2003 | Reff et al. |
| 2003/0069201 | A1 | 4/2003 | Reed |
| 2003/0219871 | A1 | 11/2003 | Enenkel et al. |
| 2007/0092947 | A1 | 4/2007 | Goldenberg et al. |
| 2009/0111143 | A1 | 4/2009 | Goldenberg et al. |

FOREIGN PATENT DOCUMENTS

| WO | 00/73419 | 12/2000 |
|---|---|---|
| WO | 01/23592 | 4/2001 |
| WO | 01/66696 | 9/2001 |
| WO | 02/16590 | 2/2002 |
| WO | 02/40665 | 5/2002 |
| WO | 03/006607 | 1/2003 |
| WO | 03/040374 | 5/2003 |
| WO | 03/057866 | 7/2003 |
| WO | 03/083093 | 10/2003 |
| WO | 2005/065348 | 7/2005 |
| WO | 2007/015691 | 2/2007 |
| WO | 2007/015848 | 2/2007 |

OTHER PUBLICATIONS

Arden et al., "Cell engineering blocks stress and improves biotherapeutic production", Bioprocessing Journal, 3:23-28 (2004).
Arden et al., "Life and death in mammalian cell culture: strategies for apoptosis inhibition", Trends Biotechnol. 22 (4):174-80 (2004).
Brenner et al., "Increased p16 expression with first senescence arrest in human mammary epithelial cells and extended growth capacity with p16 inactivation", Oncogene 17:199-205 (1998).
Chang et al., "Effects of p21Waf1/Cip1/Sdi1 on cellular gene expression: Implications for carcinogenesis, senescence, and age-related diseases", Proc. Natl. Acad. Sci. USA 97, 4291-6, 2000.

(Continued)

*Primary Examiner* — Ilia Ouspenski

(74) *Attorney, Agent, or Firm* — Richard A. Nakashima

(57) ABSTRACT

Disclosed are compositions and methods for increasing the longevity of a cell culture and permitting the increased production of proteins, preferably recombinant proteins, such as antibodies, peptides, enzymes, growth factors, interleukins, interferons, hormones, and vaccines. Cells transfected with an apoptosis-inhibiting gene or vector, such as a triple mutant Bcl-2 gene, can survive longer in culture, resulting in extension of the state and yield of protein biosynthesis. Such transfected cells exhibit maximal cell densities that equal or exceed the maximal density achieved by the parent cell lines. Transfected cells can also be pre-adapted for growth in serum-free medium, greatly decreasing the time required to obtain protein production in serum-free medium. In certain methods, the pre-adapted cells can be used for protein production following transformation under serum-free conditions. The method preferably involves eukaryotic cells, more preferably mammalian cells.

17 Claims, 26 Drawing Sheets

(56) References Cited

OTHER PUBLICATIONS

Deng et al., "Mono- and multisite phosphorylation enhances Bcl2's antiapoptotic function and inhibition of cell cycle entry functions", PNAS (101) 153-158, 2004.

Deng et al., "Bcl2 retards G1/S cell cycle transition by regulating intracellular ROS", Blood, vol. 102, No. 9, pp. 3179-3185, 2003.

Finzer et al., "The role of human papillomavirus oncoproteins E6 and E7 in apoptosis", Cancer Lett 188, 15-24, 2002.

Fujita et al., "Overexpression of M-2 Improved Survival of COS-1 Cells and Enhanced Transient Protein Production", J. Ferment. Bioeng. 82(6):589-591 (1996).

Fujita et al., "Reinforcing apoptosisresistance of COS and myeloma cells by transfecting with bcl2 gene", Cytotechnology 25:25-33 (1997).

Geisse et al., "Eukaryotic expression systems: a comparison", Protein Expr. Purif. 8(3):271-82 (1996).

Ghezzi et al., "Erythropoietin as an antiapoptotic, tissue-protective cytokine", Cell Death Differ. 11 (Suppl. 1), s37-s44, Jul. 2004.

Gillies et al., "High-level expression of chimeric antibodies using adapted cDNA variable region cassettes", J. Immunol. Methods 125:191 (1989).

Goldstein and Singal "Senescence of Cultured Human Fibroblasts: Mitotic Versus Metabolic Time", Exp. Cell Res. 88, 359-64, 1974.

Jackson et al., "E6 proteins from diverse cutaneous HPV types inhibit apoptosis in response to UV damage", Oncogene 19(4):592-8 (2000).

Javelaud et al., "Induction of p21Waf1/Cip1 by TNFa requires NF-kB activity and antagonizes apoptosis in Ewing tumor cells", Oncogene 19, 61-8, 2000.

Lee et al., "Human papilloma virus type 16 E7 genes protect astrocytes against apoptotic and necrotic death induced by hydrogen peroxide", Yonsei Med. J. 42, 471-9, 2001.

Lee et al.' "Development of Apoptosis-Resistant Dihydrofolate Reductase-Deficient Chinese Hamster Ovary Cell Line", Biotechnology & Bioengineering 82:872-76, 2003.

Lotem et al., "Regulation by bcl-2, c-myc, and p53 of Susceptibility to Induction of Apoptosis by Heat Shock and Cancer Chemotherapy Compounds in Differentiation-competent and -defective Myeloid Leukemic Cells", Cell Growth & Differentiation, 4:41-47 (1993).

Mercille et al., "Apoptosis-Resistant E1B-19K-Expressing NS/0 Myeloma Cells Exhibit Increased Viability and Chimeric Antibody Productivity under Perfusion Culture Conditions", Biotechnol. Bioeng. 63:529-543 (1999).

Petros et al., "Structural biology of the Bcl-2 family of proteins", Biochim. Biophys. Acta. 1644(2-3):83-94 (2004).

Romanos et al., "Production of a phosphorylated GST:HPV-6 E7 fusion protein using a yeast expression vector and glutathione S-transferase fusions", Gene, vol. 152, No. 1, pp. 137-138, 1995.

Rossi et al., "A new mammalian host cell with enhanced survival enables completely serum-free development of high-level protein production cell lines", Biotechnol Prog. May 2011;27(3):766-75.

Schwartz et al., "In vitro Meylopoiesis Stimulated by Rapid Medium Exchange and Supplementation with Hematopoietic Growth Factors", Blood 78(12):3155-61, 1991 (Abstract only).

Storey et al., "Papillomaviruses: death-defying acts in skin cancer", Trends Mol. Med. 8(9):417-21 (2002).

Suzuki et al., "Establishing Apoptosis Resistant Cell Lines for Improving Protein Productivity of Cell Culture" Cytotechnology 23:55-59, 1997.

Tey et al., "Bcl-2 mediated suppression of apoptosis in myeloma NS0 cultures", J. Biotechnol. 79(2):147-59 (2000).

Tey et al., "Influence of Bcl-2 on cell death during cultivation of a Chinese Hamster Ovary cell line expressing a chimeric antibody", Biotechnol. Bioeng. 68: 31-43, 2000.

Vaux et al., "Bcl-2 gene promotes haemopoietic cell survival and cooperates with c-myc to immortalize pre-B cells", Nature 335, 440-2, 1988.

Yang et al., "Inhibitors Directed towards Caspase-1 and -3 Are Less Effective than Pan Caspase Inhibition in Preventing Renal Proximal Tubular Cell Apoptosis", Nephron Exp. Nephrol. 2004;96:e39-e51.

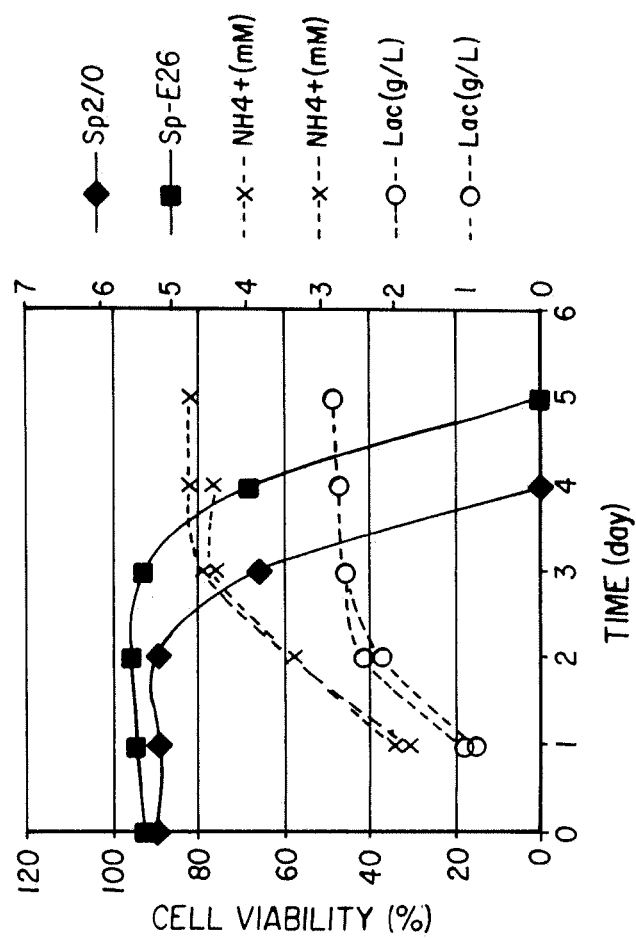
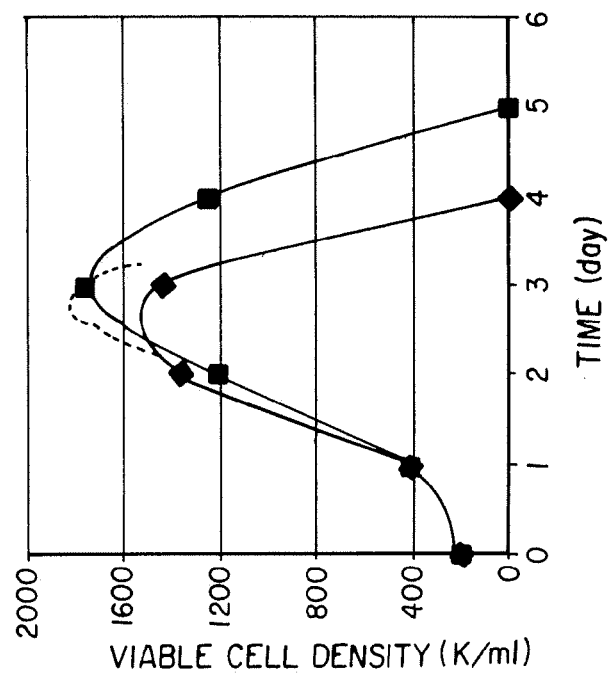
FIG. 5

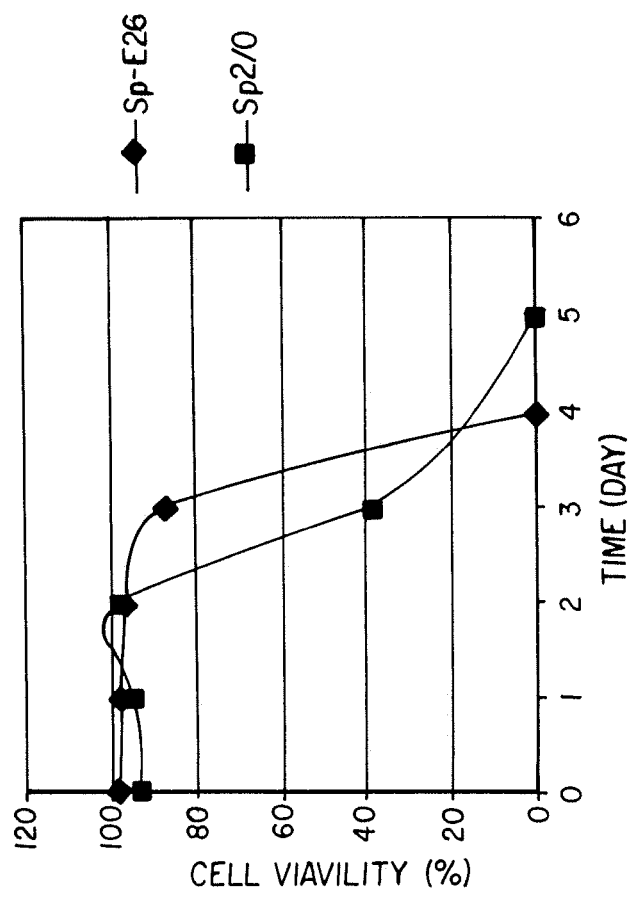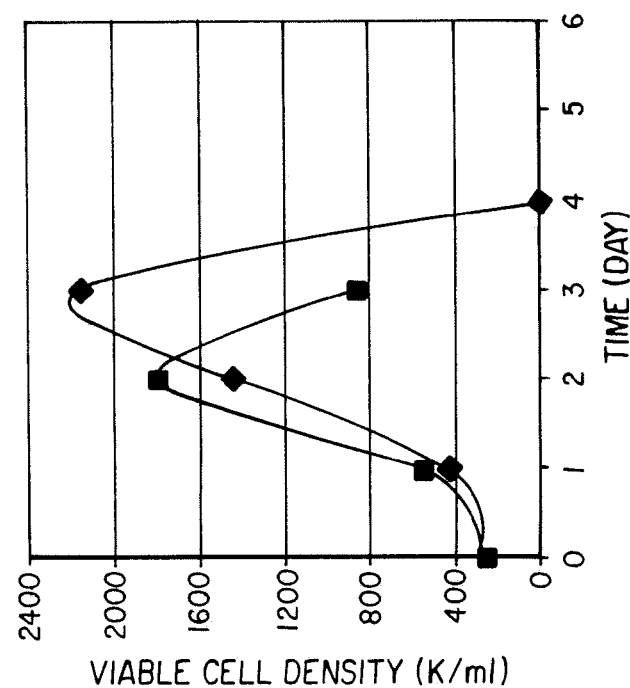
FIG. 6

FIG. 22 Western Blot bcl-2, β-Actin

MAMMALIAN CELL LINES FOR INCREASING LONGEVITY AND PROTEIN YIELD FROM A CELL CULTURE

RELATED APPLICATIONS

The present application is a divisional of U.S. patent application Ser. No. 13/413,871, filed Mar. 7, 2012, which is a divisional of U.S. patent application Ser. No. 13/287,395, (now issued U.S. Pat. No. 8,153,433), filed Nov. 2, 2011, which is a divisional of U.S. patent application Ser. No. 12/819,533 (now issued U.S. Pat. No. 8,076,140), filed Jun. 21, 2010, which is a divisional of U.S. patent application Ser. No. 12/405,733 (now issued U.S. Pat. No. 7,785,880), filed Mar. 17, 2009, which is a divisional of U.S. patent application Ser. No. 11/487,215 (now issued U.S. Pat. No. 7,537,930), filed Jul. 14, 2006, which is a continuation-in-part of U.S. patent application Ser. No. 11/187,863 (now issued U.S. Pat. No. 7,531,327), filed Jul. 25, 2005, which claimed the benefit under 35 U.S.C. §119(e) of provisional U.S. Patent Application No. 60/590,349, filed Jul. 23, 2004, each of which is incorporated herein by reference in its entirety.

FIELD OF THE INVENTION

Various embodiments of the present invention concern methods and compositions for increasing longevity and/or protein yield from a cell line. In particular embodiments, the cell line may be a hybridoma cell line that produces antibodies or antibody fragments. In more particular embodiments, the methods may comprise transfecting a cell line with one or more genes, such as genes encoding E6, E7 and/or Bcl-2 or related proteins. Such proteins are not limited to their native sequence, but may include one or more substituted amino acids, such as a Bcl-2 with point mutations at T69E, S70E and S87E. Other embodiments concern mammalian cell lines that are capable of growth and protein production in serum-free medium. Such cell lines may be used in methods of protein production, by transfecting the cell line with an expression vector that expresses a heterologous protein, such as an antibody, bispecific antibody, multivalent antibody or multispecific antibody or fragment thereof. In preferred embodiments, the cell line may be transfected in serum-free medium, providing considerable time savings in avoiding having to adapt the transfected cell line for serum-free growth and protein production.

BACKGROUND OF THE INVENTION

Culturing cells in vitro, especially in large bioreactors, has been the basis of the production of numerous biotechnology products, and involves the elaboration by these cells of protein products into the support medium, from which these products are isolated and further processed prior to use clinically. The quantity of protein production over time from the cells growing in culture depends on a number of factors, such as, for example, cell density, cell cycle phase, cellular biosynthesis rates of the proteins, condition of the medium used to support cell viability and growth, and the longevity of the cells in culture (i.e., how long before they succumb to programmed cell death, or apoptosis). Various methods of improving the viability and lifespan of the cells in culture have been developed, together with methods of increasing productivity of a desired protein by, for example, controlling nutrients, cell density, oxygen and carbon dioxide content, lactate dehydrogenase, pH, osmolarity, catabolites, etc. For example, increasing cell density can make the process more productive, but can also reduce the lifespan of the cells in culture. Therefore, it may be desirous to reduce the rate of proliferation of such cells in culture when the maximal density is achieved, so as to maintain the cell population in its most productive state as long as possible. This results in increasing or extending the bioreactor cycle at its production peak, elaborating the desired protein products for a longer period, and this results in a higher yield from the bioreactor cycle.

Many different approaches have been pursued to increase the bioreactor cycle time, such as adjusting the medium supporting cell proliferation, addition of certain growth-promoting factors, as well as inhibiting cell proliferation without affecting protein synthesis. One particular approach aims to increase the lifespan of cultured cells via controlling the cell cycle by use of genes or antisense oligonucleotides to affect cell cycle targets, whereby a cell is induced into a pseudo-senescence stage by transfecting, transforming, or infecting with a vector that prevents cell cycle progression and induces a so-called pseudo-senescent state that blocks further cell division and expands the protein synthesis capacity of the cells in culture; in other words, the pseudo-senescent state can be induced by transfecting the cells with a vector expressing a cell cycle inhibitor (Bucciarelli et al., U.S. Patent Appl. 2002/0160450 A1; WO 02/16590 A2). The latter method, by inhibiting cell duplication, seeks to force cells into a state that may have prolonged cell culture lifetimes, as described by Goldstein and Singal (Exp Cell Res 88, 359-64, 1974; Brenner et al., Oncogene 17:199-205, 1998), and may be resistant to apoptosis (Chang et al., Proc Natl Acad Sci USA 97, 4291-6, 2000; Javeland et al., Oncogene 19, 61-8, 2000).

Still another approach involves establishing primary, diploid human cells or their derivatives with unlimited proliferation following transfection with the adenovirus E1 genes. The new cell lines, one of which is PER.C6 (ECACC deposit number 96022940), which expresses functional Ad5 E1A and E1B gene products, can produce recombinant adenoviruses, as well as other viruses (e.g., influenza, herpes simplex, rotavirus, measles) designed for gene therapy and vaccines, as well as for the production of recombinant therapeutic proteins, such as human growth factors and human antibodies (Vogels et al., WO 02/40665 A2).

Other approaches have focused on the use of caspase inhibitors for preventing or delaying apoptosis in cells. See, for example, U.S. Pat. No. 6,586,206. Still other approaches have tried to use apoptosis inhibitors such as members of the Bcl-2 family for preventing or delaying apoptosis in cells. See Arden et al., Bioprocessing Journal, 3:23-28 (2004). These approaches have yielded unpredictable results. For example, in one study, expression of Bcl-2 increased cell viability but did not increase protein production. (See Tey et al., Biotechnol. Bioeng. 68:31-43, 2000.) Another example disclosed overexpression of Bcl-2 proteins to delay apoptosis in CHO cells, but Bcl-xL increased protein production whereas Bcl-2 decreased protein production (see WO03/083093). A further example disclosed experiments using expression of Bcl-2 proteins to prolong the survival of Sp2/0-Ag14 (ATCC # CRL-1581, hereafter referred to as Sp2/0) cells in cultures. However, the cell density of the Bcl-2 expressing clones were 20 to 50% lower than that of their parental cultures, raising concerns for their practical application in biopharmaceutical industry (see WO03/040374; U.S. Pat. No. 6,964,199).

It is apparent, therefore, that improved host cells for high level expression of recombinant proteins and methods for reliably increasing recombinant protein production, in particular the production of antibodies and antibody fragments, multispecific antibodies, fragments and single-chain constructs, peptides, enzymes, growth factors, hormones, interleukins, interferons, and vaccines, in host cells are needed in the art. A need also exists for cell lines that are pre-adapted to grow in serum-free or serum-depleted medium, that can be transfected with expression vectors under serum free conditions and used for protein production without going through a lengthy adaptation period before serum-free growth and protein production.

SUMMARY OF THE INVENTION

Accordingly, it is an object of the present invention to provide improved host cells and methods to increase the longevity and/or recombinant protein yields of a cell culture by introducing into the cells agents that inhibit senescence or that promote cell survival, e.g., anti-apoptotic agents. The use of such agents preferentially increases the lifespan and viability of cells in culture used for the production of a desired recombinant protein, concomitantly increasing the productivity of such cells in culture, and thereby the optimal yield of the desired protein. Preferably, the apoptosis inhibitors used in the method of the present invention include but are not limited to Bcl-2 and its family members. Alternately, the longevity and recombinant protein yields of a cell clone can be improved by introducing into the cell agents that down-regulate the level of intracellular pro-apoptotic proteins, such as p53 and Rb, or up-regulate intracellular anti-apoptotic proteins, such as Bcl-2.

Preferably, the regulatory agents used in the method of the present invention include, but are not limited to, human papillomavirus type 16 (HPV-16) oncoproteins E6 and E7, anti-apoptosis protein Bcl-2 and combinations thereof. Additionally, caspase inhibitors, as described herein, may also contribute to blocking or reducing apoptosis, thus increasing cell survival and increasing the production of recombinant proteins by said cells in culture. A further class of anti-apoptotic agents that can be used in these cultures to enhance production of recombinant proteins includes certain members of the cytokine type I superfamily, such as erythropoietin (EPO). EPO, as a prototype molecule of this class, is a major modifier of apoptosis of multiple cell types, not just erythrocytes, and thus has more general cytoprotective functions, such as in endothelial cells, myocardial cells, tubular epithelial cells of the kidney, skin, and neurons [cf. review by P. Ghezzi and M. Brines, Cell Death and Differentiation 11 (suppl. 1), s37-s44, July 2004].

In various embodiments, the cell lines that have been transfected with one or more regulatory agents, such as HPV-16, E6, E7 and/or Bcl-2 may be pre-adapted for growth in serum-free medium. Such pre-adapted cell lines, including but not limited to the Sp/ESF cell line (see Examples below), are able to undergo further transformation, under serum-free conditions, with one or more expression vectors, thus allowing expression and protein production under serum-free conditions without extensive time required for adaption to serum-free growth. This surprising result allows protein production under serum free or low serum conditions, providing significant savings on medium cost. At the same time, transfection and protein production under serum-free conditions saves substantial time needed for serum-free adaptation that is required when using standard mammalian cell lines, which are only transfectable under serum-rich conditions and require an additional 6 to 12 months to adapt to serum-free protein production.

The present invention also teaches cell culture methods incorporating novel combinations of factors including, but not limited to, transfection vectors, screening and selection of cell clones with desired properties, cell culture media, growth conditions, bioreactor configurations, and cell types to create cell culture conditions in which the longevity of the cell culture is increased and/or made optimal and the yield of a desired recombinant protein is increased. These cell culture methods include suspension, perfusion, and fed-batch methods of production. See Tey et al., J. Biotechnol. 79: 147-159 (2000); Zhang et al., J. Chem. Technol. Biotechnol. 79: 171-181 (2004); Zhou et al., Biotechnol. Bioeng. 55: 783-792 (1997).

Unless otherwise defined, all technical and scientific terms used herein have their plain and ordinary meaning. In addition, the contents of all patents and other references cited herein are incorporated by reference in their entirety.

BRIEF DESCRIPTION OF DRAWINGS/FIGURES

FIG. 1 shows visual images of Sp2/0 and Sp-E26 cells treated with cycloheximide (+CHX) or untreated (−CHX).

FIG. 2 shows the results of screening HPV E6/E7 transduced cells that are more resistant to CHX treatment. A total of 55 clones were screened; in the first experiment, 31 clones were screened (top panel); in the second experiment, 24 clones were screened (bottom panel). Healthy cells of each clone were split into two equal portions. One was treated with CHX for 2 h and the other left untreated. The viable cells in these two cultures were then measured by MTT assay and the ratios of viable cell populations treated (CHX.sup.+) vs. untreated (CHX.sup.−) were plotted. As shown in the top panel, CHX treatment resulted in 30% reduction of viability in Sp2/0 cells, while only 6% reduction in Sp-E26 cells. Seven of the 31 clones screened (indicated by *) performed significantly better (<20% reduction of viability) than Sp2/0 but not as well as Sp-E26. For the 24 clones screened in the second experiment (bottom panel), CHX treatment resulted in about 50% reduction of viability in Sp2/0 cells and <20% reduction of viability in Sp-E26. Ten of the 24 clones (indicated by * or ) screened performed significantly better (<30% reduction) than Sp2/0, and 6 of them (indicated by ) matched or were better than Sp-E26 (<20%). E28 and E36 are two additional control clones that perform better than Sp2/0 but not as well as Sp-E26.

FIG. 5 shows the growth profiles of Sp2/0 and Sp-E26 cells in T-flasks. Healthy cells (>95% viability) were seeded in T-flasks at an initial cell density of 200,000/ml. Viable and dead cells were counted daily using Guava ViaCount reagent (Guava technologies, Inc.) and PCA instrumentation (Guava Technologies, Inc.). Accumulation of $NH_4^+$ and lactate also was monitored.

FIG. 6 compares the growth profiles of Sp2/0 and Sp-E26 cells as determined for a batch culture in 3-L bioreactors. Healthy cells (>95% viability) were seeded in the bioreactors at an initial cell density of 250,000/ml. Cells were counted daily by trypan blue and microscope.

Figure 7:
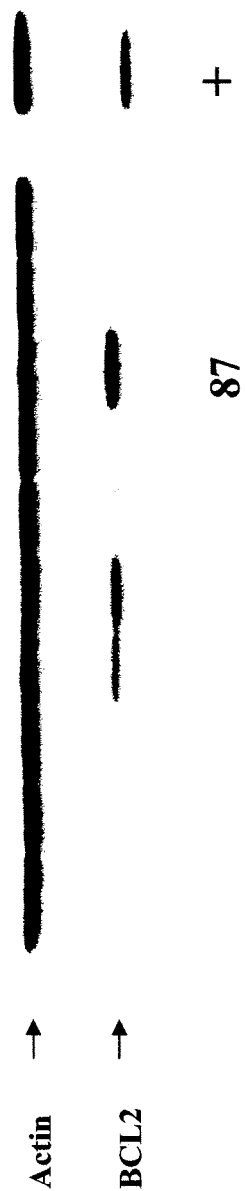

FIG. 7 shows a representative immunoblot stained with Bcl-2 (100) antibody (Santa Cruz Biotech.) and developed with enhanced chemiluminescence for screening of clones for Bcl-2-EEE expression.

Figure 8:
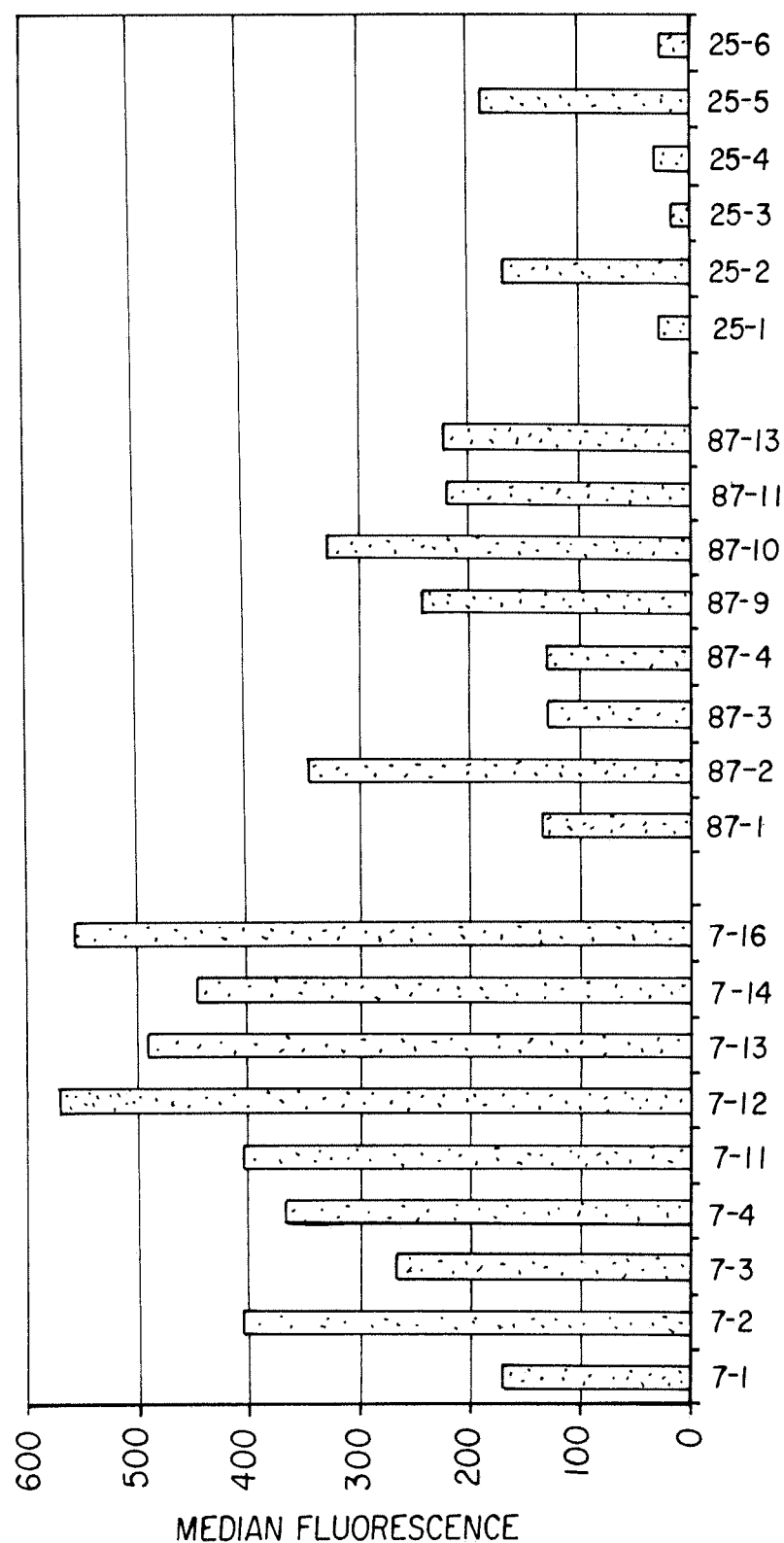

FIG. 8 shows a graph of flow cytometry results using Guava Express. Cells were fixed and permeabilized before staining with phycoerythrin-conjugated anti-Bcl-2 antibody (Santa Cruz Biotechnology, Inc.) Several sub-clones are compared.

Figure 9:
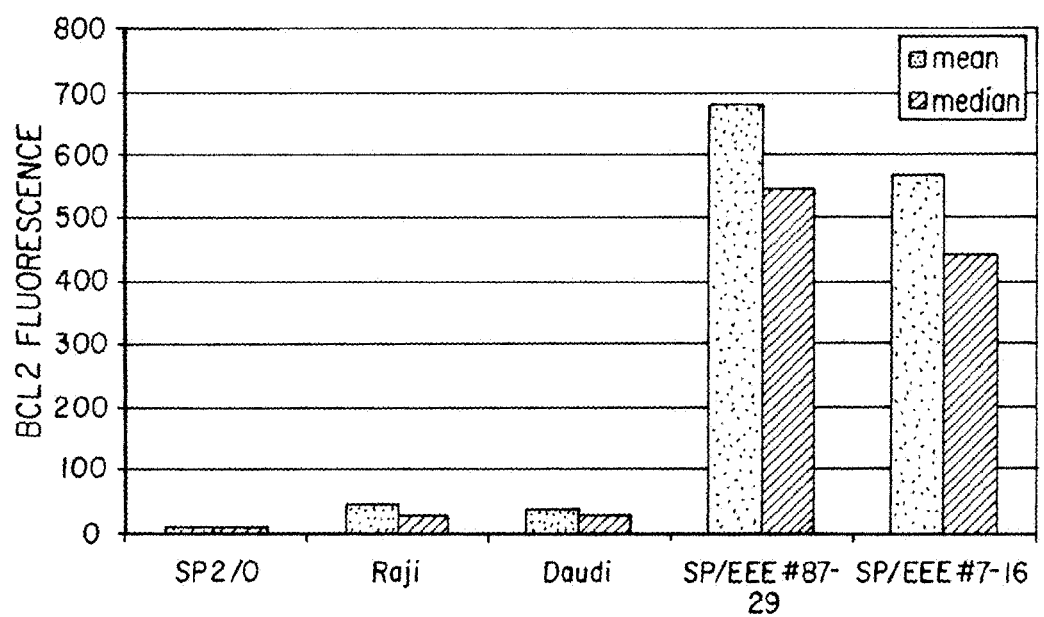

FIG. 9 shows a graph of flow cytometry results using Guava Express. Cells were fixed and permeabilized before staining with phycoerythrin conjugated anti-Bcl-2 antibody (Santa Cruz Biotechnology, Inc.). Sp2/0, Raji and Daudi cells were compared to Bcl-2-EEE clones.

Figure 10:
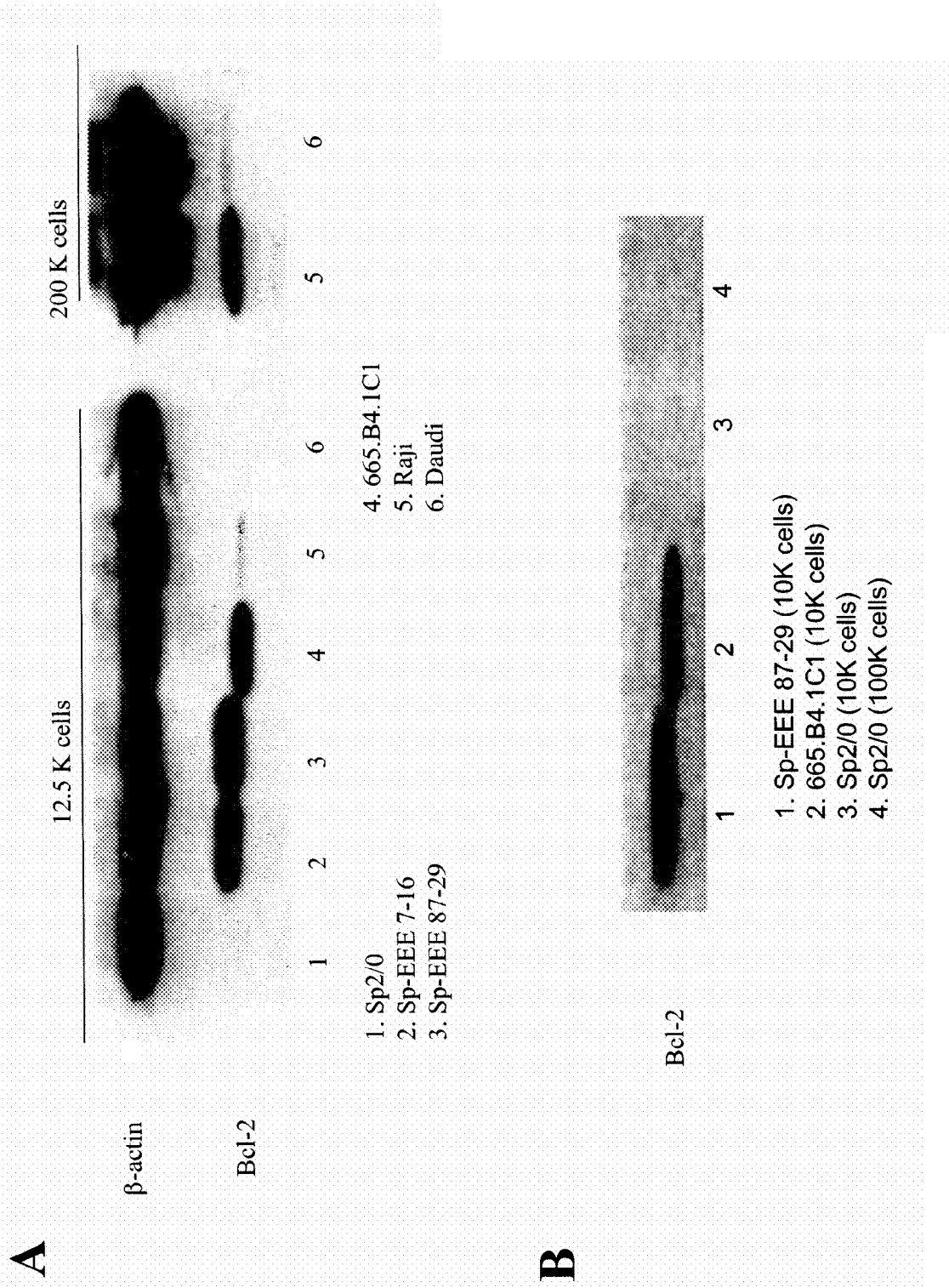

FIG. 10 shows the results of immunoblot analyses of 665.B4.1C1, Sp2/0, Raji, Daudi, Sp-EEE (87-29 clone) and Sp-EEE (7-16 clone) cell lysates. (A) Blots stained with a human Bcl-2 specific antibody (Santa Cruz Biotechnology, Inc). (B) Blot stained with an anti-Bcl-2 antibody (Santa Cruz Biotechnology, Inc) that recognizes mouse and human Bcl-2.

Figure 11A:
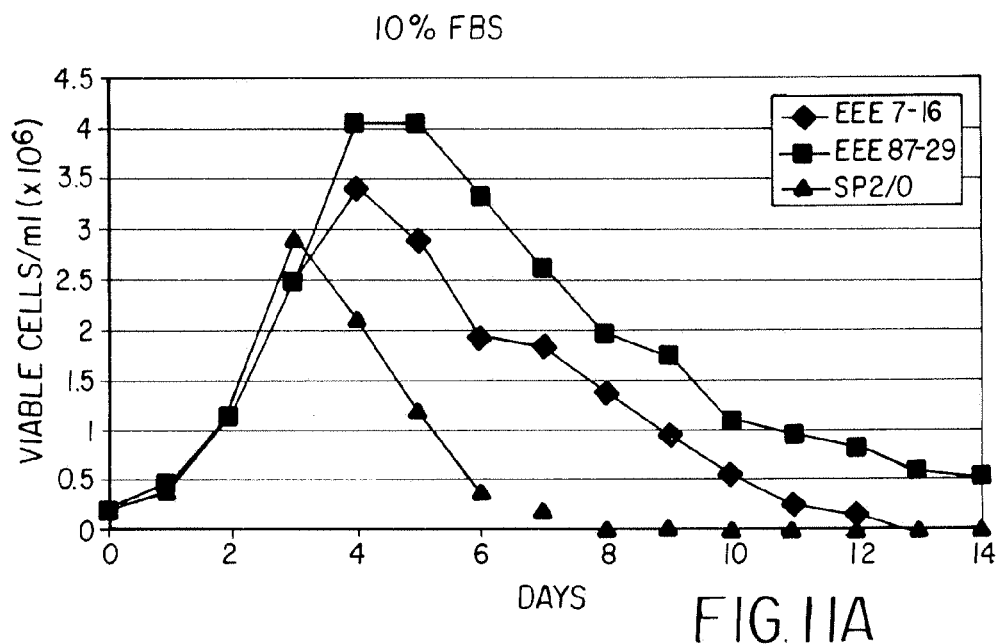
Figure 11B:
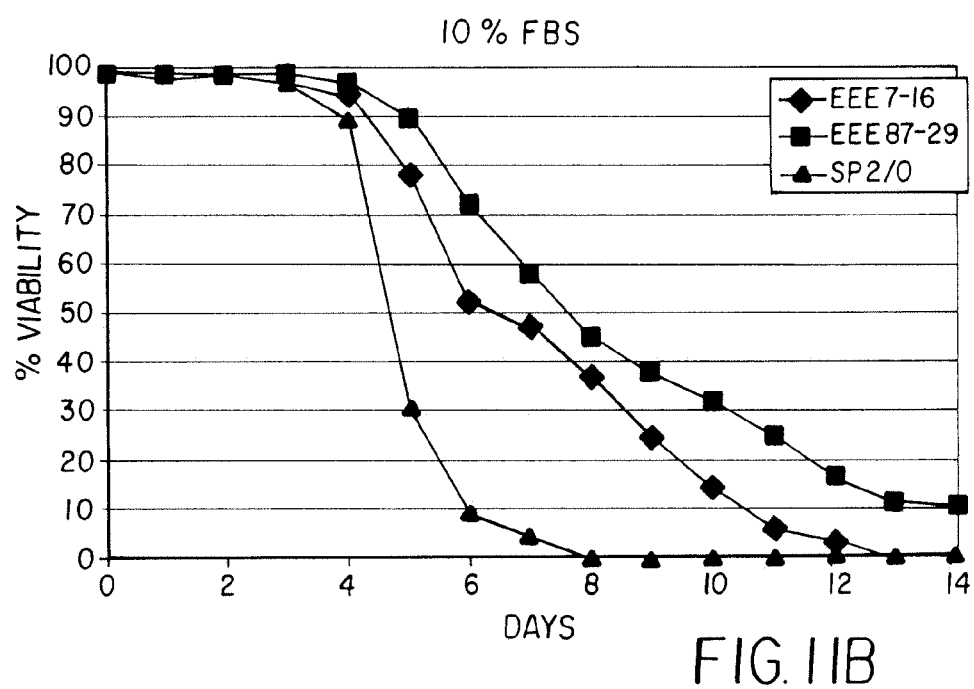

FIG. 11 shows growth curves (A) and viability (B) of Sp-EEE clones compared to Sp2/0 cells grown in media supplemented with 10% fetal bovine serum.]

Figure 12A:
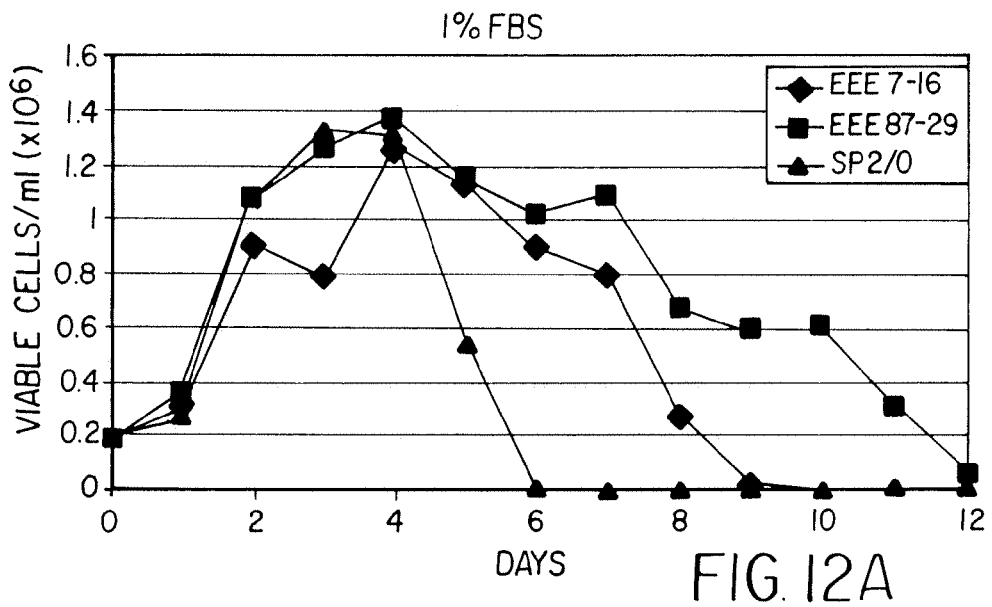
Figure 12B:
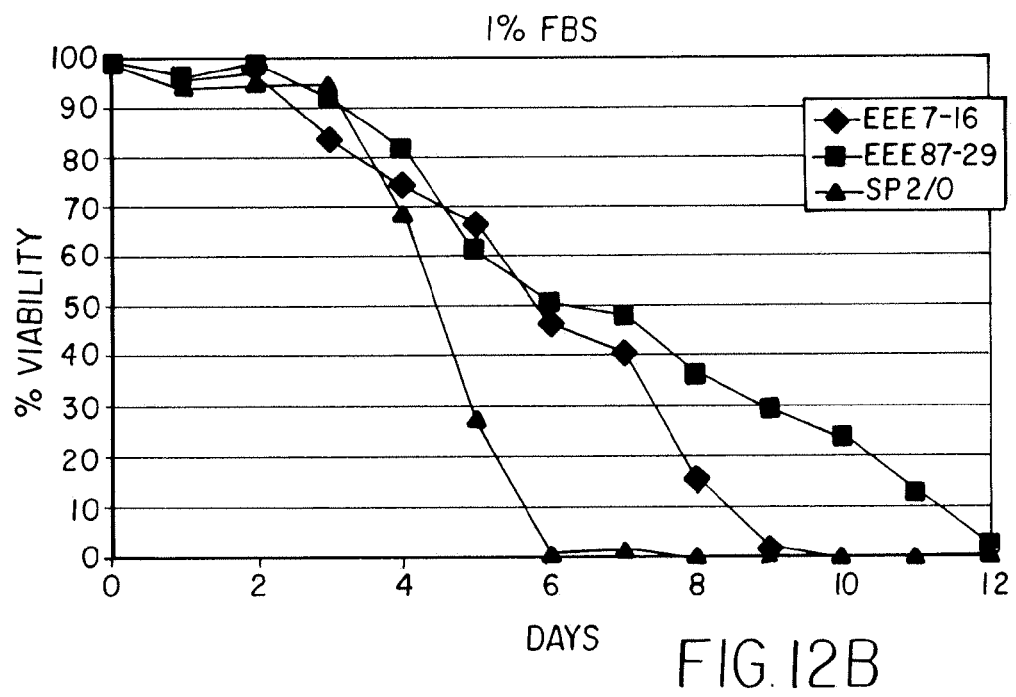

FIG. 12 shows growth curves (A) and viability (B) of Sp-EEE clones compared to Sp2/0 cells grown in media supplemented with 1% fetal bovine serum.

Figure 13A:
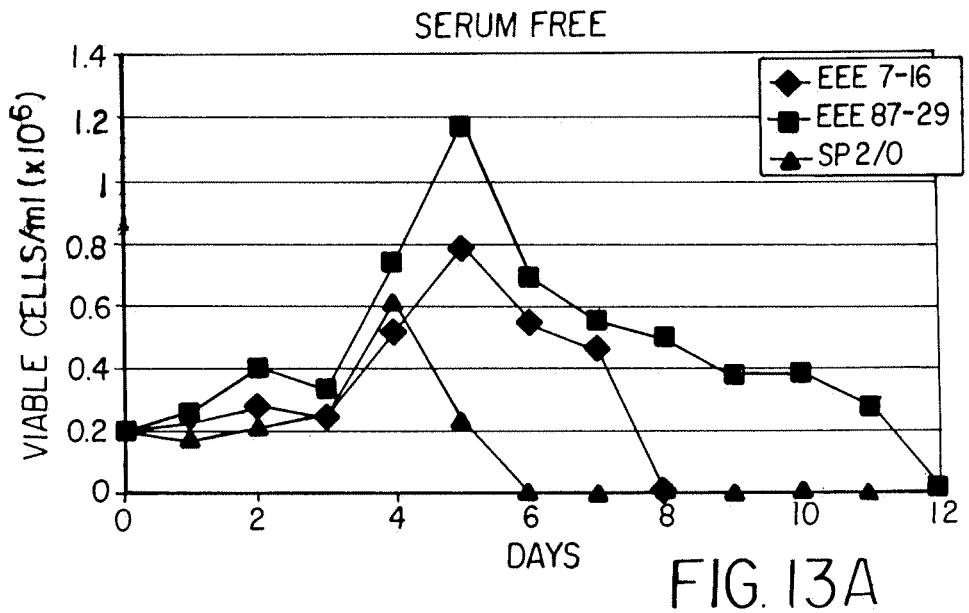
Figure 13B:
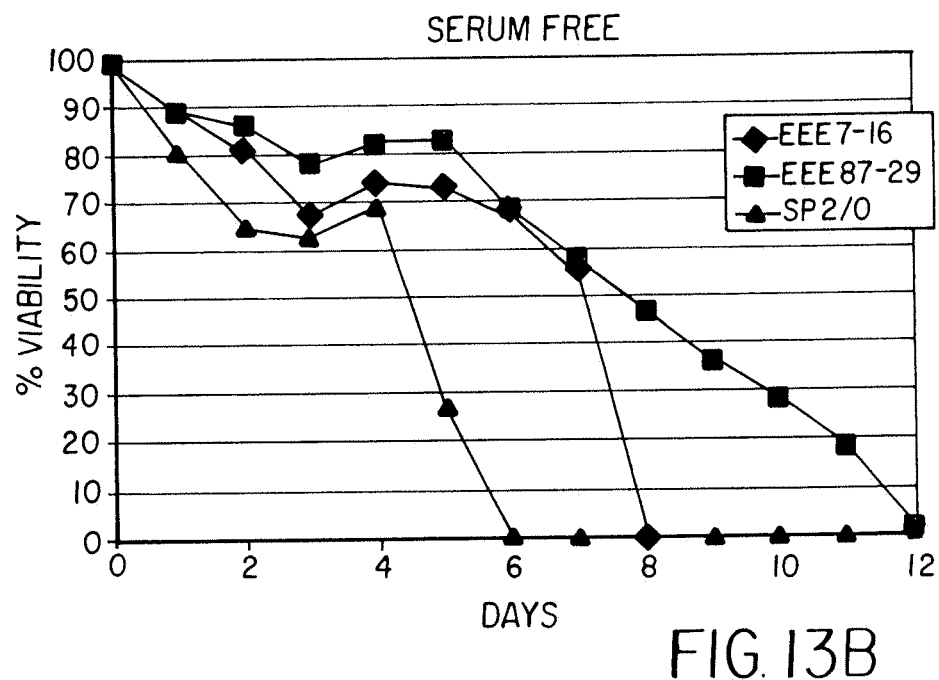

FIG. 13 shows growth curves (A) and viability (B) of Sp-EEE clones compared to Sp2/0 cells grown in serum-free media.

Figure 14:
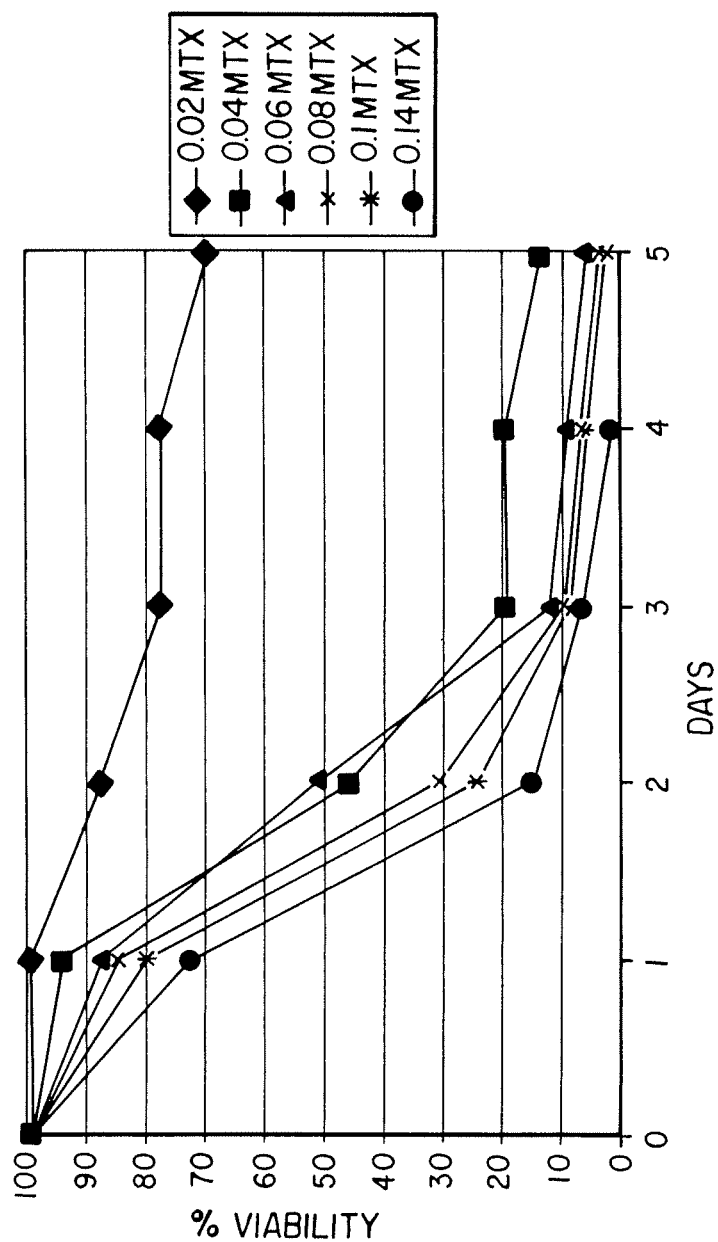

FIG. 14 shows methotrexate kill curves for Sp-EEE (87-29 clone) cells.

Figure 15:
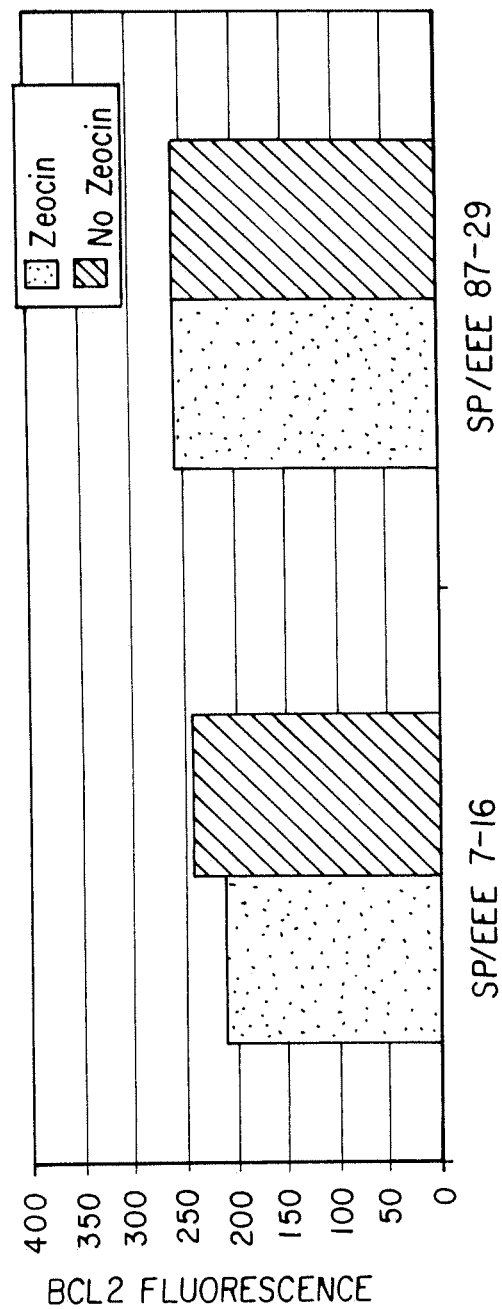

FIG. 15 shows a graph of flow cytometry results using Guava Express comparing Sp-EEE clones grown in the presence or absence of 1 mg/ml zeocin. Cells were fixed and permeabilized before staining with phycoerythrin conjugated anti-Bcl-2 antibody (Santa Cruz Biotechnology, Inc).

Figure 16:
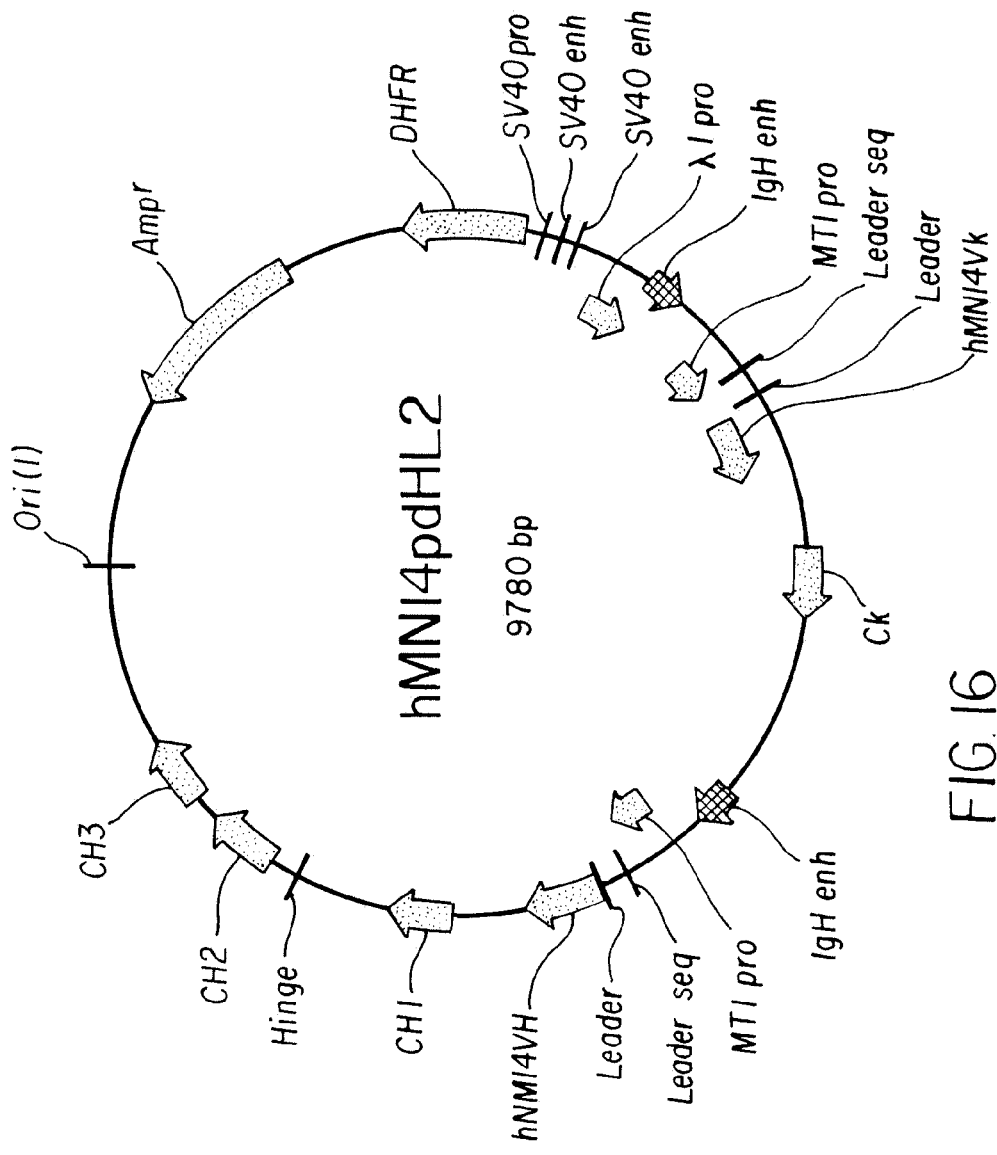

FIG. 16 shows the map of the pdHL2 vector used to transfect Sp2/0 cells to obtain the 665.2B9 clone with humanized antibody sequences and the SV40 promoter and enhancer sequences.

Figure 17:
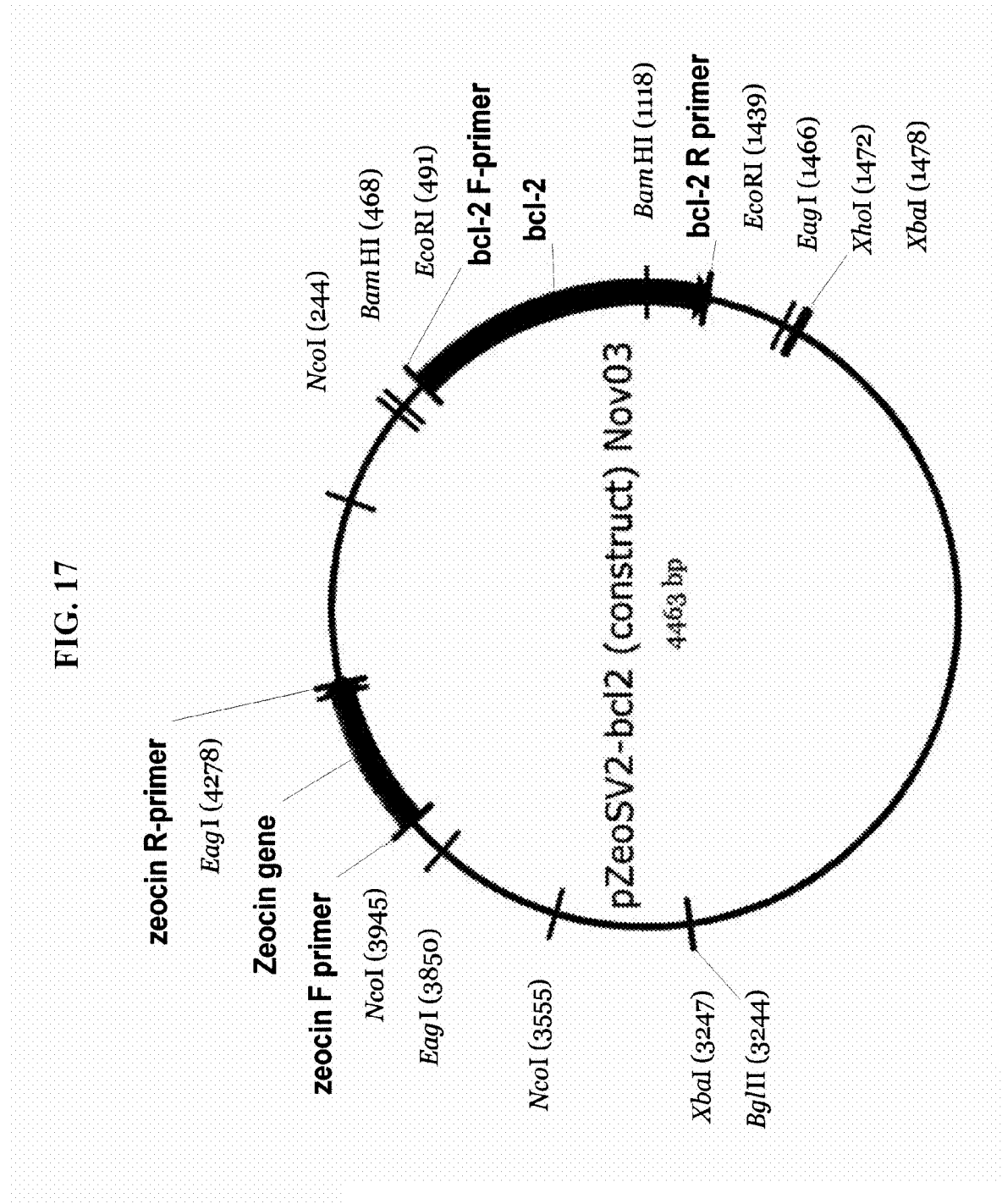

FIG. 17 shows the map of DNA plasmid with incorporated Bcl-2 gene, used for transfection of clone 665.2B9

Figure 18:
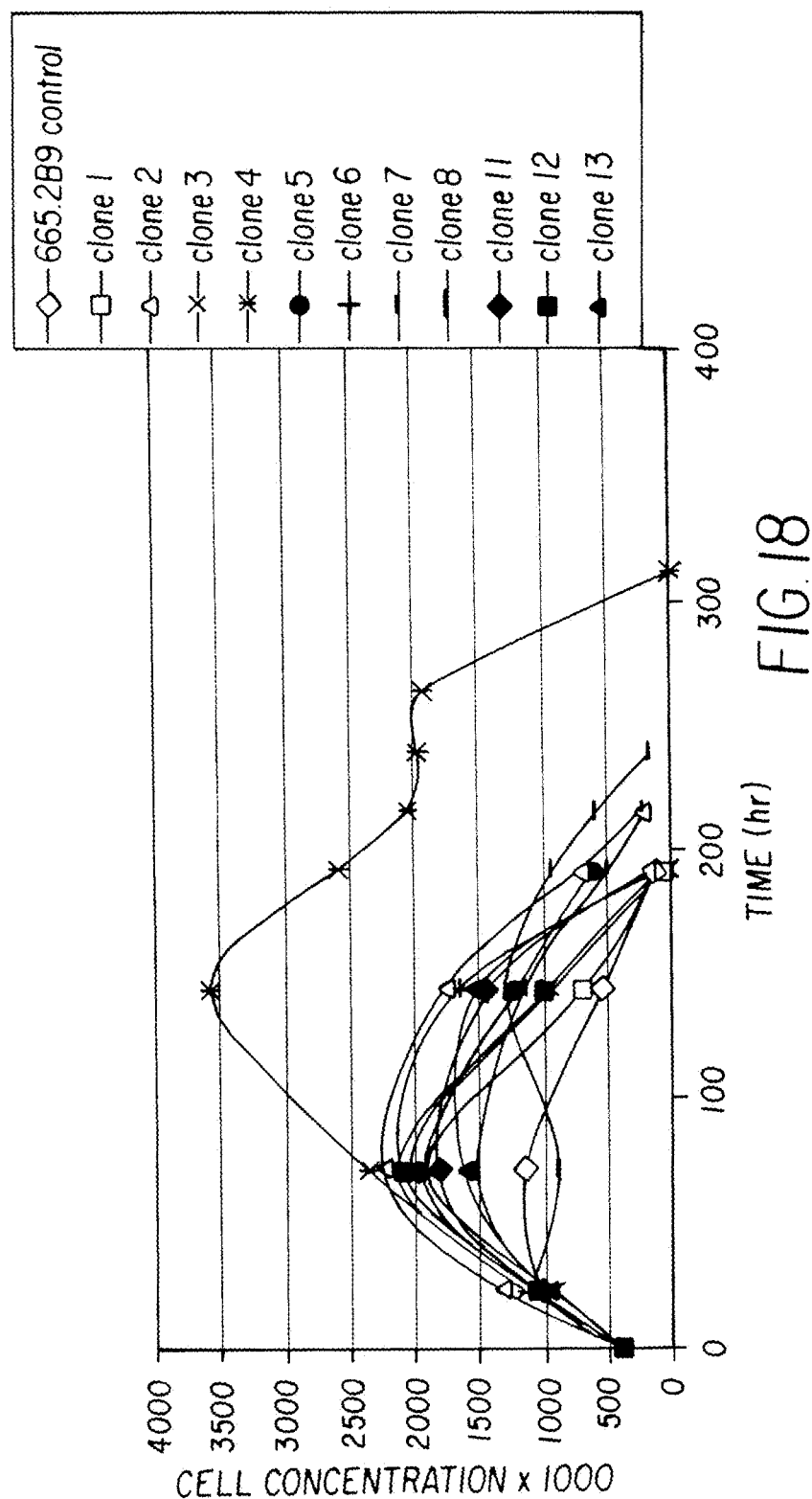
Figure 19:
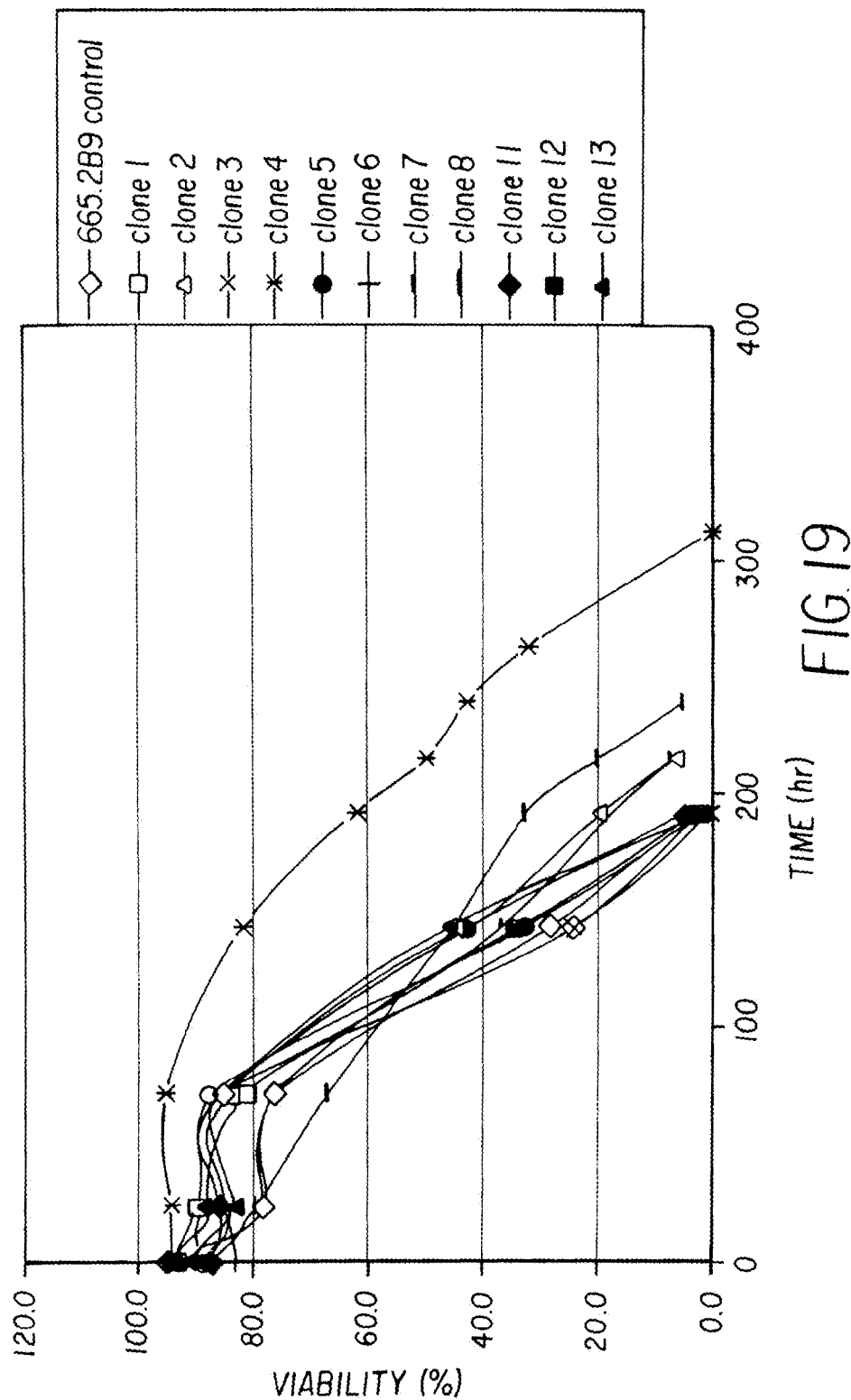

FIG. 18 and FIG. 19 show the growth profiles of Bcl-2 transfected clones 665.2B9#4, Bcl-2 negative clones and untransfected control. Healthy cells (>95% viability) were seeded in 24-well plates at an initial cell density of 400,000/ml. Viable and dead cells were counted daily using Guava ViaCount reagent and PCA instrumentation.

Figure 20:
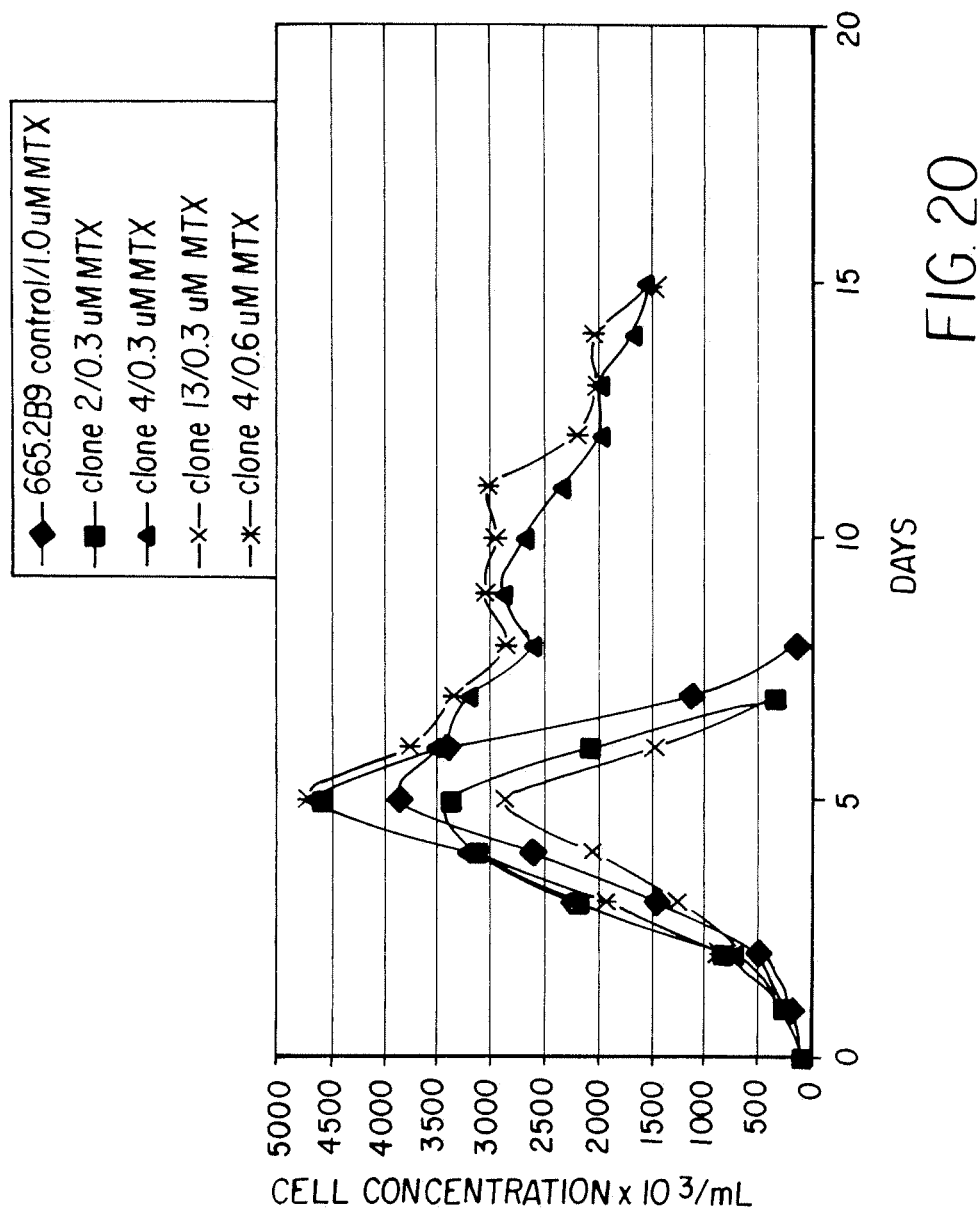
Figure 21:
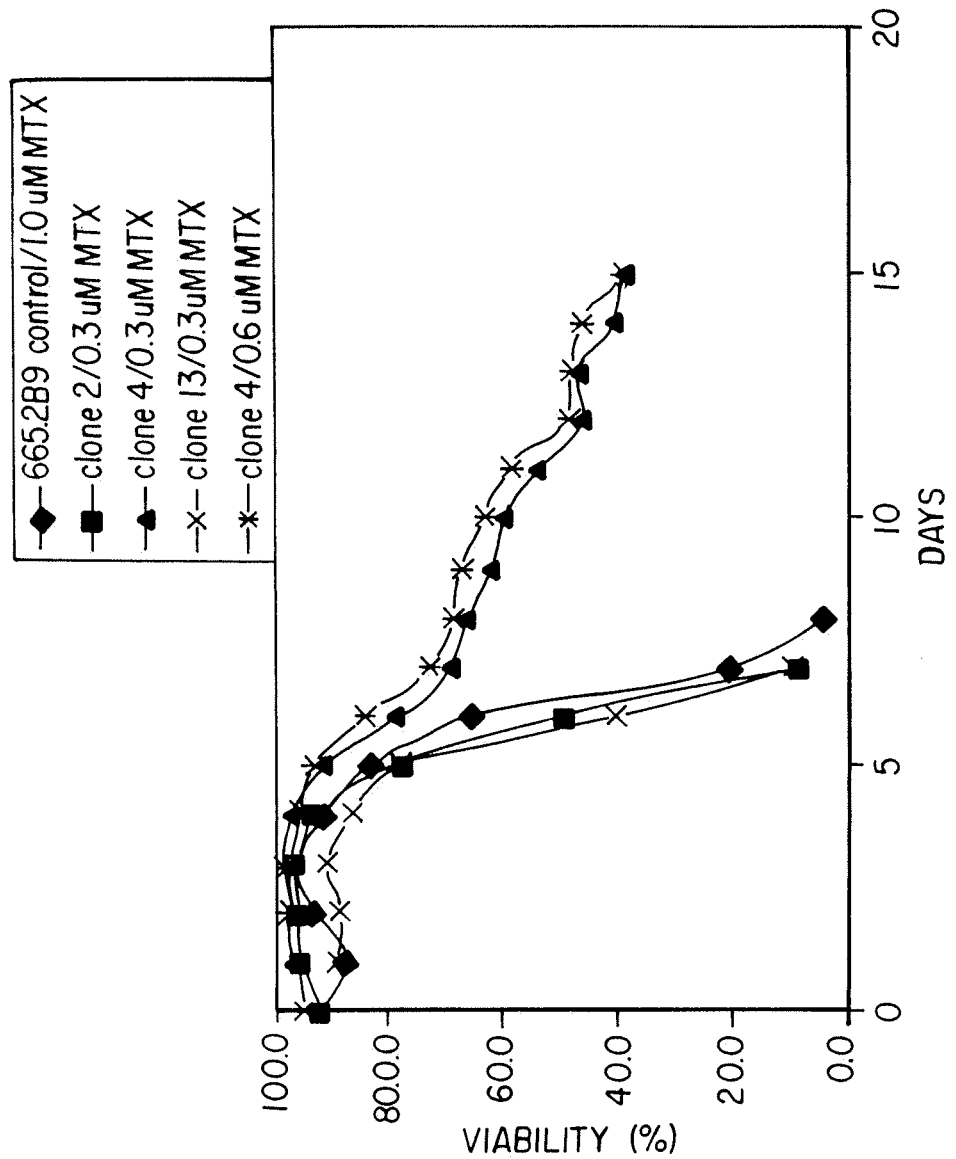

FIG. 20 and FIG. 21 show growth profiles of Bcl-2 transfected clone 665.259#4 and Bcl-2 negative clones in different MTX concentration. Healthy cells (>95% viability) were seeded in T-flasks at initial cell density of 100,000/ml. Viable cell density and viability were counted daily using Guava ViaCount reagent and PCA instrumentation.

Figure 22:
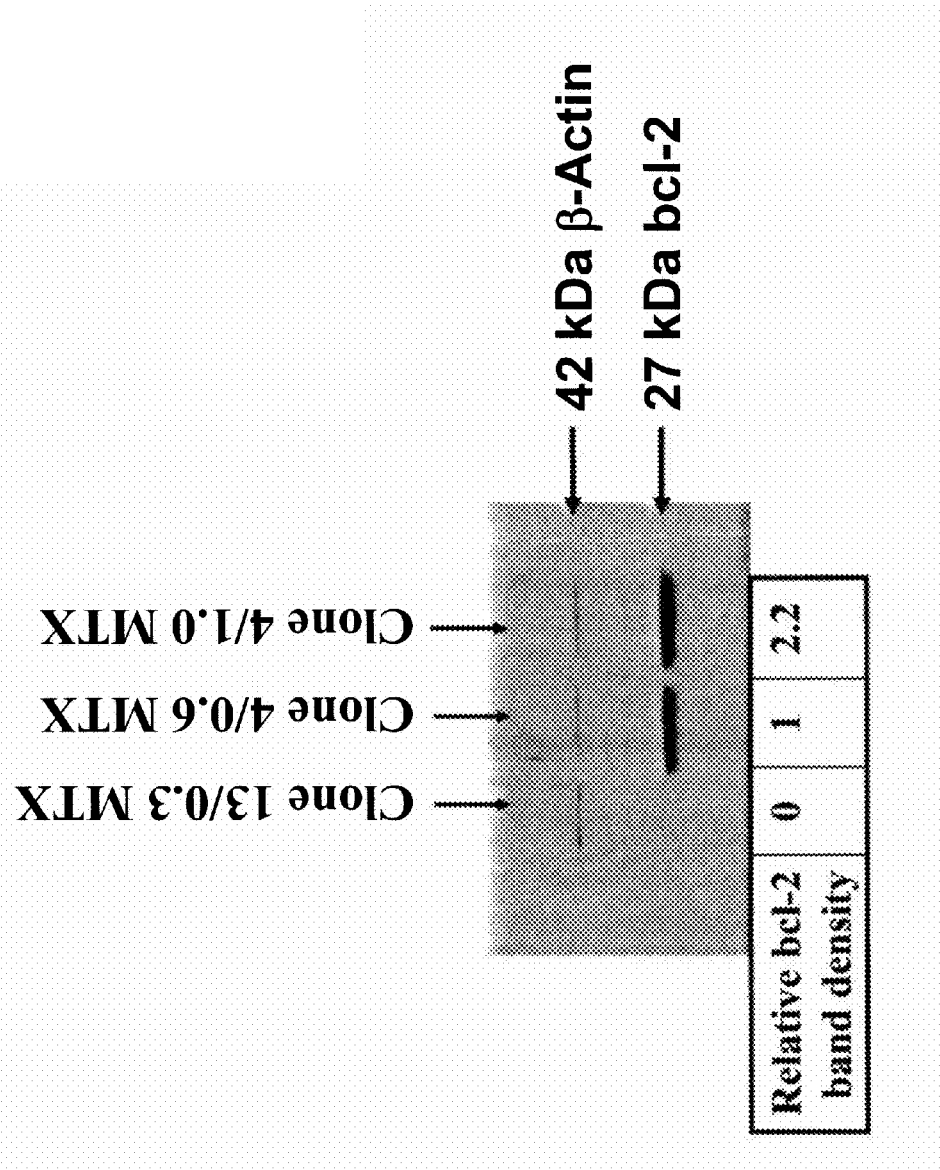

FIG. 22 shows the levels of human Bcl-2 expressed by clone 665.2B9#4 in increasing concentrations of MTX and clone #13 detected by Western blotting.

Figure 23:
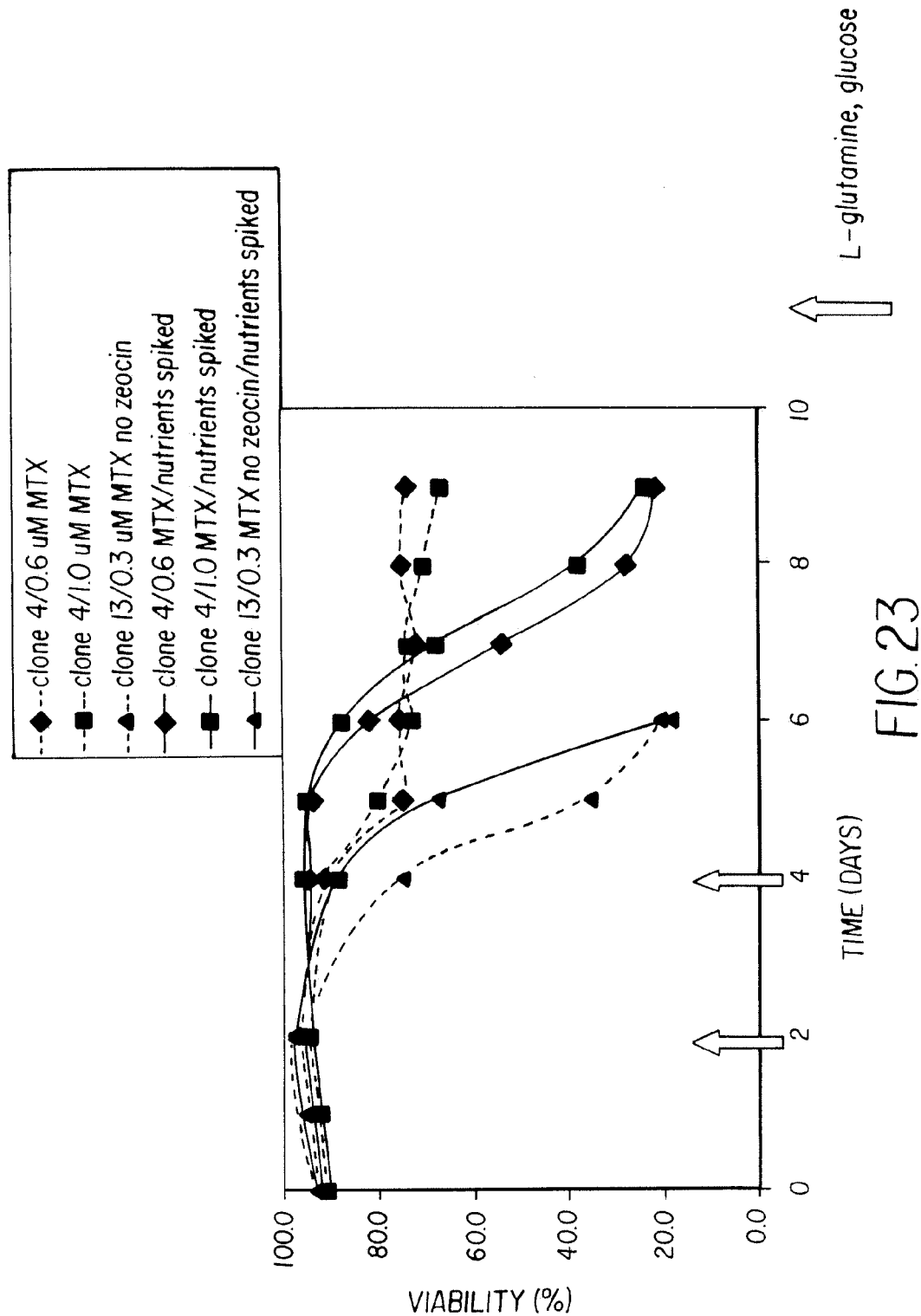
Figure 24:
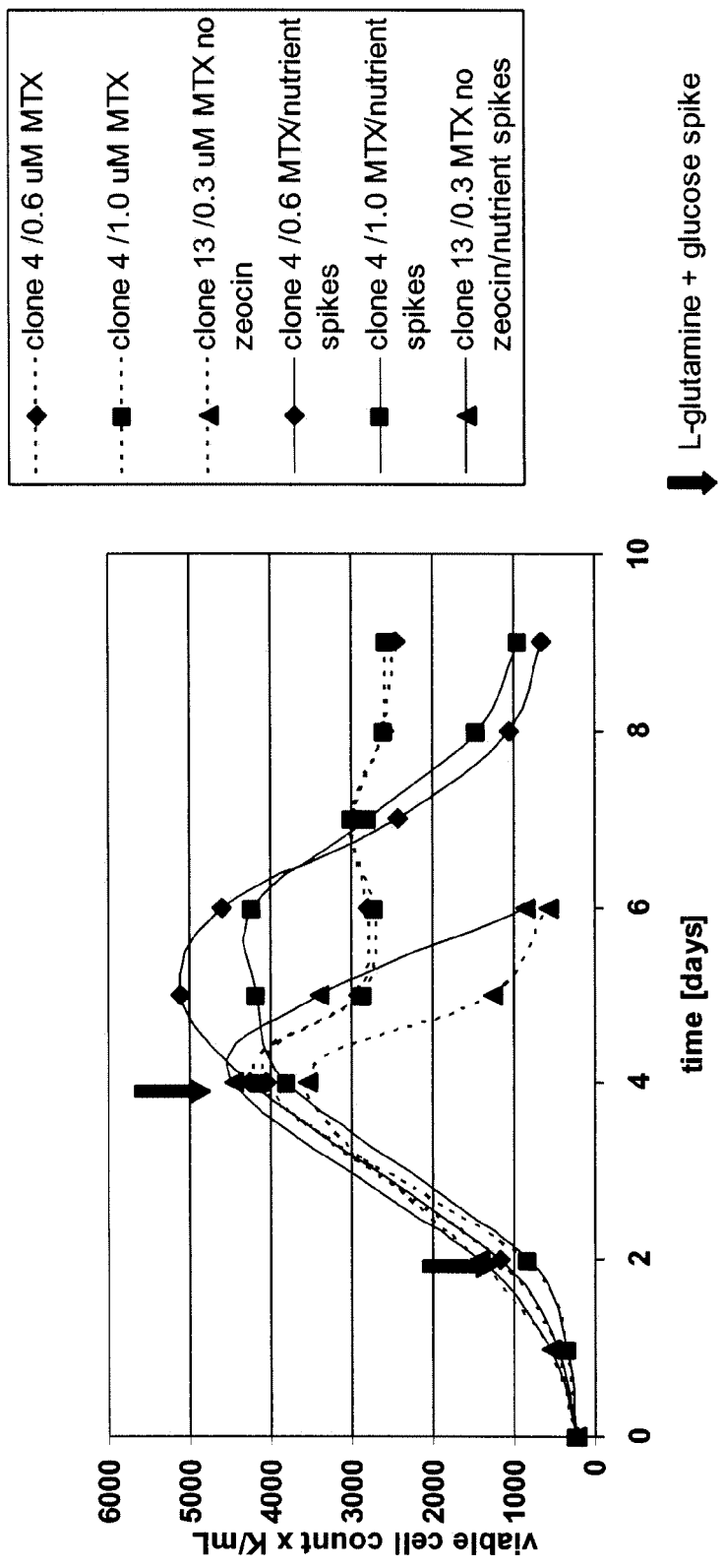

FIG. 23 and FIG. 24 show the profiles of cell viability and viable cell density, respectively, of clone 665.2B9#4 cultured in 0.6 and 1.mu.M of MTX and the Bcl-2-negative clone #13 cultured in 0.3 .mu.M MTX with or without spiking L-glutamine and glucose. Healthy cells (>95% viability) were seeded in roller bottles at an initial cell density of 200,000/ml. On day 2 and 4 (arrows indicated), a nutrient supplement solution containing glucose and L-glutamine was added to the "spiked" culture. Viable and dead cells were counted daily using Guava ViaCount reagent and PCA instrumentation.

Figure 25:
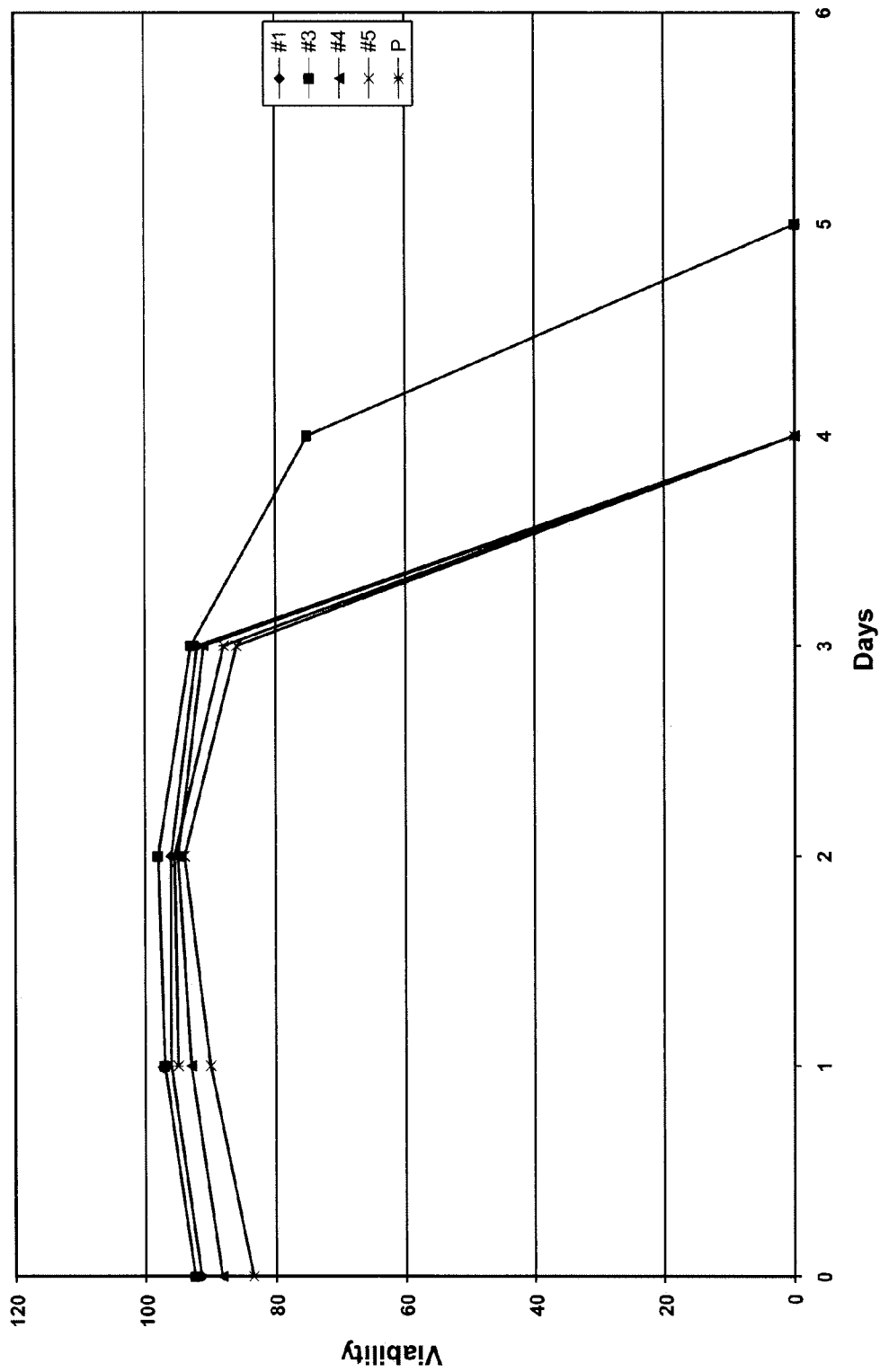

FIG. 25 shows the viability in serum-free medium of adapted Sp/EEE sub-clones over 5 days of culture.

Figure 26:
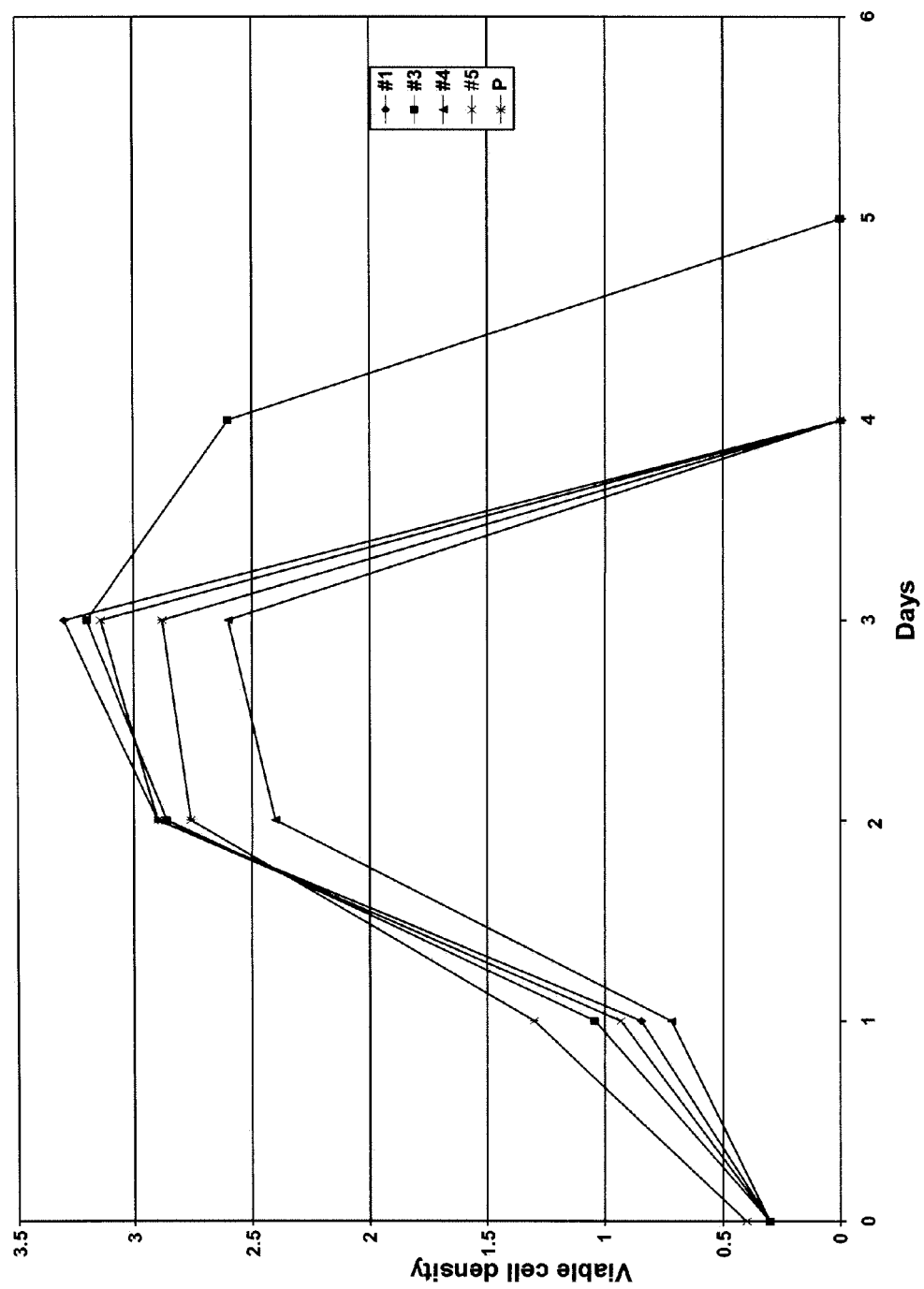

FIG. 26 illustrates the viable cell density of serum-free Sp/EEE sub-clones over 5 days of culture.

DETAILED DESCRIPTION OF THE INVENTION

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

As used herein, the term "about" means plus or minus ten percent. I.e., "about 100" means a number between 90 and 110.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion or analog of an immunoglobulin molecule, like an antibody fragment.

An antibody fragment is a portion of an antibody such as F(ab)$_2$, F(ab')$_2$, Fab, Fv, sFv and the like. Regardless of structure, an antibody fragment binds with the same antigen that is recognized by the intact antibody. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units (CDR) consisting of the amino acid residues that mimic the hypervariable region.

As used herein, the term antibody fusion protein refers to a recombinantly produced antigen-binding molecule in which two or more of the same or different scFv or antibody fragments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds to one such epitope, for example a diabody with two binding site reactive with the same antigen. The fusion protein may comprise a single antibody component, a multivalent or multispecific combination of different antibody components, or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

Cell Lines

Various embodiments of the present invention concern improved compositions, including host cell lines, and methods for enhanced production of recombinant proteins in such cell lines. Cell lines have been created that constitutively express one or more anti-apoptotic genes and that can be transfected with an expression construct encoding a protein or peptide of interest, where expression of the anti-apoptotic gene(s) prolongs survival of the transfected cell in culture and provides for enhanced yields of the protein or peptide of interest.

Specific embodiments concern derivatives of the Sp2/0 myeloma cell line that provide novel cell lines, referred to as Sp-E26, Sp-EEE and Sp-ESF, which show enhanced survival in batch culture. Sp-E26 constitutively expresses the E6 and E7 proteins of HPV-16. Sp-EEE and Sp-ESF constitutively express a Bcl-2 mutant, referred to as Bcl-2-EEE. In addition, recombinant protein production, and particularly production of recombinant antibodies and antibody fragments, can be improved upon transfecting Sp-E26, Sp-EEE or Sp-ESF with an expression vector for the recombinant protein of interest. The E6/E7 or Bcl-2-EEE proteins delay induction of apoptosis in the host cells and permit enhanced recombinant protein production in the host cells. Protein production can be boosted still further by addition of one or more caspase inhibitors (e.g., caspase 1 and/or 3 inhibitors) (Bin Yang et al. Nephron Experimental Nephrology 2004; 96:e39-e51), and/or by addition of one or more members of the cytokine type I superfamily, such as erythropoietin (EPO), into the growth medium of the cells. A pan-caspase inhibitor is particularly effective in this regard.

Further, the Sp-EEE cell line can be pre-adapted for growth and protein production in serum-free or low-serum conditions, resulting in serum-free pre-adapted cell lines such as Sp-ESF. The Sp-ESF and similar cell lines may be transfected with one or more expression vectors encoding a protein of interest, such as an antibody, antibody fragment, bispecific antibody, etc. The use of serum-free conditions for transfection, which is unique among mammalian cell lines available for transfection and protein production, saves a significant amount of time required for adaptation to serum-free growth.

Production of recombinant proteins, such as antibodies or antibody fragments, can be significantly enhanced in the host cell by co-expression of an apoptosis inhibitor, such as Bcl-2. In particular, protein production is significantly enhanced in a myeloma cell line, such as Sp2/0, that is stably transfected with an expression vector encoding an antibody or antibody fragment and that is co-transfected with an expression vector encoding an apoptosis inhibitor, such as Bcl-2. Increased production of antibody can also be obtained from a host cell transfected with the E6/E7 gene. Recombinant protein production can be boosted still further by addition of one or more caspase inhibitors into the growth medium of the cells. A pan-caspase inhibitor is particularly effective in this regard. Also, recombinant protein production can be enhanced by feeding EPO, or another anti-apoptotic cytokine, into the medium of the cell culture.

Physiological, or programmed, cell death, referred to as apoptosis (Kerr et al., Br J. Cancer., 26:239-257, 1972) is essential for proper tissue development and maintenance and is controlled by an intrinsic genetic program that has been conserved in evolution (Ellis et al., Annu Rev Cell Biol, 7, 663-698, 1991). Hence, when cells grow in artificial environments, such as ex vivo cultures, this genetic endowment results in a finite lifespan. Therefore, the utility of such cell cultures for the production of proteins used in medicine and industry, as well as research, is dependent on maintaining such cultures for extended lifespan, or cycles, before they die according to apoptotic mechanisms.

Methods and agents have been discovered that act independently on cell proliferation and cell death events, by differentiating cell cycle from apoptotic effects. Bcl-2, a well-known intracellular regulator of apoptosis (Vaux et al., Nature 335, 440-2, 1988), is a proto-oncogene that has been found to have an anti-apototic effect that is genetically different from its inhibitory influence on cell cycle entry (Huang et al., EMBO J. 16, 4628-38, 1997). Two homologues of Bcl-2, Bcl-$x_L$ and Bcl-w, also extend cell survival, but other members of the Bcl-2 family, such as Bax and Bak, are pro-apoptotic (Oltvai et al., Cell 74, 609-19, 1993; Chittenden et al., Nature 374, 733-6, 1995; Farrow et al., Nature 374, 731-3, 1995; Kiefer et al., Nature 374, 736-9, 1995). Other anti-apoptotic genes include Bcl-6 and Mcl-1.

Thus, Bcl-2 and certain of its family members exert protection against apoptosis, and it may be used in a method to increase the lifespan of certain host cells in culture that are used for the production of proteins, thereby enhancing the amount of proteins produced and isolated. Over-expression of an anti-apoptotic Bcl-2 family member, such as Bcl-2, BCl-$x_L$, Bcl-w or mutant varieties of these proteins, inhibits apoptosis, resulting in increased cell density and longer culture survival. Hence, transfection of anti-apoptotic Bcl-2 family genes avoids the necessity to prolong the cell culture by interfering with the cell cycle per se, as others have proposed (ibid.). Similarly, transfection of fibroblasts with genes for Bcl-2 results in over-expression of Bcl-2 in these cells, resulting in an antagonism of apoptosis and increasing the lifespan of these cells, with a concomitant increase in the production and isolation of recombinant proteins. It has also been observed that upon cytokine withdrawal, interleukin-6 (IL-6)-dependent murine myeloma cells expire as if they undergo apoptosis. It was also found that IL-6-receptors in such cells could be regulated by Bcl-2 or Bcl-$x_L$ in extending apoptosis (Schwarz et al., Cancer Res 55:2262-5, 1995).

It has been reported that a mutant Bcl-2 possessing three point mutations (T69E, S70E and S87E) exhibited significantly more anti-apoptotic activity compared to wild type or single point mutants (Deng et al., PNAS (101) 153-158, 2004). Thus, various embodiments concern the construction of an expression vector for a Bcl-2-EEE triple mutant, which was then used to transfect Sp2/0 cells to create Sp-EEE clones and subclones that show improved longevity and recombinant protein production.

Other agents, such as oncogenic viruses, can also oppose apoptosis as part of their eliciting cellular immortalization and ultimately complete malignant transformation, such as high-risk type HPV oncoproteins E6 and E7 (Finzer et al., Cancer Lett 188, 15-24, 2002). For example, the viral E6 protein effectively blocks the epidermal apoptotic response to ultraviolet light (Storey, Trends Mol Med 8, 417-21, 2002). It has also been suggested, from indirect evidence, that the human papillomavirus may cause reduced apoptosis in squamous (but not basal cell) carcinoma (Jackson et al., Br J Cancer 87, 319-23, 2002). However, not all papillomavirus oncoproteins have anti-apoptotic effect. For example, other studies have reported that the papillomavirus E6 protein of bovine species sensitizes cells to apoptosis (Liu et al., Virology 295, 230-7, 2002), which is in contrast to other studies showing that HPV-16 E7 gene protects astrocytes against apoptosis induced by certain stimuli (Lee et al., Yonsei Med J 42, 471-9, 2001). By use of E6-binding peptide aptamers, direct experimental evidence was obtained that HPV E6 oncoprotein has anti-apoptotic activity in HPV-positive tumor cells (Butz et al., Proc Natl Acad Sci USA 97, 6693-7, 2000). However, other HPV oncoproteins can have the opposite effect. The E2 protein induces apoptosis in the absence of other HPV proteins (Webster et al., J Biol Chem 275, 87-94, 2000).

Continuous expression of both the E6 and E7 proteins is known to be required for optimal proliferation of cervical cancer cells and the two viral proteins exert distinct effects on cell survival (DeFilippis et al., J Virol 77, 1551-63, 2003). The primary intracellular target attributed to HPV-16 E6 is p53. E6 forms a ternary complex with p53 and a cellular ubiquitin ligase, E6AP, resulting in the ubiquitination and degradation of p53 through the proteosome pathway and inactivation of p53. On the other hand, HPV-16 E7 protein interacts and destabilizes the tumor suppressor protein Rb. Moreover, levels of a variety of other intracellular proteins involved in apoptosis and cell cycle pathways were reported to be regulated by E6 and E7 transformation, such as Bcl-2, Bcl-$x_L$, p73, MDM2, p21, cyclins and cdc, cdk proteins, etc. Changes in the expression of these proteins will greatly influence the physiological properties of the cell. The present inventors therefore hypothesized that transfection of cells in culture by HPV-16E6 and E7 would be effective in generating genetically modified clones that are resistant to aging-culture-condition induced apoptosis and, therefore, prolong the lifespan of the cell culture. It was also postulated that introduction into a cell of either HPV-16 oncoprotein E7 or E6 alone might be sufficient to generate genetically modified clones with improved resistance to aging-culture-condition induced apoptosis. When the cell is a recombinant protein-producing clone, the improved physiological properties would in turn translate into enhanced overall protein productivity.

Generation of New Host Cells Expressing Viral Anti-Apoptotic Genes

Host cells, such as myeloma host cells, can be generated that constitutively express viral anti-apoptotic genes, such as HPV-16 E6 and E7 proteins. These host cells can be transfected with an expression vector that encodes a recombinant protein of interest and co-expression of the anti-apoptotic genes results in significantly increased production of the recombinant protein.

The host cell can be essentially any host cell suitable for recombinant protein production that can be stably transformed with the viral anti-apoptosis genes. For many recombinant proteins, host cells such as CHO and COS cells are advantageous, while for other proteins, such as antibodies, host cells such as myeloma cells and CHO cells are the common choices. Other examples of useful host cell lines are VERO and HeLa cells, Chinese hamster ovary (CHO) cell lines, W138, BHK, COS-7, 293, HepG2, 3T3, NSO, NS1, RIN and MDCK cell lines. Cell lines of use may be obtained from commercial sources, such as the COS-1 (e.g., ATCC CRL 1650), COS-7 (e.g., ATCC CRL-1651), HEK293, BHK21 (e.g., ATCC CRL-10), P3X3Ag8.653 (ATCC CRL-1580), CHO (e.g., ATCC CRL 1610) and BSC-1 (e.g., ATCC CRL-26) cell lines. The viral (e.g., E6/E78) and/or eukaryotic genes can be introduced into the host cell by any suitable method that results in constitutive or inducible expression of the genes, i.e., any method that permits stable integration of the genes into the host cell chromosome while permitting expression of the genes. Methods for stable transformation of host cells with a gene of interest are well known in the art. A particularly advantageous method is to use a retroviral vector that encodes the viral anti-apoptosis genes. Suitable vectors include the LSXN vector (Miller et al. Biotechniques 7, 980-90, 1989). However, any alternative methods known in the art, such as electroporation or cell fusion, may be utilized.

Advantageously, the vector used to transfect the host cell contains a selectable marker that permits selection of cells containing the vector. Suitable selection markers, such as enzymes that confer antibiotic resistance on transfected cells, are well known in the art. After transfection, cells are maintained in a medium containing the selection agent, such as an antibiotic, and screened for resistance to the marker. Cells can be selected and cloned by limiting dilution using conventional methods.

The ability of the viral anti-apoptosis genes to increase cell viability can be tested by challenging the cells with an agent that induces apoptosis, such as cycloheximide (CHX). Cells that do not express the viral anti-apoptosis genes tend to demonstrate significant onset of apoptosis, whereas cells expressing the genes exhibit drastically reduced apoptotic activity. Methods of detecting apoptosis are well known in the art and include, for example, cell surface FITC-Annexin V binding assay, DNA laddering assay and TUNEL assay.

Upon selection of suitable cells expressing the viral anti-apoptosis genes, the cells can be transfected with an expression vector encoding the recombinant protein of choice. The expression vector can be a vector suitable for transient expression or, advantageously, can be an episomal vector containing a eukaryotic origin of replication, or an amplifiable vector that permits stable integration and subsequent gene amplification of the expression cassette. Suitable vectors are well known in the art and include, for example, the pdHL2 vector, which is particularly suited for production of antibodies and antibody fragments. When an amplifiable expression cassette is used, it advantageously contains a selectable marker that is different from the selectable marker used in the retroviral vector, to allow selection of transfected cells. Once again, suitably transfected cells can be selected and then cloned by limiting dilution.

Upon selection of suitable clones, the cells can be placed in a suitable medium and cultured to produce the desired protein of interest. The medium can contain serum or, preferably, be serum-free. In addition, cell longevity and protein production also can be increased by adding one or more caspase inhibitors (e.g., caspase 1 or 3) to the culture medium. Preferably the caspase inhibitor acts to inhibit one or more of caspase 3, caspase 9 and/or caspase 12. A cell-penetrating caspase inhibitor advantageously is used, and a pan-caspase inhibitor is particularly advantageous. Suitable inhibitors such as Z-VAD-fmk and Ac-DEVD-cho (SEQ ID NO: 7) are well known in the art. Alternatively, the cell line can be further transfected to express a caspase inhibitor, such as Aven or XIAP, to enhance its growth properties by affecting apoptosis. In this regard, certain members of the cytokine type I superfamily, such as EPO, can also increase cell survival by having anti-apoptotic and cytoprotective actions.

The methods described above generate a cell line that can be used for transfection with essentially any desired gene. However, the skilled artisan will recognize that established cell lines that constitutively express a desired protein, and particularly a recombinant protein, can be subsequently transfected with a suitable vector encoding the viral or Bcl-2 family anti-apoptosis genes. See Example 2 below.

The protein of interest can be essentially any protein that can be produced in detectable quantities in the host cell. Examples include traditional IgG type antibodies, Fab', Fab, F(ab')$_2$ or F(ab)$_2$ fragments, scFv, diabody, IgG-scFv or Fab-scFv fusion antibodies, IgG- or Fab-peptide toxin fusion proteins, or vaccines [e.g., including not limited to, Hepatitis A, B or C; HIV, influenza viruses, respiratory syncytial virus, papilloma viruses, Herpes viruses, Hantaan virus, Ebola viruses, Rota virus, Cytomegalovirus, Leishmania RNA viruses, SARS, malaria, tuberculosis (Mycobacteria), Anthrax, Smallpox, Tularemia, and others listed in www.vaccines.org, incorporated herein by reference in its entirety]. The host cells described herein are particularly suitable for highly efficient production of antibodies and antibody fragments in myeloma cell lines as described in Examples 1 and 2, as well as recombinant growth factors (e.g., EPO, G-CSF, GM-CSF, EGF, VEGF, thrombopoietin), hormones, interleukins (e.g., IL-1 through IL-31), interferons (e.g., alpha, beta, gamma, and consensus), and enzymes. These methods could be applied to any number of cell lines that are used for production of recombinant proteins, including other myeloma cell lines, such as murine NSO or rat YB2/0; epithelial lines, such as CHO and HEK 293; mesenchymal cell lines, such as fibroblast lines COS-1 or COS-7; and neuronal cells, such as retinal cells, as well as glial and glioma cells.

Recombinant Antibody Expression in Cells Expressing Apoptosis Inhibitors

Prior work has described the effects of co-expressing Bcl-2, a naturally occurring apoptosis inhibitor, in recombinant CHO cells producing a chimeric antibody. (See Tey et al., Biotechnol. Bioeng. 68:31-43 (2000).) Although increased cell culture life was observed, antibody production did not increase over equivalent cells that lacked Bcl-2 expression. However, the present inventors have found that production of recombinant antibody from myeloma cells is significantly increased when the cells also express Bcl-2.

Advantageously, the myeloma cell line is stably transfected with an expression cassette encoding the antibody or antibody fragment. A suitable expression cassette contains one or more promoters that controls expression of the antibody heavy and light chains (of single chain in the case of an scFv) together with a selectable marker as described above. A particularly useful vector is pdHL2, which contains a selectable marker gene comprising a promoter operatively linked to a DNA sequence encoding a selectable marker enzyme; a transcription unit having a promoter operatively linked to a DNA sequence encoding the protein of interest; an enhancer element between the selectable marker gene and the transcription unit, which stimulates transcription of both the selectable marker gene and the first transcription unit compared to the transcription of both the selectable marker gene and the first transcription unit in the absence of the first enhancer.

The vector also contains a blocking element composed of a promoter placed between the first enhancer and the selectable marker gene, which is potentially useful for selectively attenuating the stimulation of transcription of the selectable marker gene. $V_H$ and $V_L$ sequences can be ligated into pdHL2, which is an amplifiable vector containing sequences for the human light chain constant region, the heavy chain constant region, and an amplifiable dhfr gene, each controlled by separate promoters. See Leung et al., Tumor Targeting 2:184, (1996) and Losman et al., Cancer 80:2660-2667, (1997). This vector can be transfected into cells by, for example, electroporation. Selection can be performed by the addition of 0.1 µM or a suitable concentration of methotrexate (MTX) into the culture media. Amplification can be carried out in a stepwise fashion with increasing concentration of MTX, up to 3 µM or higher. Cells stably transfected with the expression cassette and that constitutively express the antibody of interest can therefore be obtained and characterized using methods that are well known in the art. See also Example 4, below. After selection and cloning, the antibody-expressing cell line can then be transfected with an expression vector that encodes an anti-apoptosis gene, such as Bcl-2. For example, the vector pZeoSV (Invitrogen, Carlsbad, Calif.) containing the Bcl-2 gene fused to an SV40 promoter is transfected into the cell using a suitable method such as electroporation, and selection and gene amplification can be carried out if necessary.

Alternatively, a suitable host cell may be transfected with an apoptosis inhibitor, such as a mutant Bcl-2 gene, then adapted for growth in serum-free medium prior to further transfection, preferably in serum-free medium, with an expression vector encoding a desired protein of interest. Antibody production using the resulting cell line can be carried out as above and compared to production in cells that do not express an apoptosis inhibitor.

Representative examples to illustrate the present invention are given below. Example 1 describes that the incorporation of HPV-16 E6/E7 into Sp2/0 cell leads to an improved cell clone, Sp-E26, showing characteristics of reduced/delayed apoptosis. Example 2 describes a method to improve host cell lines by over-expression of the HPV-16 E7 element alone. Example 3 describes using Sp-E26 as a host to develop transfectants producing a recombinant Ab. Example 4 describes the enhanced production of Mab observed for an antibody-producing cell line that co-expresses the E6/E7 element. Example 5 describes the generation and characterization of a modified Sp2/0 cell line (designated Sp-EEE) that constitutively expresses a mutant Bcl-2 (Bcl-2-EEE) possessing three point mutations, resulting in improved longevity. Example 6 describes the improved growth properties of an antibody-producing cell line that expresses Bcl-2. Example 7 describes the enhanced production of MAb observed for the Bcl-2 expressing cell line of Example 6. Example 8 describes the methods to improve a cell clone producing low-level recombinant protein by introduction of Bcl-2 expression in the cell. Example 9 describes the methods to improve Sp-E26 by introduction of Bcl-2 expression in the cell. Example 10 describes the use of Sp-EEE as a host to develop transfectants producing a recombinant Ab. Example 11 describes the use of fed-batch reactor profiles and feeding schedules to optimize yield. Example 12 describes the generation of a subclone of Sp-EEE capable of growth as well as transfection in serum-free media.

While preferred embodiments are illustrated herein by way of cell lines transfected with one or more genes encoding inhibitors of apoptosis known in the art, the skilled artisan will realize that in alternative embodiments, various substitutions, deletions or insertions may be made in the coding and/or non-coding sequence of such genes within the scope of the claimed methods and compositions, so long as the encoded protein exhibits the same physiological function (anti-apoptosis) as the native protein. In certain embodiments, the encoded protein(s) may exhibit 80% or greater sequence identity with the native (wild-type) protein, more preferably 85% or greater, more preferably 90% or greater, more preferably 95% or greater, more preferably 98% or greater, more preferably 99% or greater, most preferably 99.5% or greater sequence identity.

Antibodies

Various embodiments may concern antibodies and/or antibody fragments expressed from the transfected cell lines of interest. The term "antibody" is used herein to refer to any antibody-like molecule that has an antigen binding region, and includes antibody fragments such as Fab', Fab, F(ab')$_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Harlowe and Lane, 1988, *Antibodies: A Laboratory Manual*, Cold Spring Harbor Laboratory). Antibodies of use may also be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and are available for use in the claimed methods and compositions. (See, for example, U.S. Pat. Nos. 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 8,783,758; 6,770,450; 6,767,711; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,274; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459 each incorporated herein by reference with respect to the ATCC deposit number for the antibody-secreting hybridoma cell lines and the associated target antigens for the antibodies or fragments thereof.) These are exemplary only and a wide variety of other antibody-secreting hybridomas are known in the art. The skilled artisan will realize that antibody-secreting hybridomas against almost any disease-associated antigen may be obtained by a simple search of the ATCC, PubMed and/or USPTO databases for antibodies against a selected disease-associated target of interest. The antigen binding domains of the cloned antibodies may be amplified, excised, ligated into an expression vector, transformed into an adapted host cell and used for protein production, using standard techniques well known in the art.

Production of Antibody Fragments

Some embodiments of the claimed methods and/or compositions may concern antibody fragments. Exemplary methods for producing antibody fragments are disclosed in U.S. Pat. Nos. 4,036,945; 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of forming antibody fragments, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or crosslinked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell. The recombinant host cells synthesize a single polypeptide chain with a linker peptide bridging the two V domains. Methods for producing sFv's are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.). Where an antibody-secreting hybridoma cell line is publicly available, the CDR sequences encoding antigen-binding specificity may be obtained, incorporated into chimeric or humanized antibodies, and used.

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immunol., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990).

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the µ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods, as known in the art. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols. A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Such human antibodies may be coupled to other molecules by chemical cross-linking or other known methodologies. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

EXAMPLES

Example 1

Figure 1:
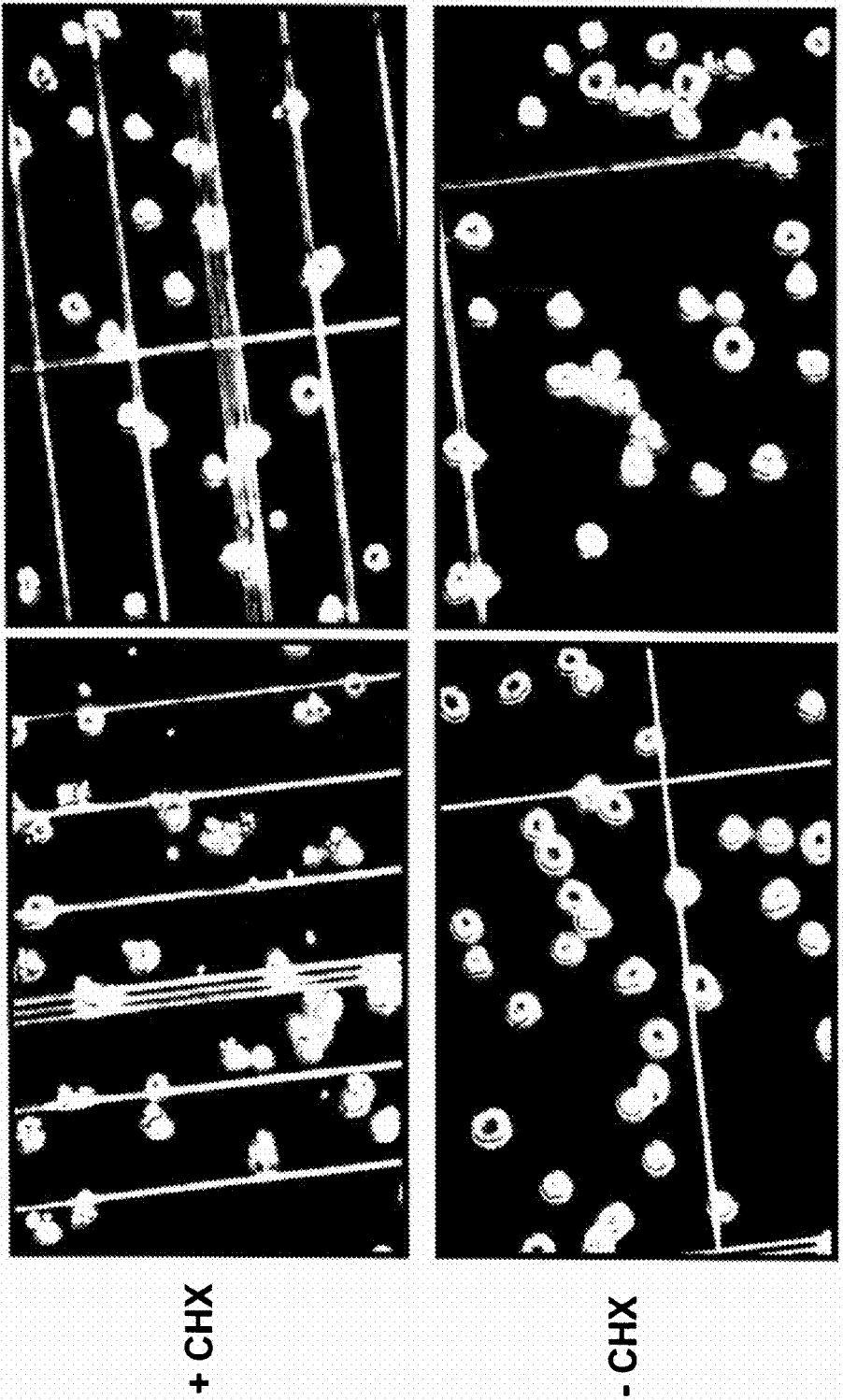

Generation of Apoptosis-Resistance Cell Clones by Stable Expression of HPV-16 E6 and E7 Genes Selection of Cell Clones Resistant to CHX Treatment Sp2/0 cells were transduced with an LXSN retroviral vector containing the expression cassette of HPV-16 E6 and E7 genes at an MOI (multiple of infection) of 10:1. After recovery for 24 h, the infected cells were selected in G418 (1000 µg/ml) for 10 days. G418-resistant cells were cloned in 96-well cell culture plates by limiting dilution (0.5 cells/well). Stable infectants were screened for resistance to treatment by cycloheximide (CHX), a potent apoptosis-inducing agent. Briefly, healthy cells (viability>95%, FIGS. 1C and D) were incubated in medium containing 25 µg/ml of CHX and cell morphology was examined under a microscope. While more than 50% of parent Sp2/0 cells underwent morphology change after two to three hours of incubation and became fragmented (FIG. 1A), several E6/E7 transfected clones showed less extent of morphology change, indicating resistance to apoptosis. The best clone, designated as Sp-E26, showed no apparent morphology change upon four hours of treatment (FIG. 1B).

Figure 2:
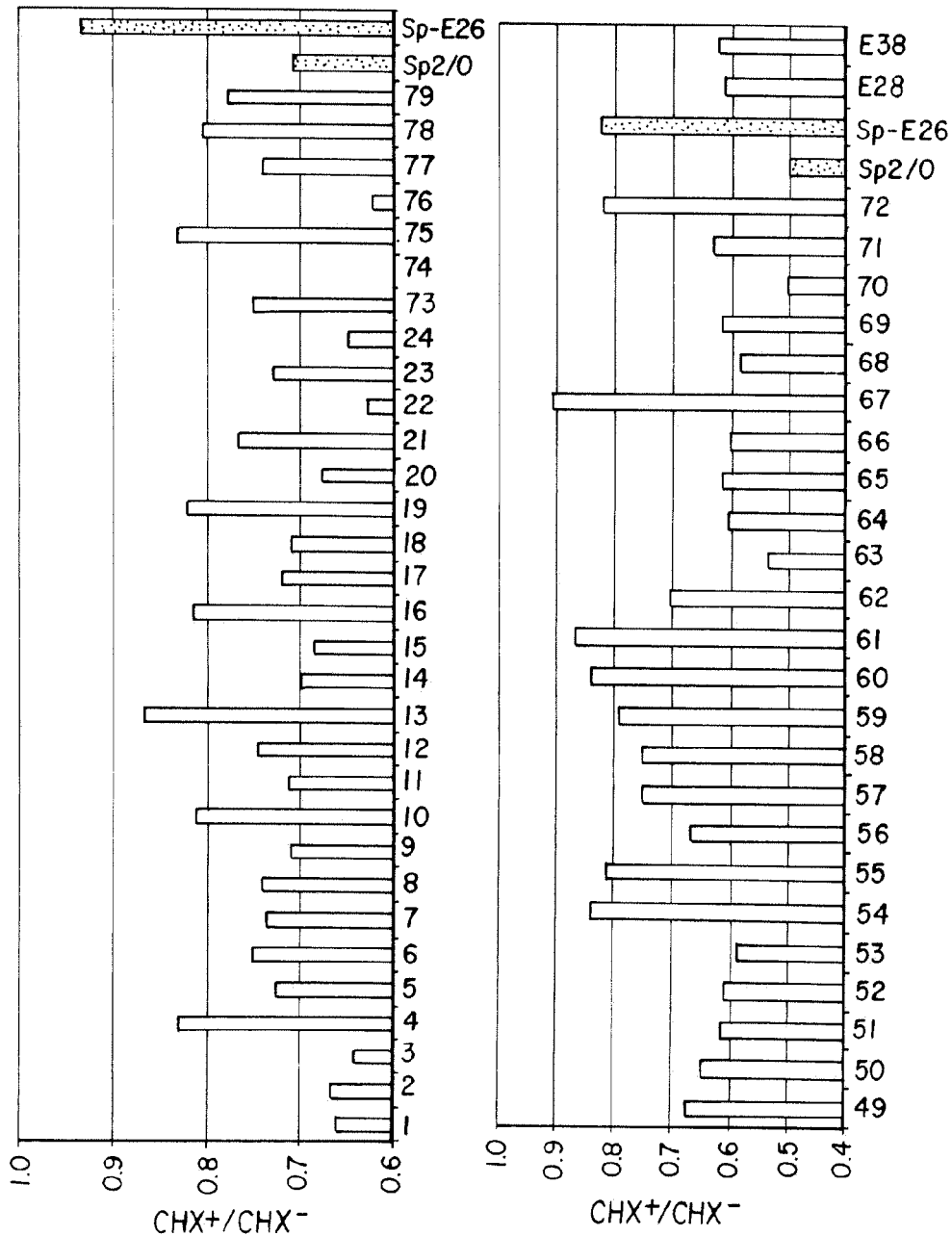

To avoid tedious visual examination, the MTT assay was used to access the changes in viable cell population. After the healthy cells were incubated with or without CHX under normal culture condition for 2-3 h, MTT dye was added to the wells. After further incubation for two hours, the cells were solubilized by adding a lysis buffer contain SDS and HCl. The plates were incubated overnight at 37° C. and OD reading was performed at 590 nm using an ELISA plate reader. As shown in FIG. 2, the viable cell population was significantly reduced when Sp2/0 cells were treated with CHX. By comparison, under the same treatment conditions (concentration of CHX and length of time), Sp-E26 cells tolerated better against CHX treatment. With this method, a large number of clones can be screened and selected for further analyses (FIG. 2).

Anti-Apoptosis Property of Sp-E26

Figure 3:
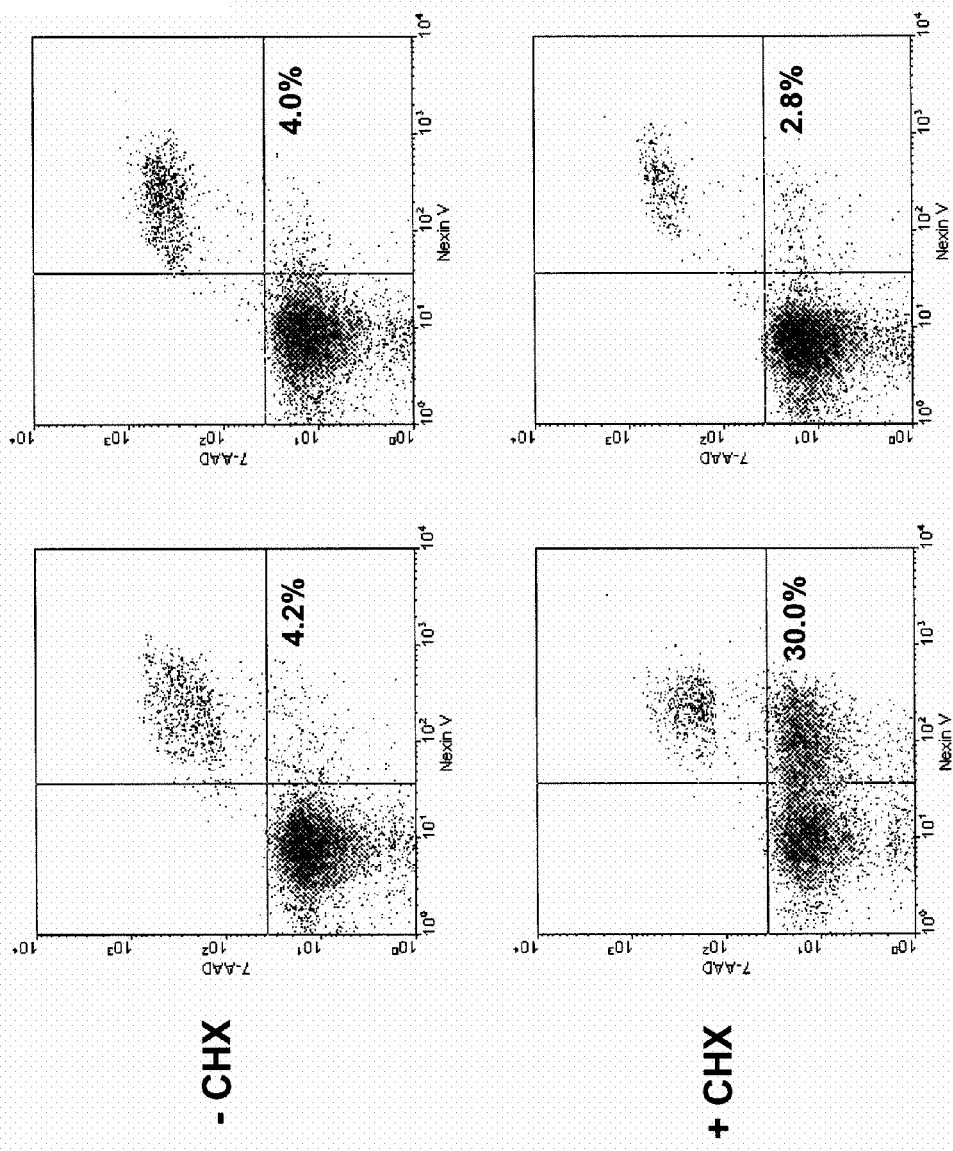
FIG. 3 shows the dot plots of Guava Nexin V assay. The percentage of early apoptotic cells (Nexin V-positive and 7-AAD-negative) is indicated in the lower-right quadrant.

CHX-induced apoptosis in Sp-E26 and the parent Sp2/0 cells was evaluated by Annexin V staining and DNA fragmentation assay. After being incubated in the medium containing 25 µg/ml of CHX, the cells were harvested and stained with Guava Nexin reagent (equivalent of Annexin V staining) and analyzed in a Guava Personal Cell Analysis system (Guava Technologies, Inc.). FIG. 3 shows that while more than 30% of Sp2/0 cells became Annexin V positive when exposed to CHX treatment for about 1.5 h, indicating apoptosis, while Sp-E26 remained healthy, showing no increase in early apoptotic cells.

Figure 4:
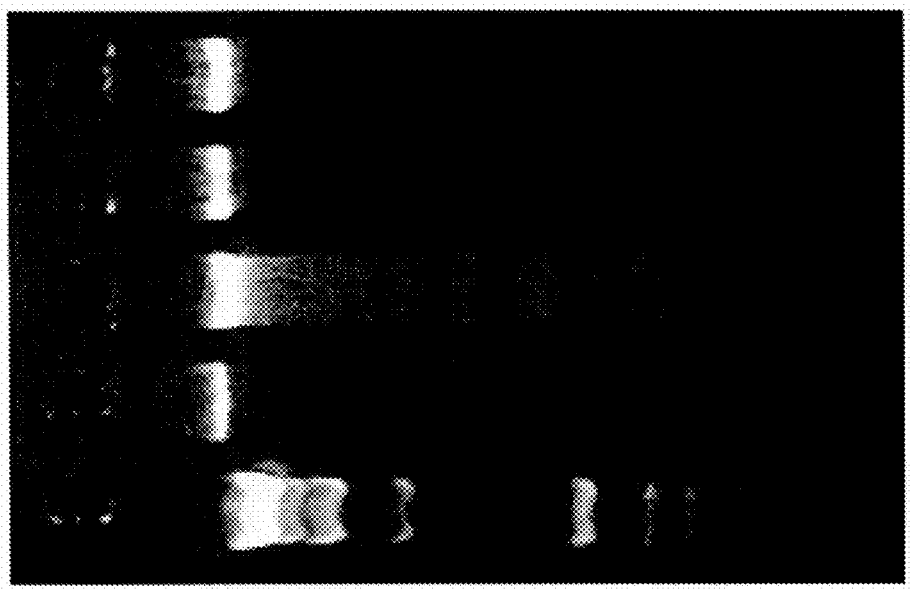
FIG. 4 shows the DNA fragmentation in Sp2/0 treated by CHX. In contrast, Sp-E26 cells are resistant to the treatment.

The induction of apoptosis by CHX can be revealed by analysis of the formation of intracellular oligonucleosomal DNA fragments, a hallmark of apoptosis. The cellular DNA was extracted from CHX-treated and untreated Sp-E26 and Sp2/0 cells and DNA laddering assay was performed. In Sp2/0 cells treated with CHX, extensive DNA fragmentation was detected (FIG. 4). In contrast, under identical treatment conditions, the genomic DNA of Sp-E26 was still intact, showing no appearance of DNA fragmentation (FIG. 4).

Presence of HPV E6 and E7 Genes in Sp-E26 Cells

To confirm that E6 and E7 genes are stably present in the genome of Sp-E26 cells, oligonucleotide primers specific for E6 and E7 genes were designed and used in a PCR reaction with the genomic DNA extracted from Sp-E26 as the template, resulting in an about 700 bp DNA fragment. The PCR product was cloned and confirmed to be E6 and E7 genes by DNA sequencing. No E6 and E7 genes were detected in the parent Sp2/0 cells.

Improved Growth Properties of Sp-E26

The growth properties of Sp-E26 were evaluated in T-flask (FIG. 5) and 3L-batch bioreactor (FIG. 6). Sp-E26 showed improved growth properties over the parent Sp2/0 cell in batch cultures, achieving higher maximum cell density and longer survival time.

Example 2

Generation of Apoptosis-Resistance Cell Clones by Stable Over-Expression of HPV16 E7 Gene The structure of the poly-cistronic HPV 16 E6 and E7 genes integrated into the genome of clone Sp-E26 was analyzed by PCR using the primer pair E6-N8$^+$ (ATGTTTCAG-GACCCACAGGAGCGA; SEQ ID NO: 8) and E7-C8$^-$ (TTATGGTTTCTGAGA ACAGATGGG; SEQ ID NO: 9) and DNA sequencing. Since the sequences of primer E6-N8$^+$ and E7-C8$^-$ match with the coding sequence for the N-terminal 8 amino acid residues of E6 and the complementary sequence for the C-terminal 8 codons of E7, respectively, the amplicon of full-length E6 and E7 is expected to be about 850 bp. However, amplification of the genomic DNA prepared from Sp-E26 cell with E6-N8$^+$ and E7-C8$^-$ resulted a PCR fragment of only about 700 bp. DNA sequencing of the 700 by PCR product revealed a deletion of a 182 poly-nucleotide fragment from the E6 gene. The defective E6 gene likely resulted from splicing and encodes a truncated E6 peptide with N-terminal 43 amino acid residues. Considering the major physiological activity attributed to E6 is its ability to down-regulate p53 expression, the truncated E6 protein is probably not fully functional because the level of p53 expression in Sp-E26 was found to be more stable than that in Sp2/0.

Thus, to evaluate whether HPV-16 E7 gene alone is sufficient to have anti-apoptotic effect and to improve the growth properties of Sp2/0 cells, transfection of Sp2/0 cell with HPV-16 E7 is performed as follows:

(i) The DNA sequence encoding E7 is cloned from Sp-E26 cell by RT-PCR. Proper restriction sites are introduced to facilitate the ligation of the gene into a mammalian expression vector, pRc/CMV (Invitrogen). Transcription of the viral gene within the vector, designated as E7pRc, is directed from CMV promoter-enhancer sequences. The vector also contains a gene conferring neomycin resistance, which is transcribed from the SV40 promoter.

(ii) Sp2/0 cells are transfected with the expression vector containing the expression cassette of HPV-16 E7 gene. Briefly, 5 µg of E7pRc is linearized by Seal and transfected into the cell by electroporation.

(iii) After recovery for 24 hours, the transfected cells are selected in G418 (1000 µg/ml) for 10 days.

(iv) G418-resistant cells are then cloned in 96-well cell culture plates by limiting dilution (0.5 cells/well). Stable transfectants are selected and screened for resistance to treatment by cycloheximide (CHX), a potent apoptosis-inducing agent.

(v) Healthy cells (viability >95%) are incubated in medium containing 25 µg/ml of CHX or in the absence of CHX for 3-4 hours under normal culture conditions, followed by the addition of MTT dye into the wells. After further incubation for two hours, the cells are solubilized by adding a lysis buffer contain SDS and HCl. The plates are incubated overnight at 37° C. and an OD reading is performed at 590 nm using an ELISA plate reader. Cell clones showing resistance to CHX treatment are selected and expanded for further analyses.

(vi) The anti-apoptosis property of E7-transfected cells is evaluated by Annexin V staining and DNA fragmentation assays. In the Annexin V assay, after being incubated in the medium containing 25 µg/ml of CHX, the cells are harvested and stained with Guava Nexin reagent (equivalent of Annexin V staining) and analyzed in a Guava Personal Cell Analysis system (Guava Technologies, Inc.). In the DNA fragmentation assay, the cellular DNA is extracted from CHX-treated and untreated E7-transfectants and Sp2/0 cells and analyzed with agarose gel electrophoresis.

(vii) Expression of the viral oncogene in E7-transfectants is evaluated by Southern blot (genomic level), Northern blot (mRNA level), and immunoblot (protein level) analysis. Expression of intracellular proteins that are involved in apoptosis processes and affected by E7 protein are examined by immunoblotting analyses.

(viii) The growth properties of selected E7-transfectants are evaluated in T-flask and in a 3 L-batch bioreactor. The transfectants show improved growth properties, i.e. achieving higher maximum cell density and longer survival time, over the parent Sp2/0 cell in batch cultures are considered to be better host cells.

Example 3

High-Level Expression of hLL2 IgG in Sp-E26

In this example, Sp-E26 is used as a host to generate cell clones producing hLL2, a humanized anti-CD22 Ab developed for treating patients with NHL and autoimmune diseases. An hLL2-producing clone, 87-2-C9, was previously generated by using Sp2/0 cell as a host (Losman et al., Cancer 80, 2660-2666, 1997), in which case, only one positive clone (a frequency of about $2.5 \times 10^{-7}$) was identified after transfection, and the maximum productivity ($P_{max}$), defined as the concentration of the antibody in conditioned terminal culture medium in T-flask, of the only hLL2-producing clone, before amplification, was 1.4 mg/L. Transfection of Sp-E26 cell with the same hLL2pdHL2 vector and by using similar procedures as described by Losman et al. (Cancer 80, 2660-2666, 1997) resulted in more than 200 stable hLL2-producing clones, a frequency of >$10^4$). The $P_{max}$ of 12 randomly selected clones was evaluated and found to be between 13 and 170 mg/L, with a mean of 50 mg/L. The productivities of these clones can be further enhanced by gene amplification with MTX. This example demonstrated the advantage of using Sp-E26 over its parent Sp2/0 cell as a host for the development of cell clones producing recombinant proteins.

Example 4

Improvement of Ab-Producing Cell Lines by Stable Expression of HPV16 E6 and E7 Genes 607-3u-8 cells were originally generated from Sp2/0 by transfection to produce a humanized monoclonal Ab. The clone was developed by gene amplification (with MTX) and subcloning to enhance the maximum (Ab) productivity up to 150 mg/L, which decreased to about 100 mg/L following weaning off serum supplement in the culture medium. To obtain higher antibody productivity under serum-free conditions, E6/E7 genes of HPV-16 were introduced into 607-3u-8 and the effect of E6/E7 on Ab-productivity was evaluated as follows.

607-3u-8 cells maintained in HSFM supplemented with 10% FBS and 3 µM MTX were transduced with an LXSN retroviral vector containing the expression cassette of HPV-16 E6 and E7 genes at an MOI of 10:1. After recovery for 24 h, stably transfected cells were selected in G418 (400 µg/ml) for 10 days. G418-resistant cells were subcloned in 96-well cell culture plates by limiting dilution (0.5 cells/well). A surviving clone, designated as 607E1C12, was obtained for evaluation. Two subclones, designated as 607-3u-8-7G7 and 607-3u-8-2D10, of 607-3u-8 without E6/E7 transfection were also selected. The $P_{max}$ of these three clones were determined and there were no significant difference (Table 1).

These results suggest that introducing E6/E7 genes into the cell does not alter the ability of cells producing Ab. Next, 607E1C12, 607-3u-8-7G7 and 607-3u-8-2D10 were adapted to grow in serum-free medium and the productivities of these clones were determined. All cells were growing well in serum-free medium. The final antibody productivity of clone 607E1C12 was maintained at 150 mg/L, while the two clones without E6/E7 were substantially reduced. In addition, the productivity of 607E1C12 was stable after a freeze (for cryopreservation) and thaw cycle (Table 1).

TABLE 1

The productivities of Ab-producing clones

| Clone | $P_{max}(mg/L)^a$ | |
|---|---|---|
| | With serum | Serum-free |
| 607-3u-8-7G7 | 127 ± 16 (3)$^b$ | 74 ± 10 (4) |
| 607-3u-8-2D10 | 140 ± 4 (3) | 35 ± 2 (2) |
| 607E1C12 | 154 (1) | 142 ± 13 (6) |
| 607E1C12 (Cryo)$^c$ | | 145 ± 17 (5) |

$^a$Determined by protein purification of IgG from terminal culture supernatants.
$^b$The number in parenthesis indicates the sample size.
$^c$Cells had been frozen for cryopreservation.

Example 5

Generation and Characterization of a Genetically Modified Sp2/0 Cell Line that Constitutively Expresses a Mutant Bcl-2

Evidence suggests that a mutant Bcl-2 possessing three point mutations (T69E, S70E and S87E) exhibits significantly more anti-apoptotic activity compared to wild type or single point mutants (Deng et al., PNAS 101: 153-158, 2004). Thus, an expression vector for this triple mutant (designated as Bcl-2-EEE) was constructed and used to transfect Sp2/0 cells for increased survival and productivity, particularly in bioreactors. Clones were isolated and evaluated for Bcl-2-EEE expression level, growth and apoptotic properties. The nucleic acid sequence for the Bcl-2-EEE is depicted as SEQ ID NO. 3; the corresponding amino acid sequence for the Bcl-2-EEE protein is depicted as SEQ ID NO. 4.

A 116 bp synthetic DNA duplex was designed based on the coding sequence for amino acid residues 64-101 of human Bcl-2. The codons for residues 69, 70 and 87 were all changed to those for glutamic acid (E). The entire sequence was extraordinarily GC rich and had numerous poly G and poly C runs. Conservative changes were made to several codons to break up the G and C runs and decrease the overall GC content.

Two 80-mer oligonucleotides were synthesized that, combined, span the 116 bp sequence and overlap on their 3' ends with 22 bp (See SEQ ID NOs. 5 and 6). The oligonucleotides were annealed and duplex DNA was generated by primer extension with Taq DNA polymerase. The duplex was amplified using the PCR primers, Bcl-2-EEE PCR Left (TATATG-GACCCGGTCGCCAGAGAAG; SEQ ID NO: 10), and Bcl-2-EEE PCR Right (TTAATCGCCGGCCTGGCGGAGGGTC; SEQ ID NO: 11).

The 126 bp amplimer was then cloned into pGemT PCR cloning vector. The Bcl-2-EEE-pGemT construct was digested with TthI and NgoMI restriction endonucleases and the 105 by fragment was gel isolated and ligated with hBcl-2-puc19 vector (ATCC 79804) that was digested with TthI and NgoMI to generate hBcl-2(EEE)-puc19. The sequence of this construct was confirmed.

A 948 bp insert fragment was excised from hBcl-2 (EEE)-puc19 with EcoRI and ligated with pZeoSV2+ vector that was digested with EcoRI and treated with alkaline phosphatase. The resulting construct is hBcl-2 (EEE)-pZeoSV2+.

Sp2/0 cells (5.6×10$^6$) were then transfected by electroporation with 60 µg of hBcl-2 (EEE)-pZeoSV2+ following the standard protocol for Sp2/0 cells. The cells were plated into six 96-well plates that were incubated without selection for 48 hours. After two days, 800 µg/ml of zeocin was added to the media.

Cells from 40 wells were expanded to 24-well plates and analyzed by western blot with anti-hBcl-2 and anti-beta actin. All but 5 of the 40 showed medium to high levels of Bcl-2-EEE expression. The results for one of four gels are shown in FIG. 7. An Sp2/0 derived hMN 14 cell line (Clone 664.B4) that was previously transfected with wild type Bcl-2 was used as a positive control (+). As was demonstrated by Deng et al., the Bcl-2-EEE migrates slightly slower than wild type Bcl-2 in SDS-PAGE.

Three strongly positive wells (#7, #25 and #87) were chosen for further evaluation and sub-cloning. Limiting dilution plating resulted in <20 positive wells per 96-well plate, indicating a very high probability (>99%) that the cells in individual wells are in fact cloned. Initially, 23 subclones from the three original wells were analyzed by Guava Express using anti-hBcl-2-PE (FIG. 8). The results confirmed that the original wells contained mixed cell clones. Well #7 yielded clones with the strongest signal and well #25 had those with the lowest. Clones 7-12, 7-16, 87-2 and 87-10 were expanded for further analysis. Subsequently, some initially slower growing subclones were similarly analyzed and one clone, 87-29, gave a signal that was 20% higher than any other clone and was expanded for further analysis.

Two high expressing SP-EEE clones (87-29 and 7-16) were compared to the untransfected Sp2/0, Raji and Daudi cells (FIG. 9). The Sp-EEE clones expresses about 20-fold higher than Raji and Daudi cells, which are both known to express Bcl-2 at presumably normal cell levels. Sp2/0 cells were negative. This was further verified by anti-Bcl-2 immunoblot (FIG. 10). Bcl-2 was not detected with a human Bcl-2 specific antibody in Sp2/0 cells even with high protein loading (50K cells) and long exposure of X-ray film. Immunoblot analysis with an anti-Bcl-2 MAb (C-2, Santa Cruz Biotech.) that recognizes mouse, rat and human Bcl-2 did not detect any Bcl-2 from untransfected Sp2/0 cells, even with high protein loading (100K cells) and long exposure time (FIG. 10B). If there is any Bcl-2 expressed in Sp2/0 cells, it is at a level that is more than 2 orders of magnitude less than the Bcl-2-EEE in clone 87-29.

Growth curves were compared for five Sp-EEE subclones and Sp2/0 cells. Three Sp-EEE subclones displayed a clear advantage over Sp2/0 cells. These three (7-12, 7-16 and 87-29) also express the highest levels of Bcl-2-EEE. As 7-12 and 7-16 are from the same original well and have nearly identical properties (Bcl-2-EEE levels and growth curves), they likely originated from the same initial clone. The best two SP-EEE subclones 7-16 and 87-29 were used for further evaluation.

The clones were plated in media supplemented with 10%, 1% or 0% serum (without weaning) and cell density and viability were monitored. In 10% serum 87-29 grew to a high density and had more than 4 days increased survival compared to Sp2/0 cells (FIG. 11). In 1% serum, all cells grew to about 35-40% of the density achieved in 10% serum and the Bcl-2-EEE transfectants had a similar survival advantage over Sp2/0 (FIG. 12). When transferred directly into serum free media, the Sp2/0 cells only grew to 600K cells/ml while 87-29 cells grew to a two-fold higher density (FIG. 13). In each serum concentration 87-29 cells survived 4-6 days longer than Sp2/0 cells.

The methotrexate (MTX) sensitivity was determined for 87-29 (FIG. 14). The data suggests that a minimum MTX concentration of 0.04 µM is sufficient for initial selection of MTX-resistant clones. Therefore, the same selection and amplification protocols used for Sp2/0 cells can be employed with the SP-EEE cells.

Bcl-2 is a pro-survival/anti-apoptotic protein. It has been demonstrated by several groups that a Bcl-2 deletion mutant missing the flexible loop domain (FLD) has an enhanced ability to inhibit apoptotosis (Figueroa et al., 2001, Biotechnology and Bioengineering, 73, 211-222; Chang et al., 1997, EMBO J., 16, 968-977). More recently, it was demonstrated that mutation of 1 to 3 S/T residues in the FLD of Bcl-2 to glutamic acid, which mimics phosphorylation, significantly enhances its anti-apoptotic ability (Deng et al. 2004, PNAS, 101, 153-158). The triple mutant (T69E, S70E and S87E) provided the most significant survival enhancement. Here, a similar BcI-2 triple mutant construct (Bcl-2-EEE), was used to stably transfect Sp2/0 cells.

All the aforementioned experiments demonstrate that expression of Bcl-2-EEE reduces apoptosis rates in Sp2/0 cells. This effect was largely dose dependent, in that clones with higher expression levels survived longer than those with lower levels. The best clone, 87-29, grows to a 15-20% higher cell density and survives an additional 4-6 days compared to untransfected Sp2/0 cells.

The Bcl-2-EEE level in clone (87-29) is approximately 20-fold higher than normal levels in Daudi or Raji cells. No Bcl-2 expression was detected in untransfected Sp2/0 cells. As described in Example 6, hMN-14-expressing Sp2/0 cells were transfected with a similar construct for expression of wild type Bcl-2 and a clone with exceptional growth properties and enhanced productivity was isolated. When this clone (664.B4) was amplified further with MTX, the Bcl-2 levels increased significantly. Ultimately, the amplified (3 µM MTX) cell line was sub-cloned and the Bcl-2 level of one clone (664.B4.1C1) was two-fold higher than 664.B4. This particular subclone has superior productivity and growth properties. The Bcl-2-EEE level in 87-29 is approximately two-fold higher than the level of Bcl-2 in the amplified 664.B4.1C1. 87-29 cells have a growth rate that is comparable to that of Sp2/0 cells and can apparently continue to grow for one additional day and reach a maximal density that is 15-20% higher than Sp2/0. A similar property was found for the E6/E7 expressing Sp-E26 cell line. The Bcl-2-EEE expressing 87-29 clone, which provides an additional 4-6 days survival over the parental Sp2/0 cells, is superior to the Sp-E26 clone, which only survives one additional day.

The Sp-EEE cell line as represented by the 87-29 clone is useful as an apoptosis-resistant host for expressing a recombinant protein upon transfection with a suitable vector containing the gene for that recombinant protein. In order for this cell line to be useful it must maintain its Bcl-2-EEE expression and survival advantage following transfection and amplification and during extended culture. It is unlikely that the stably transfected Bcl-2-EEE gene will be lost during subsequent transfection and therefore the survival properties should not diminish. It is possible that MTX amplification could even improve the survival of producing clones via increasing expression of Bcl-2 proteins. Indeed, this was the case with the hMN-14 664.B4 cell line, which was transfected with wild type BcI-2. Following amplification and sub-cloning, the Bcl-2 level increased several fold and cell survival improved significantly.

The final Sp/EEE clone (#87-29) has a growth rate that is comparable to the parental Sp2/0 cells. However, the Sp/EEE 87-29 cells continue to grow for one additional day, reach a maximal density that is 15-20% greater and display an additional 4-6 days survival compared to Sp2/0. Further, the Sp/EEE cell line was considerably more tolerant to serum deprivation compared to Sp2/0 cells.

Example 6

Improvement of Ab-Producing Cell Survival in Stationary Batch Culture by Stable Expression of a Human Bcl-2 Gene Generation of a Bcl-2-Transfected Cell Clone A cell clone 665.2B9 was originally generated from Sp2/0 by transfection to produce a humanized monoclonal anti-CEA Ab (Qu et al., unpublished results). A vector, designated hMN14pdHL2, was used to transfect Sp2/0 cells to obtain the cell clone 665.2B9. The pdHL2 vector was first described by Gillies et al., and had an amplifiable murine dhfr gene that allows subsequent selection and amplification by methotrexate treatment (Gillies et al., J. Immunol. Methods 125:191 (1989)). Generally, the pdHL2 vector provides expression of both IgG heavy and light chain genes that are independently controlled by two metallothionine promoters and IgH enhancers. A diagram of the hMN14pdHL2 vector is shown in FIG. 16. SEQ ID NO. 1 shows the sequence of the vector; SEQ ID NO. 2 shows the 72 bp sequence defined as the enhancer sequence; the promoter sequence corresponds to nt2908-2979 of hMN14pdHL2.

Sp2/0 cells can be generally transfected by electroporation with linearized pdHL2 vectors such as the hMN14pdHL2 vector used in this instance. Selection can be initiated 48 hours after transfection by incubating cells with medium containing 0.05 to 0.1 µM. MTX. Amplification of inserted antibody sequences is achieved by a stepwise increase in MTX concentration up to 5 µM.

The clone was subjected to gene amplification with MTX increased stepwise to 0.3 at which point the maximum productivity (Pmax) of the antibody was increased to about 100 mg/L. To improve cell growth properties, 665.2B9 cells were transfected with a plasmid expression vector (FIG. 17) containing the human Bcl-2 gene by electroporation. Bcl-2 gene was excised from pB4 plasmid purchased from ATCC (pB4, catalog #79804) using EcoRI sites and inserted into MCS of mammalian expression vector pZeoSV(+) using the same restriction enzyme. Since zeocin resistance gene is part of the vector, transfected cells were placed into medium containing zeocin ranging from 50-300 µg/mL. Stable clones were selected from media containing 300 mg/ml zeocin and subcloned in media without zeocin by plating into 96-well plates at a density of 0.5 cell/100 uL/well. The media without zeocin was used thereafter.

Formation of clones in wells was confirmed by visual observation under a microscope. Cells from the wells with only 1 cluster of cells were expanded. Each 96-well plate produced around 30 clones, from which 14 clones were randomly selected for further studies. The growth characteristics of these clones were evaluated by daily cell counting and viability measurements with ViaCount reagent and Guava PCA. From the 14 clones evaluated in 24-well plates (FIGS. 18, 19), one Bcl-2-transfected clone showing improved growth characteristics (higher cell densities and prolonged cell survival) was identified and designated as 665.2B9#4 (or clone #4). Comparing to the parent 665.2B9 clone, clone #4 grew to a higher cell density (about 1.7-fold) and survived 4 to 6 days longer in T-flasks (FIGS. 20, 21), and as a consequence of better growth, the P.sub.max of clone #4 was increased to about 170 mg/L as determined by ELISA titration and Protein A column purification.

Bcl-2 Expression in 665.2B9#4

To confirm that the improved growth properties of 665.2B9#4 were resulted from transfection of Bcl-2, intracellular level of human Bcl-2 protein was measured by using Guava Express reagent and Guava PCA instrument. Briefly, 4×10.sup.5 cells placed in 1.5 ml spin-tubes were centrifuged for 5 minutes at 1500 rpm, washed three times with 1×PBS. Supernatants were carefully aspirated. Fixation solution (10×, 60 µL) from Santa Cruz Biotechnology (SCB), Inc. (cat. # sc-3622) was added to cell pellets for 15 min and incubated on ice. Fixation solution was removed with 4×1 mL PBS at 4° C., each time spinning as described.

Permeabilization buffer (0.5 mL) at −20° C. (SCB cat. # sc-3623) was added dropwise while vortexing, followed by 15 min incubation on ice. Cells were then spun and washed two times with 0.5 mL FCM wash buffer (SCB cat. # sc-3624). Final cell pellet was resuspended in 100 µL of FCM wash buffer and stained for Bcl-2 intracellular protein with 10 µL of anti-Bcl-2 mouse monoclonal antibody conjugated to PE (obtained from SCB). Incubation was performed at room temperature in dark for one hour. Two washes with 0.5 mL of FCM wash buffer followed. The final cell pellet was resuspended with 0.4 mL FCM wash buffer and the cells analyzed on Guava PC. Mean values of the fluorescence intensity (MFI) for each clone were compared to control staining with non-specific, isotype mouse IgGI conjugated with PE. The results summarized in Table 2 confirm that clone 665.2B9#4 expresses a higher level of Bcl-2 protein compared to the parental cell line. A zeocin-resistant clone (#13) that showed a similar growth profile as the parent 665.2B9 was negative for Bcl-2 staining, confirming that Bcl-2 expression is necessary for the improvement of growth.

TABLE 2

Intracellular level of Bcl-2 determined by Guava Express.

| Cell | Viability[a] (%) | Mean FI (AU) |
|---|---|---|
| 665.2B9 | 84 | 42 |
| 665.2B9#4 | 97 | 110 |
| Clone#13 | 92 | 14 |
| Non-specific antibody staining | | 12 |

[a]Determined before the assay to ensure healthy cells were used.
[b]665.2B9 cells stained with an isotype-matched mouse IgG1 antibody, PE-conjugated.

With Guava Express analysis it was found that the intensities of fluorescent staining corresponding to Bcl-2 levels are rising with MTX amplification of clone 665.2B9#4, suggesting co-amplification of Bcl-2 with the dhfr gene. To compare intracellular Bcl-2 levels of amplified cells, Western blotting analysis was performed on cell lysates of clone 665.2B9#4 (Bcl-2 positive) and clone #13 (Bcl-2 negative) using an anti-human Bcl-2 antibody. Densitometric evaluation showed that Bcl-2 signal of clone 665.2B9#4 growing in 1.0 µM MTX is 2× stronger than the cells in 0.6 µM MTX. A lysate of Clone #13 did not reveal the presence of Bcl-2 protein (FIG. 22).

Example 7

Improved Ab-Production of Clone 665.2B9#4 under Batch Culture Condition

By monitoring nutrients consumption in the cell cultures near the terminal phase, it was found that glucose and L-glutamine are the first components to be consumed. Experiments were carried out to determine whether supplementation of these limiting nutrients would improve the final antibody yields. Two types of cultures were initiated: spiked fed batch—where these limiting components were supplemented upon their consumption; and unfed batch—without nutrients supplementation. Tested were Bcl-2-positive clone 665.2B9#4 growing in medium containing 0.6 and 1 µM of MTX and the Bcl-2-negative clone #13 growing in 0.3 µM MTX. FIGS. 23 and 24 show the profiles of cell viability and cell density in both culture types until they reached terminal stage. Protein yields, expressed as mg/L, are shown in Table 3. The results of this experiment suggest that nutrient spiking improves total yield of produced antibody about 2-fold for all cultures.

TABLE 3

Antibody production under batch culture conditions

| Cell/MTX (µM) | Unfed batch[a] (mg/L) | Spiked fed batch[a] (mg/L) |
|---|---|---|
| 665.2B9#4/0.6 | 117 | 286 |
| 665.2B9#4/1.0 | 156[b] | 296 |
| Clone#13/0.3 | 74.1 | 165 |

[a]Determined by Protein A column purification.
[b]Average of two purifications.

Example 8

Introduction of Bcl-2 Gene into a Cell Line Producing Low-Level of Recombinant Protein A cell clone 482.2C4A was originally generated from Sp2/0 by transfection to produce a bispecific Ab in the form of an IgG (anti-CEA) and two scFv (anti-DTPA) (Leung et al., J. Nuc. Med. 41: 270P, 2000; Hayes et al., Proc. Am. Asso. Cancer. Res. 43: 969, 2002), each of which is covalently linked to the C-terminus of the IgG heavy chain. The clone was subjected to gene amplification and had a final productivity of about 20 mg/L. To improve the growth property and eventually the Ab productivity, 482.2C4A cells were transfected with a plasmid expression vector containing the human Bcl-2 gene by electroporation as described in Example 6. The transfectants were selected in medium containing 750 µg/ml of Zeocin after three weeks.

Zeocin-resistant cells were treated with 25 µg/ml of CHX for 5 hours to eliminate apoptosis-sensitive cells. Treated cells were washed twice with fresh culture medium to remove CHX and resuspended in fresh growth medium. After recovering for 24 h, the viable cells were cloned into 96-well cell culture plates by limiting dilution (0.5 cells/well). Clones emerged in the wells in two weeks and were screened for Ab production, resistance to CHX-induced apoptosis, as well as growth profiles. Those clones performed better than the parent 482.2C4A in all aspects are selected and further characterized. The best performer is expected to be more robust when growing under stress condition, resist to aging-culture-condition induced apoptosis, and have a higher maximum Ab productivity (ca.150% or better) comparing to the parent 482.2C4A cell.

Example 9

Introduction of Bcl-2 Gene into Sp-E26 for a Further Improvement of Cell Growth Properties Sp-E26 cells are transfected with a plasmid expression vector containing the human Bcl-2-EEE gene, as described in Example 5, by electroporation. The transfectants are selected in medium containing 500 μg/ml of Zeocin after three weeks.

Zeocin-resistant cells are treated with 25 μg/ml of CHX for 5 hours to eliminate apoptosis-sensitive cells. Treated cells are washed twice with fresh culture medium to remove CHX and resuspended in fresh growth medium. After recovering for 24 h, the viable cells are cloned into 96-well cell culture plates by limiting dilution (0.5 cells/well). Clones emerge in the wells in two weeks and are screened for resistance to CHX-induced apoptosis, as well as growth profiles. Those clones perform better than the parent Sp-E26, as well as Sp-EEE, in all aspects are selected and further characterized. The best performer containing HPV-16 E6/E7 and Bcl-2-EEE is expected to be more robust when growing under stress condition and resistant to aging-culture-condition-induced apoptosis than the parent Sp-E26 and Sp/EEE cells; therefore, it is a better host cell for recombinant protein production.

Example 10

Improved Production of Recombinant Proteins with the Sp-EEE Cell Line

There are two paths that can be taken when developing a cell line with enhanced survival for production of recombinant proteins. One method, which has been accomplished quite successfully, as described in Example 6, involves stable transfection of an already producing cell line with a pro-survival gene, such as Bcl-2. However, this method requires additional transfection, selection and cloning steps, thereby lengthening the cell line development process by at least two months and possibly much more. Further, screening for the "best" clone is rather involved, since a number of parameters need to be determined for each clone, including growth/survival, Bcl-2 expression level and productivity. Thus, only a small number of clones can be evaluated. It is quite possible that clones with the highest productivity may not have superior survival and vice versa. An alternative strategy, employed here, is to develop a parental cell line with superior growth and survival properties, which is subsequently transfected with the expression vector for production of the desired protein.

Compared to Sp2/0 cells, the Sp-EEE cells continue to grow for one additional day, reach a maximal density that is 15-20% higher, and survive an additional 4-6 days in culture. The cells retain their enhanced growth and survival properties when subsequently transfected with genes for the production of recombinant proteins, such as IgG, antibody fragments and fusion proteins, growth factors, such as G-CSF, GM-CFS, EPO, EGF, VEGF, cytokines, such as an interleukin family member (IL-1-IL-31), or interferon family members (such as alpha, beta or gamma interferon), oligonucleotides, peptides, hormones, enzymes, or vaccines (e.g., Hepatitis A, B or C, as well as others described above).

A DNA vector, such as pdHL2, containing one or more expression cassettes for recombinant protein(s), such as an IgG, is used to transfect Sp-EEE cells by standard methods, such as electroporation. The transfectants are plated in 96-well plates and clones are analyzed for protein production by established techniques such as ELISA or Biacore. Productive clones are subjected to increasing concentrations of MTX in the culture media over several months to amplify the genetic copy number. Since the Bcl-2-EEE-expressing clones grow to about 20% higher cell density and survive at least an additional 4 days as compared to clones generated in Bcl-2 negative Sp2/0 cells, the former will produce at least 20% more recombinant protein in standard flask or roller bottle culture. An even greater increase is realized in suspension, perfusion or fed-batch bioreactor cultures.

Example 11

Improved Ab-Production of Bcl-2 Transfected Clone 665.B4.1C1 in Bioreactor

Both 665.2B9#4 and the parent clone 665.2B9 of Example 6 were weaned into serum-free media. The cells were adapted to a customized formulation of hybridoma serum-free medium (HSFM) (Immunomedics PN 10070) containing 3 μM MTX by continuous subculture in T-flasks for several months. The adapted cells were scaled up from T-flasks to roller bottles for banking. A master cell bank (MCB) for each cell line was created with $1 \times 10^7$ viable cells in each 1-mL vial using an FBS-free cryopreservation solution composed of 45% conditioned medium (medium that is collected as supernatant after centrifugation of a culture in the exponential growth phase), 10% DMSO and 45% HSFM. The MCB cell lines were designated 665.2B9.1E4 (without Bcl-2 gene) and 665.B4.1C1 (with Bcl-2 gene), respectively. The growth properties and antibody production of these two clones were compared under batch culture conditions.

Experiments were conducted in 3-L bench-scale bioreactors using the above cells expanded from the MCB. The 3-L bioreactor system is the scale-down model of a 2500-L cGMP bioreactor system. Therefore, the evaluation results would support the suitability of these cell lines for large-scale commercial manufacturing.

The same growth HSFM as that used in creating the MCB (Immunomedics PN 10070) was used to maintain the cell line and prepare the inoculum. Basal HSFM, a customized formulation based on the growth HSFM with customized modifications (Immunomedics PN 10194), was used in the 3-L fed-batch bioreactor process. Both media contain insulin and transferrin as the only trace proteins. Additional 0.1% Pluronic F68 was incorporated into the formulation to protect cells from shear caused by agitation and aeration. This media also contained 3 μM MTX.

The specific characteristics of the continuous feeding solutions and the pulse feeding solutions are shown in tables 4 and 5 as follows:

TABLE 4

Continuous feeding solutions

| Solutions | Formulation (Dissolve in WFI unless specified) |
|---|---|
| Glucose and glutamine solution (G/G) | Glucose, 13.3 g/L; Glutamine, 20 mM |
| ImmuC2 solution | Glucose, 13.3 g/L; Glutamine, 20 mM; PNS A, 50 ml/L; NaOH, 50 mM |
| ImmuC5 solution | Glucose, 26.6 g/L; Glutamine, 40 mM; PNS A, 100 ml/L.; NaOH, 100 mM |

TABLE 5

Pulse feeding Solutions

| Solutions | Formulation (Dissolve in WFI unless specified) |
|---|---|
| TC Soy Plus | 120 g/L |
| Linoleic acid/cyclodextrin | 1.5 mg/ml |
| HD lipid | 500X |
| β-mercaptoethanol/EDTA | BME, 0.01M; EDTA, 0.1 mM. |
| ImmuVitamin | MEM Vitamin Solution (100×), as solvent; Choline Chloride, 500 mg/L; Myo-inositol, 600 mg/L. |
| TEC solution | Transferrin solution (4 mg/mL), as solvent; CaCl2, 125 mM; Ethanolamine-HCl 1 g/L. |
| Insulin | 4 mg/ml |

The fed-batch experiments were conducted in 3 L Bellco spinner-flask bioreactor systems (Bellco glasses, Vineland, N.J.) with 2 L of working volume. The bioreactor temperature, pH and dissolved oxygen (DO) were monitored and controlled by single loop controllers. The reactor temperature was controlled at 37° C. by a heating blanket. The culture pH was controlled at 7.3 by the addition of $CO_2$ or 6% $Na_2CO_3$. Aeration was performed through a cylindrical sintered sparger at 10 ml/min. DO was controlled above 40% of air saturation by intermittent sparging of $O_2$ into the medium. A constant agitation rate of 50 about 60 rpm was used throughout the cultivation.

A frozen vial from MCB was thawed and recovered in T-flasks in approximately 1 to 2 weeks. The cells were then expanded from T-flasks to roller bottles prior to inoculation into the bioreactors. Cells were cultured at 37° C. in a 5% $CO_2$ atmosphere and maintained in the exponential growth phase throughout the expansion process.

Prior to the inoculation, 1.2 liters of Basal HSFM was pump-transferred into the bioreactor aseptically. The medium was air saturated to calibrate the dissolved oxygen (DO) probe. A medium sample was also taken to calibrate the pH probe. Once pH probes and DO probes were calibrated, both controllers were set to AUTO modes. Once the system reached set points of pH (7.3) and temperature (37° C.), calculated amount of inoculum from roller bottle was pump transferred into the bioreactor. The post-inoculation viable cell density (VCD) was around $2 \times 10^5$ vial cells/ml.

The feeding strategy is as follows. During the cultivation, concentrated nutrient solutions were fed into the bioreactor to provide the cells with necessary and non-excessive nutrients. Concentrated nutrient solutions were delivered to the culture via continuous feeding and pulse feeding. The continuous feeding solutions were pump transferred into the reactor continuously using peristaltic pumps (Watson-Marlow 101U/R). The pulse feeding solutions were pulse fed once a day into the culture.

Two fed-batch feeding strategies were developed and applied to both cell lines. Process #1 does not feed recombinant insulin during the cultivation. Process #2 is designed based on Process #1 with a modified linoleic acid and lipid feeding schedule and an additional feeding of insulin. The following tables summarize the feedings of both processes for both cell lines.

TABLE 6

Process #1 for cell line 665.2B9.1E4

Continuous feeding

| Day | Expected Viable Cell Density (cells/mL) | Continuous Feeding Rate (ml/day) | | |
|---|---|---|---|---|
| | | Glucose and Glutamine | ImmuC2 | ImmuC5 |
| Day 2 | 0.4~0.7E6 | 60 | 0 | 0 |
| Day 3 am | 1.0~1.7E6 | 0 | 60 | 0 |
| Day 3 pm | 1.01~2.5E6 | 0 | 90 | 0 |
| Day 4 am | 2.51~3.5E6 | 0 | 90 | 0 |
| Day 4 pm | 2.51~4.5E6 | 0 | 150 | 0 |
| Day 5 am | 4.51~6.5E6 | 0 | 0 | 90 |
| Day 5 pm | 4.51~7.5E6 | 0 | 0 | 120 |
| Day 6 | 7.51~12E6 | 0 | 0 | 120 |
| Day 7 | if <13E6 | 0 | 0 | 120 |
| | if >13.1E6 | 0 | 0 | 150 |

Pulse feeding

| Day | Pulse Feeding (mL) | | | | | |
|---|---|---|---|---|---|---|
| | TC Soy Plus (120 g/L) | LA/CD (1.5 mg/ml) | Lipid (500X) | TEC Solution | Immu Vitamin | BME/EDTA |
| Day 3 | 12.5 | 4 | 3 | — | — | 15 |
| Day 4 | 25 | 8 | — | — | — | — |
| Day 5 | 50 | 12 | — | 4 | 15 | 15 |
| Day 6 | 60 | 8 | 2 | 8 | — | — |
| Day 7 | 60 | — | 1 | — | — | — |
| Day 8 | 25 | | | | | |

TABLE 7

Process #2 for cell line 665.2B9.1E4

Continuous feeding

| Day | Expected Viable Cell Density (cells/mL) | Continuous Feeding Rate (ml/day) | | |
|---|---|---|---|---|
| | | Glucose and Glutamine | ImmuC2 | ImmuC5 |
| Day 2 | 0.4~0.7E6 | 60 | 0 | 0 |
| Day 3 am | 1.0~1.7E6 | 0 | 60 | 0 |
| Day 3 pm | 1.01~2.5E6 | 0 | 90 | 0 |
| Day 4 am | 2.51~3.5E6 | 0 | 90 | 0 |
| Day 4 pm | 2.51~4.5E6 | 0 | 150 | 0 |
| Day 5 am | 4.51~6.5E6 | 0 | 0 | 90 |
| Day 5 pm | 4.51~7.5E6 | 0 | 0 | 120 |
| Day 6 | 7.51~12E6 | 0 | 0 | 120 |
| Day 7 | if <13E6 | 0 | 0 | 120 |
| | if >13.1E6 | 0 | 0 | 150 |
| Day 8 | if <10E6 | 0 | 0 | 90 |
| | if 10.1~13E6 | 0 | 0 | 120 |
| | if >13.1E6 | 0 | 0 | 150 |

Pulse feeding

| Day | Pulse Feeding (mL) | | | | | | |
|---|---|---|---|---|---|---|---|
| | TC Soy Plus (120 g/L) | LA/CD (1.5 mg/ml) | Lipid (500X) | TEC Solution | Immu Vitamin | BME/EDTA | Insulin (4 mg/ml) |

TABLE 7-continued

Process #2 for cell line 665.2B9.1E4

| Day | | | | | | | |
|---|---|---|---|---|---|---|---|
| Day 3 | 12.5 | 2 | 3 | — | — | 15 | — |
| Day 4 | 25 | 4 | — | — | — | — | — |
| Day 5 | 50 | 6 | — | 4 | 15 | 15 | 4 |
| Day 6 | 60 | 4 | — | 8 | — | — | 8 |
| Day 7 | 60 | 4 | — | — | — | 15 | 8 |
| Day 8 | 50 | — | — | — | — | — | 8 |

TABLE 8

Process #1 for cell line 665.B4.1C1

Continuous feeding

| | | Continuous Feeding Rate (ml/day) | | |
|---|---|---|---|---|
| Day | Expected Viable Cell Density (cells/mL) | Glucose and Glutamine | ImmuC2 | ImmuC5 |
| Day 2 | 0.4~0.7E6 | 60 | 0 | 0 |
| Day 3 am | 1.0~1.7E6 | 0 | 90 | 0 |
| Day 3 pm | 1.01~2.5E6 | 0 | 120 | 0 |
| Day 4 am | 2.51~3.5E6 | 0 | 0 | 60 |
| Day 4 pm | 2.51~4.5E6 | 0 | 0 | 90 |
| Day 5 am | 4.51~6.5E6 | 0 | 0 | 120 |
| Day 5 pm | 4.51~7.5E6 | 0 | 0 | 150 |
| Day 6 | 7.51~12E6 | 0 | 0 | 180 |
| Day 7, 8, 9 | if <15E6 | 0 | 0 | 180 |
| | if >15.1E6 | 0 | 0 | 240 |
| Day 10 | if <10E6 | 0 | 0 | 120 |
| | if 10.1~13E6 | 0 | 0 | 150 |
| | if >13.1E6 | 0 | 0 | 180 |

Pulse feeding

| Day | TC Soy Plus (120 g/L) | LA/CD (1.5 mg/ml) | Lipid (500X) | TEC Solution | Immu Vitamin | BME/EDTA |
|---|---|---|---|---|---|---|
| Day 3 | 12.5 | 4 | 3 | — | — | 15 |
| Day 4 | 25 | 8 | — | — | — | — |
| Day 5 | 50 | 12 | — | 4 | 15 | 15 |
| Day 6 | 60 | 8 | 2 | 8 | — | — |
| Day 7 | 60 | — | 1 | — | — | 15 |
| Day 8 | 60 | — | — | — | — | — |
| Day 9 | 60 | — | — | — | — | 15 |
| Day 10 | 50 | — | — | — | — | — |

TABLE 9

Process #2 for cell line 665.B4.1C1

Continuous feeding

| | | Continuous Feeding Rate (ml/day) | | |
|---|---|---|---|---|
| Day | Expected Viable Cell Density (cells/mL) | Glucose and Glutamine | ImmuC2 | ImmuC5 |
| Day 2 | 0.4~0.7E6 | 60 | 0 | 0 |
| Day 3 am | 1.0~4.7E6 | 0 | 90 | 0 |
| Day 3 pm | 1.01~2.5E6 | 0 | 120 | 0 |
| Day 4 am | 2.51~3.5E6 | 0 | 0 | 60 |
| Day 4 pm | 2.51~4.5E6 | 0 | 0 | 90 |
| Day 5 am | 4.51~6.5B6 | 0 | 0 | 120 |
| Day 5 pm | 4.51~7.5E6 | 0 | 0 | 150 |
| Day 6 | 7.51~12E6 | 0 | 0 | 180 |
| Day 7, 8, 9 | if <15E6 | 0 | 0 | 180 |
| | if >15.1E6 | 0 | 0 | 240 |
| Day 10 | if <10E6 | 0 | 0 | 120 |
| | if 10.1~13E6 | 0 | 0 | 150 |
| | if >13.1E6 | 0 | 0 | 180 |

Pulse feeding

| Day | TC Soy Plus (120 g/L) | LA/CD (1.5 mg/ml) | Lipid (500X) | TEC Solution | Immu Vitamin | BME/EDTA | Insulin (4 mg/ml) |
|---|---|---|---|---|---|---|---|
| Day 3 | 12.5 | 2 | 3 | — | — | 15 | — |
| Day 4 | 25 | 4 | — | — | — | — | — |
| Day 5 | 50 | 6 | — | 4 | 15 | 15 | 4 |
| Day 6 | 60 | 4 | — | 8 | — | — | 8 |
| Day 7 | 60 | 4 | — | — | — | 15 | 8 |
| Day 8 | 60 | 4 | — | — | — | — | 8 |
| Day 9 | 60 | 4 | — | 4 | 15 | 15 | 8 |
| Day 10 | 60 | — | — | — | — | 1- | 8 |

During the cultivation, bioreactor samples were taken periodically for off-line analysis. The viable cell density (VCD) and the cell viability were measured by microscopic counting using a hemocytometer after staining with 0.4% trypan blue dye. The glucose, lactate, glutamine, ammonia concentrations were measured using a Nova Bioprofile 200. The antibody concentration was determined by HPLC using a protein A affinity chromatography column (Applied Biosystems, P/N 2-1001-00).

The specific antibody productivity was calculated by dividing the cumulative antibody produced by the time integral of the total viable cell in the culture:

$$Q_{[MAb]} = \frac{([Mab]_{t1} \cdot V_{t1} - [Mab]_{t0} \cdot V_{t0}}{\int_0^{t1} VCD \cdot V dt},$$

in which $\int_0^{t1} VCD \cdot V dt$ is approximated by the

Trapezium Rule: $\frac{(VCD_{t0} \cdot V_{t0} + VCD_{t1} \cdot V_{t1})(t1 - t0)}{2}$ By Process #1, 665.2B9.1E4 cells grew to attain a maximal VCD of $1 \times 10^7$ viable cells/ml on day 6 with 86% of viability. After day 6, VCD and V % decreased quickly and the culture was harvested on day 8. Process #2 helped the culture reach a higher VCD of $1.2 \times 10^7$ viable cells/ml and sustain one more day.

As compared to 665.2B9.1E4 cells, 665.B4.1C1 cells exhibited much better growth in both processes. In Process #1, its VCD reached $2 \times 10^7$ viable cells/ml on day 7 with 97% viability. The culture also maintained this VCD and V % for two more days before it started to decline. The culture was harvested on day 11. In Process #2, 665.B4.1C1 cells showed a similar growth profile as in Processes #1. More specifically, the cells reached the highest VCD of $2.3 \times 10^7$ viable cells/ml and the viability declined a little slower with the harvest occurring on day 11. This observation was somewhat different from the 665.2B9.1E4 cell line, which demonstrated a growth advantage in Process #2.

The antibody yields of two cell lines in Processes #1 and #2 were compared. The final yield of 665.2B9.1E4 cells was 0.42 g/L in Process #1 and 0.55 WL in Process #2. For comparison, 665.B4.1C1 cells delivered a higher final yield of 1.5 g/L in both processes.

The daily specific antibody productivities (per cell basis) were calculated and the 665.2B9.1E4 cells had an average daily $Q_{[mAb]}$ of approximately 15 pg/cell/day throughout the course of cultivation for both processes. The additional day of growth at the highest VCD in Process #2 resulted in a higher final antibody concentration.

The 665.B4.1C1 cells showed a similar daily specific antibody productivity profile in both processes with Process #1 yielding slightly higher productivity. The daily $Q_{[Mab]}$ were maintained between about 20 to 25 pg/cell/day until day 9. Thereafter the productivity declined.

Compared with the 665.2B9.1E4 cell line, the 665.B4.1C1 cell line exhibited a higher specific antibody productivity of about 25 pg/cell/day as compared to 15 pg/cell/day. Combining with its better growth, the 665.B4.1C1 cell line tripled the final antibody yield to 1.5 g/L as compared to 0.55 g/L achieved by the 665.2B9.1E4 cell line. These results demonstrate the benefit of incorporating Bcl-2 gene into the host cell line to enhance its growth and antibody yield in serum-free media in a bioreactor modeled for large-scale commercial preparation of a recombinant protein, in this case an antibody for clinical use.

Example 12

Development of Sp/ESF Serum Free Pre-Adapted Cell Line

A standard protocol for cell transformation and protein production is summarized as follows. Sp2/0 cells, or Sp2/0 derived lines are maintained in 10% FBS and transfected by electroporation with an expression vector containing the gene of interest. While maintaining the transfectant cell lines in media supplemented with 10% FBS, attempts are made to amplify the expression by step-wise increases in methotrexate (MTX) in the culture media. This amplification process, which only seems to work on occasion and typically with cell lines having lower initial productivity, usually takes 4-8 months. Once MTX amplification is completed, the clones are gradually adapted for growth in serum-free media over a period of 3-6 months, which typically results in a loss of productivity of up to 50%.

Since the Sp/EEE cell line showed enhanced growth and survival properties as well as superior tolerance to serum deprivation, it was decided to explore the feasibility of developing an Sp/EEE cell line that is pre-adapted to growth in serum-free media and use this line for transfection, cloning and amplification. The following describes the development of the Sp/ESF (Sp/EEE serum-free) cell line. Feasibility for production of cloned proteins, such as antibodies or fragments, was demonstrated by transfection with the C-AD2-Fab-h679-pdHL2 expression vector.

Adaptation to Growth in Serum Free Media and Subcloning

Sp/EEE cells were adapted to growth in serum-free media (SFM) over a 2-month period. In an attempt to determine if transfection is feasible in SFM without FBS, serum free-adapted Sp/EEE cells were plated in a limiting dilution to determine if they would recover from low density. Cells were plated at a concentration of 5 cells/well in the first row of a 96-well plate and diluted 2-fold down the plate. Seven clones total resulted from the limiting dilution. These results demonstrate that the cells can survive under the conditions necessary for transfection. Growth curve experiments were performed using four of the seven subclones to select the clone with the most favorable growth properties. The four clones (#1, 3, 4, and 5), as well as the parental clone, were split to a density of $3 \times 10^5$ cells/ml in a T25 flask in 6 ml of culture media. The cell viability (FIG. 25) and density (FIG. 26) were monitored until zero viability was reached.

Of the subclones, #3 survived 24 hours longer than any other subclone or the parental cell line. In addition, subclones #3 and #1 reached higher maximal cell density (3.2 to 3.3 million/mL, FIG. 26) than the other clones. This suggests that subclone #3 may be better adapted to undergo successful transfection. Therefore, subclone #3 was given a new designation of Sp/ESF and used for subsequent transfections.

Transfection of Sp/ESF Cells with h679-AD2

Based on the above data Sp/ESF cells (subclone #3) were transfected by electroporation with 30 µg of h679-AD2-pdHL2 following standard protocol for Sp2/0 cells. After 48 hours cells were selected with 0.1 µM MTX. As a control Sp/EEE cells in 10% FBS were also transfected with h679-AD2-pdHL2 by electroporation under the same conditions. After 10 days plates were ready for screening via ELISA using BSA-IMP-260 coated plates. For both transfections approximately 130 of 400 wells contained positive clones. Positive Sp/ESF cells from wells with the 40 highest OD readings were transferred to 24-well plates and the MTX was increased to 0.2 µM MTX. After the cells in the 24-well plates reached terminal, further screening by BIACORE analysis using an HSG sensorchip was performed. Four of the screened clones had a productivity of >50 mg/L. The highest producing clone (h679-AD2-SF #T6) had an initial productivity of 82 mg/L. These initial productivity results were very similar to those obtained from a previous transfection of this construct using Sp/EEE cells in 10% FBS.

Amplification

The h679-AD2-SF#T6 clone was selected for MTX amplification. After 2 weeks the MTX concentration was increased from 0.2 µM to 0.4 µM. After only 2 MTX increases, some amplification in productivity can already be observed.

TABLE 10

| MTX Concentration | Productivity |
|---|---|
| 0.1 µM MTX | 82 mg/L |
| 0.2 µM MTX | 93 mg/L |
| 0.4 µM MTX | 103 mg/L |

CONCLUSIONS

The data presented above for Sp/ESF indicate that transfection, cloning by limiting dilution and MTX amplification can all be accomplished under serum-free conditions in less than a month. This was demonstrated with the transfection of the h679-Fab-AD2-pdHL2 expression vector, resulting in the initial very high production of 82 mg/L, which could be amplified to 103 mg/L in two weeks. Further amplification is expected with a longer time of MTX exposure. The initial productivity of the best clone (T6) of 82 mg/L surpasses the initial productivity of the best h679-AD2-pdHL2 clone (5D8) from the original transfection of the parent Sp/EEE cell line carried out in 10% FBS, which was around 50 mg/L. Sp/ESF cells have also been transfected with EPO-DDD2-pdHL2 for production of erythropoietin.

As shown in Table 11, which compares the key parameters of Sp/ESF with those of the existing PER.C6 cell line (Jones et al in Biotechnol. Prog. 2003, 19: 163-168), Sp/ESP excels PER.C6 in many categories.

TABLE 11

|  |  | Sp/ESP | PER.C6 |
|---|---|---|---|
| Parental Cell line |  | Mouse myeloma | Human embryonic retina + E1 |
| Anti-apoptotic gene |  | Bcl-2-EEE | None |
| Transfection | Method | Electroporation | Lipofectamine |
|  | Efficiency | 130/400 | ? |
|  | Growth | Suspension | Adherent |
|  | Medium | SFM | 10% FBS |
| Screening | Growth Medium | Suspension SFM | Adherent 10% FBS |

TABLE 11-continued

|  |  | Sp/ESP | PER.C6 |
|---|---|---|---|
| Selected clones | Growth | Suspension | Suspension |
|  | Medium | SFM | SFM |
|  | Adaption time | None | 4 weeks |
| Doubling time |  | ~12 h | 30-33 h |
| Cell culture | Vessel | T-25 | Roller bottle |
|  | Medium | SFM | SFM |
|  | Maximal density | $3.3 \times 10^6$/mL | $5 \times 10^6$/mL |
|  | Productivity | 103 mg/L of Fab* | 300-500 mg/L of IgG |

*Equivalent to 300 mg/L of IgG

What is claimed is:

1. A method of producing a mammalian cell line that is pre-adapted for growth and transfection in serum-free medium comprising:
   a) transfecting a mammalian cell line with a first nucleic acid encoding a mutant Bcl-2 protein comprising T69E, S70E and S87E amino acid substitutions, to produce a Bcl-EEE host cell;
   b) culturing the Bcl-EEE host cell in the presence of methotrexate to amplify the first nucleic acid; and
   c) adapting the Bcl-EEE host cell to grow in serum-free medium to produce a pre-adapted Bcl-EEE host cell, wherein the pre-adapted Bcl-EEE host cell can be transfected in serum-free medium with a second nucleic acid encoding a recombinant protein.

2. The method of claim 1, further comprising transfecting the pre-adapted Bcl-EEE host cell in serum-free medium with a second nucleic acid encoding a recombinant protein to produce a recombinant pre-adapted Bcl-EEE host cell.

3. The method of claim 2, further comprising culturing the recombinant pre-adapted Bcl-EEE host cell in culture medium to produce the recombinant protein.

4. The method of claim 3, further comprising culturing the recombinant pre-adapted Bcl-EEE host cell in the presence of methotrexate to amplify the second nucleic acid.

5. The method of claim 1, further comprising storing the pre-adapted Bcl-EEE host cell frozen in serum-free medium before transfecting it with a second nucleic acid.

6. The method of claim 5, wherein the pre-adapted Bcl-EEE host cell can be transfected with said second nucleic acid in serum-free medium after said pre-adapted Bcl-EEE host cell is frozen and thawed.

7. The method according to claim 2, wherein said recombinant pre-adapted Bcl-EEE host cell can be cultured in serum-free medium to produce said recombinant protein.

8. The method according to claim 6, wherein said recombinant pre-adapted Bcl-EEE host cell can be cultured in serum-free medium without further adaptation to serum-free growth.

9. The method of claim 2, wherein the recombinant protein is an antibody, an antibody fragment, a growth factor, a protein or peptide hormone, an interleukin, an interferon or an enzyme.

10. The method of claim 9, wherein the protein is selected from the group consisting of EPO, G-CSF, GM-CSF, EGF, VEGF, thrombopoietin, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, interferon-α, interferon-β, and interferon-γ and interferon-λ.

11. The method of claim 3, wherein the medium further comprises at least one caspase inhibitor.

12. The method of claim 11, wherein said caspase inhibitor is selected from the group consisting of caspase-1, caspase-3, caspase-9, caspase-12 and pan-caspase inhibitors.

13. The method of claim 11, wherein said caspase inhibitor is selected from the group consisting of Z-VAD-fmk, Ac-DEVD-cho (SEQ ID NO: 7), Aven and XIAP.

14. The method of claim 3, wherein said medium further comprises at least one growth factor, cytokine or hormone.

15. The method of claim 14, wherein the growth factor, cytokine or hormone is selected from the group consisting of erythropoietin, thrombopoietin, IL-2, IL-3, IL-4, IL-5, IL-6, IL-9, IL-11, IL-12, IL-13, IL-15, prolactin, growth hormone, G-CSF and GM-CSF.

16. The method of claim 1, wherein the cell line is a myeloma cell line selected from the group consisting of Sp2/0, an Sp2/0 derivative, NSO or YB2/0.

17. The method of claim 1, wherein the cell line is selected from the group consisting of CHO, HEK 293, COS-1, COS-7, HepG2, BHK21, P3X3Ag8.653 and BSC-1.

* * * * *

SEQUENCE LISTING

```
<160> NUMBER OF SEQ ID NOS: 11

<210> SEQ ID NO 1
<211> LENGTH: 9780
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 1
ttccataggc tccgccccc tgacgagcat cacaaaaatc gacgctcaag tcagaggtgg      60
cgaaacccga caggactata aagataccag gcgtttcccc ctggaagctc cctcgtgcgc     120
tctcctgttc cgaccctgcc gcttaccgga tacctgtccg cctttctccc ttcgggaagc     180
gtggcgcttt ctcatagctc acgctgtagg tatctcagtt cggtgtaggt cgttcgctcc     240
aagctgggct gtgtgcacga accccccgtt cagcccgacc gctgcgcctt atccggtaac     300
tatcgtcttg agtccaaccc ggtaagacac gacttatcgc cactggcagc agccactggt     360
aacaggatta gcagagcgag gtatgtaggc ggtgctacag agttcttgaa gtggtggcct     420
aactacggct acactagaag gacagtattt ggtatctgcg ctctgctgaa gccagttacc     480
ttcggaaaaa gagttggtag ctcttgatcc ggcaaacaaa ccaccgctgg tagcggtggt     540 tttttttgttt gcaagcagca gattacgcgc agaaaaaaag gatctcaaga agatcctttg     600
atcttttcta cggggtctga cgctcagtgg aacgaaaact cacgttaagg gattttggtc     660
atgagattat caaaaaggat cttcacctag atccttttaa attaaaaatg aagttttaaa     720
tcaatctaaa gtatatatga gtaaacttgg tctgacagtt accaatgctt aatcagtgag     780
gcacctatct cagcgatctg tctatttcgt tcatccatag ttgcctgact ccccgtcgtg     840
tagataacta cgatacggga gggcttacca tctggcccca gtgctgcaat gataccgcga     900
gacccacgct caccggctcc agatttatca gcaataaacc agccagccgg aagggccgag     960
cgcagaagtg gtcctgcaac tttatccgcc tccatccagt ctattaattg ttgccgggaa    1020
gctagagtaa gtagttcgcc agttaatagt ttgcgcaacg ttgttgccat tgctgcaggc    1080
atcgtggtgt cacgctcgtc gtttggtatg gcttcattca gctccggttc ccaacgatca    1140
aggcgagtta catgatcccc catgttgtgc aaaaaagcgg ttagctcctt cggtcctccg    1200
atcgttgtca gaagtaagtt ggccgcagtg ttatcactca tggttatggc agcactgcat    1260
aattctctta ctgtcatgcc atccgtaaga tgcttttctg tgactggtga gtactcaacc    1320
aagtcattct gagaatagtg tatgcggcga ccgagttgct cttgcccggc gtcaacacgg    1380
gataataccg cgccacatag cagaacttta aaagtgctca tcattggaaa acgttcttcg    1440
```

```
gggcgaaaac tctcaaggat cttaccgctg ttgagatcca gttcgatgta acccactcgt    1500
gcacccaact gatcttcagc atctttttact ttcaccagcg tttctgggtg agcaaaaaca   1560
ggaaggcaaa atgccgcaaa aagggaata agggcgacac ggaaatgttg aatactcata    1620
ctcttccttt ttcaatatta ttgaagcatt tatcagggtt attgtctcat gagcggatac   1680
atatttgaat gtatttagaa aaataaacaa ataggggttc cgcgcacatt tccccgaaaa   1740
ggccacctga cgtctaagaa accattatta tcatgacatt aacctataaa aataggcgta   1800
tcacgaggcc ctttcgtctt caagaattcc gatccagaca tgataagata cattgatgag   1860
tttggacaaa ccacaactag aatgcagtga aaaaaatgct ttatttgtga aatttgtgat   1920
gctattgctt tatttgtaac cattataagc tgcaataaac aagttaacaa caacaattgc   1980
attcatttta tgtttcaggt tcaggggggag gtgtgggagg ttttttaaag caagtaaaac    2040
ctctacaaat gtggtatggc tgattatgat ctaaagccag caaaagtccc atggtcttat   2100
aaaaatgcat agctttagga ggggagcaga gaacttgaaa gcatcttcct gttagtcttt   2160
cttctcgtag acttcaaact tatacttgat gccttttttcc tcctggacct cagagaggac   2220
gcctgggtat tctgggagaa gtttatattt ccccaaatca atttctggga aaaacgtgtc   2280
actttcaaat tcctgcatga tccttgtcac aaagagtctg aggtggcctg gttgattcat   2340
ggcttcctgg taaacagaac tgcctccgac tatccaaacc atgtctactt tacttgccaa   2400
ttccggttgt tcaataagtc ttaaggcatc atccaaactt ttggcaagaa aatgagctcc   2460
tcgtggtggt tctttgagtt ctctactgag aactatatta attctgtcct ttaaaggtcg   2520
attcttctca ggaatggaga accaggtttt cctacccata atcaccagat tctgtttacc   2580
ttccactgaa gaggttgtgg tcattctttg gaagtacttg aactcgttcc tgagcggagg   2640
ccagggtcgg tctccgttct tgccaatccc catattttgg gacacggcga cgatgcagtt   2700
caatggtcga accatgaggg caccaagcta gcttttttgca aaagcctagg cctccaaaaa   2760
agcctcctca ctacttctgg aatagctcag aggccgaggc ggcctcggcc tctgcataaa   2820
taaaaaaaat tagtcagcca tggggcgag aatgggcgga actgggcgga gttaggggcg   2880
ggatgggcgg agttaggggc gggactatgg ttgctgacta attgagatgc atgctttgca   2940
tacttctgcc tgctggggag cctggggact ttccacacct ggttgctgac taattgagat   3000
gcatgctttg catacttctg cctgctgggg agcctgggga ctttccacac cctaactgac   3060
acacattcca cagtcgacta gaatatggat agtgggtgtt tatgactctg gataagcctg   3120
aacaattgat gattaatgcc cctgagctct gttcttagta acatgtgaac atttacttgt   3180
gtcagtgtag tagatttcac atgacatctt ataataaacc tgtaaatgaa agtaatttgc   3240
attactagcc cagcccagcc catactaaga gttatattat gtctgtctca cagcctgctg   3300
ctgaccaata ttgaaaagaa tagaccttcg actggcagga agcaggtcat gtggcaaggc   3360
tatttgggga agggaaaata aaaccactag gtaaacttgt agctgtggtt tgaagaagtg   3420
gttttgaaac actctgtcca gccccaccaa accgaaagtc caggctgagc aaaacaccac   3480
ctgggtaatt tgcatttcta aaataagttg aggattcagc cgaaactgga gaggtcctct   3540
tttaacttat tgagttcaac cttttaattt tagcttgagt agttctagtt tccccaaact   3600
taagtttatc gacttctaaa atgtatttag aattcgacc aattctcatg tttgacagct   3660
tatcatcgct gcactccgcc cgaaaagtgc gctcggctct gccaaggacg cggggcgcgt   3720
gactatgcgt gggctggagc aaccgcctgc tgggtgcaaa ccctttgcgc ccggactcgt   3780
ccaacgacta taagagggc aggctgtcct ctaagcgtca ccacgacttc aacgtcctga   3840
```

```
gtaccttctc ctcacttact ccgtagctcc agcttcacca gatccctcga ctctagaggc    3900
cttaagggcc ttactgagca cacaggacct caccatggga tggagctgta tcatcctctt    3960
cttggtagca acagctacag gtaaggggct cacagtagca ggcttgaggt ctggacatat    4020
atatgggtga caatgacatc cactttgcct ttctctccac aggtgtccac tccgacatcc    4080
agctgaccca gagcccaagc agcctgagcg ccagcgtggg tgacagagtg accatcacct    4140
gtaaggccag tcaggatgtg ggtacttctg tagcctggta ccagcagaag ccaggtaagg    4200
ctccaaagct gctgatctac tggacatcca cccggcacac tggtgtgcca agcagattca    4260
gcggtagcgg tagcggtacc gacttcacct tcaccatcag cagcctccag ccagaggaca    4320
tcgccaccta ctactgccag caatatagcc tctatcggtc gttcggccaa gggaccaagg    4380
tggaaatcaa acgtgagtag aatttaaact ttgcttcctc agttggatcc cgcaattcta    4440
aactctgagg gggtcggatg acgtggccat tctttgccta aagcattgag tttactgcaa    4500
ggtcagaaaa gcatgcaaag ccctcagaat ggctgcaaag agctccaaca aaacaattta    4560
gaactttatt aaggaatagg gggaagctag gaagaaactc aaaacatcaa gattttaaat    4620
acgcttcttg gtctccttgc tataattatc tgggataagc atgctgtttt ctgtctgtcc    4680
ctaacatgcc ctgtgattat ccgcaaacaa cacacccaag ggcagaactt gttacttaa    4740 acaccatcct gtttgcttct ttcctcagga actgtggctg caccatctgt cttcatcttc    4800
ccgccatctg atgagcagtt gaaatctgga actgcctctg ttgtgtgcct gctgaataac    4860
ttctatccca gagaggccaa agtacagtgg aaggtggata cgccctcca atcgggtaac    4920 tcccaggaga gtgtcacaga gcaggacagc aaggacagca cctacagcct cagcagcacc    4980
ctgacgctga gcaaagcaga ctacgagaaa cacaaagtct acgcctgcga agtcaccat    5040 cagggcctga gctcgcccgt cacaaagagc ttcaacaggg gagagtgtta gagggagaag    5100
tgcccccacc tgctcctcag ttccagcctg accccctccc atcctttggc ctctgaccct    5160
ttttccacag gggacctacc cctattgcgg tcctccagct catctttcac ctcaccccc    5220 tcctcctcct tggctttaat tatgctaatg ttggaggaga atgaataaat aaagtgaatc    5280
tttgcacctg tggtttctct ctttcctcat ttaataatta ttatctgttg ttttaccaac    5340
tactcaattt ctcttataag ggactaaata tgtagtcatc ctaaggcgca taaccattta    5400
taaaaatcat ccttcattct attttaccct atcatcctct gcaagacagt cctccctcaa    5460
acccacaagc cttctgtcct cacagtcccc tgggccatgg taggagagac ttgcttcctt    5520
gttttcccct cctcagcaag ccctcatagt ccttttttaag ggtgacaggt cttacagtca    5580
tatatccttt gattcaattc cctgagaatc aaccaaagca aatttttcaa agaagaaac    5640 ctgctataaa gagaatcatt cattgcaaca tgatataaaa taacaacaca ataaaagcaa    5700
ttaaataaac aaacaatagg gaaatgttta agttcatcat ggtacttaga cttaatggaa    5760
tgtcatgcct tatttacatt tttaaacagg tactgaggga ctcctgtctg ccaagggccg    5820
tattgagtac tttccacaac ctaatttaat ccacactata ctgtgagatt aaaaacattc    5880
attaaaatgt tgcaaaggtt ctataaagct gagagacaaa tatattctat aactcagcaa    5940
ttcccacttc taggggttcg actggcagga agcaggtcat gtggcaaggc tatttgggga    6000
agggaaaata aaaccactag gtaaacttgt agctgtggtt tgaagaagtg gttttgaaac    6060
actctgtcca gccccaccaa accgaaagtc caggctgagc aaaacaccac ctgggtaatt    6120
tgcatttcta aaataagttg aggattcagc cgaaactgga gaggtcctct tttaacttat    6180
tgagttcaac cttttaattt tagcttgagt agttctagtt tccccaaact taagtttatc    6240
```

```
gacttctaaa atgtatttag aatttcgacc aattctcatg tttgacagct tatcatcgct    6300
gcactccgcc cgaaaagtgc gctcggctct gccaaggacg cggggcgcgt gactatgcgt    6360
gggctggagc aaccgcctgc tgggtgcaaa ccctttgcgc ccggactcgt ccaacgacta    6420
taaagagggc aggctgtcct ctaagcgtca ccacgacttc aacgtcctga gtaccttctc    6480
ctcacttact ccgtagctcc agcttcacca gatccctcga gcacacagga cctcaccatg    6540
ggatggagct gtatcatcct cttcttggta gcaacagcta caggtaaggg gctcacagta    6600
gcaggcttga ggtctggaca tatatatggg tgacaatgac atccactttg cctttctctc    6660
cacaggtgtc cactcccagg tccaactgca ggagagcggt ggaggtgttg tgcaacctgg    6720
ccggtccctg cgcctgtcct gctccgcatc tggcttcgat ttcaccacat attggatgag    6780
ttgggtgcga caggcacctg gaaaaggtct tgagtggatt ggagaaattc atccagatag    6840
cagtacgatt aactatgcgc cgtcgctaaa agatagattt acaatatcgc gagacaacgc    6900
caagaacaca ttgttcctgc aaatggacag cctgagaccc gaagacaccg ggtctatttt    6960
ttgtgcaagc ctttacttcg gcttcccctg gtttgcttat tggggccaag ggaccccggt    7020
caccgtctcc tcaggtgagt ccttacaacc tctctcttct attcagctta aatagatttt    7080
actgcatttg ttgggggga atgtgtgta tctgaatttc aggtcatgaa ggactaggga    7140 cccttggga gtcagaaagg gtcattggga gccccaagct ttctggggca ggccaggcct    7200
gaccttggct ttggggcagg gaggggggcta aggtgaggca ggtggcgcca gccaggtgca    7260
cacccaatgc ccatgagccc agacactgga cgctgaacct cgcggacagt taagaaccca    7320
ggggcctctg cgccctgggc ccagctctgt cccacaccgc ggtcacatgg caccacctct    7380
cttgcagcct ccaccaaggg cccatcggtc ttcccctgg cacctcctc caagagcacc    7440 tctggggca cagcggccct gggctgcctg gtcaaggact acttccccga accggtgacg    7500
gtgtcgtgga actcaggcgc cctgaccagc ggcgtgcaca ccttcccggc tgtcctacag    7560
tcctcaggac tctactccct cagcagcgtg gtgaccgtgc cctccagcag cttgggcacc    7620
cagacctaca tctgcaacgt gaatcacaag cccagcaaca ccaaggtgga caagagagtt    7680
ggtgagaggc cagcacaggg agggagggtg tctgctggaa gccaggctca gcgctcctgc    7740
ctggacgcat cccggctatg cagccccagt ccagggcagc aaggcaggcc ccgtctgcct    7800
cttcacccgg agcctctgcc cgccccactc atgctcaggg agagggtctt ctggctttt    7860 cccaggctct gggcaggcac aggctaggtg cccctaaccc aggccctgca cacaaagggg    7920
caggtgctgg gctcagacct gccaagagcc atatccggga ggaccctgcc cctgacctaa    7980
gcccacccca aaggccaaac tctccactcc ctcagctcgg acaccttctc tcctcccaga    8040
ttccagtaac tcccaatctt ctctctgcag agcccaaatc ttgtgacaaa actcacacat    8100
gcccaccgtg cccaggtaag ccagcccagg cctcgccctc cagctcaagg cgggacaggt    8160
gccctagagt agcctgcatc cagggacagg ccccagccgg gtgctgacac gtccacctcc    8220
atctcttcct cagcacctga actcctgggg ggaccgtcag tcttcctctt ccccccaaaa    8280
cccaaggaca ccctcatgat ctcccggacc cctgaggtca catgcgtggt ggtggacgtg    8340
agccacgaag accctgaggt caagttcaac tggtacgtgg acggcgtgga ggtgcataat    8400
gccaagacaa agccgcggga ggagcagtac aacagcacgt accgggtggt cagcgtcctc    8460
accgtcctgc accaggactg gctgaatggc aaggagtaca gtgcaaggt ctccaacaaa    8520 gccctcccag cccccatcga gaaaaccatc tccaaagcca aggtgggac ccgtggggtg    8580 cgagggccac atggacagag gccggctcgg cccaccctct gccctgagag tgaccgctgt    8640
```

```
accaacctct gtcctacagg gcagccccga gaaccacagg tgtacaccct gcccccatcc    8700
cgggaggaga tgaccaagaa ccaggtcagc ctgacctgcc tggtcaaagg cttctatccc    8760
agcgacatcg ccgtggagtg ggagagcaat gggcagccgg agaacaacta caagaccacg    8820
cctcccgtgc tggactccga cggctccttc ttcctctata gcaagctcac cgtggacaag    8880
agcaggtggc agcaggggaa cgtcttctca tgctccgtga tgcatgaggc tctgcacaac    8940
cactacacgc agaagagcct ctccctgtct ccgggtaaat gagtgcgacg gccggcaagc    9000
ccccgctccc cgggctctcg cggtcgcacg aggatgcttg gcacgtaccc cgtctacata    9060
cttcccaggc acccagcatg gaaataaagc acccaccact gccctgggcc cctgcgagac    9120
tgtgatggtt ctttccacgg gtcaggccga gtctgaggcc tgagtggcat gagggaggca    9180
gagcgggtcc cactgtcccc cactggcccc aggctgtgca ggtgtgcctg ggccgcctag    9240
ggtggggctc agccagggc tgccctcggc agggtggggg atttgccagc gtggccctcc    9300
ctccagcagc agctgcctcg cgcgtttcgg tgatgacggt gaaaacctct gacacatgca    9360
gctcccggag acggtcacag cttgtctgta agcggatgcc gggagcagac aagcccgtca    9420
gggcgcgtca gcgggtgttg gcgggtgtcg gggcgcagcc atgacccagt cacgtagcga    9480
tagcggagtg tatactggct taactatgcg gcatcagagc agattgtact gagagtgcac    9540
catatgcggt gtgaaatacc gcacagatgc gtaaggagaa ataccgcat caggcgctct    9600 tccgcttcct cgctcactga ctcgctgcgc tcggtcgttc ggctgcggcg agcggtatca    9660
gctcactcaa aggcggtaat acggttatcc acagaatcag gggataacgc aggaaagaac    9720
atgtgagcaa aaggccagca aaaggccagg aaccgtaaaa aggccgcgtt gctggcgttt    9780
```

<210> SEQ ID NO 2
<211> LENGTH: 420
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 2

```
caatggtcga accatgaggg caccaagcta gcttttttgca aaagcctagg cctccaaaaa      60
agcctcctca ctacttctgg aatagctcag aggccgaggc ggcctcggcc tctgcataaa     120 taaaaaaat tagtcagcca tggggcggag aatgggcgga actgggcgga gttaggggcg     180
ggatgggcgg agttagggc gggactatgg ttgctgacta attgagatgc atgctttgca     240
tacttctgcc tgctggggag cctggggact ttccacacct ggttgctgac taattgagat    300
gcatgctttg catacttctg cctgctgggg agcctgggga cttccacac cctaactgac     360 acacattcca cagtcgacta gaatatggat agtgggtgtt tatgactctg ataagcctg     420
```

<210> SEQ ID NO 3
<211> LENGTH: 720
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 3

```
atggcgcacg ctgggagaac ggggtacgat aaccgggaga tagtgatgaa gtacatccat      60
tataagctgt cgcagagggg ctacgagtgg gatgcgggag atgtgggcgc cgcgcccccg     120
ggggccgccc ccgcaccggg catcttctcc tcccagcccg gcacacgcc ccatccagcc      180
```

```
gcatcccgcg accggtcgc cagagaagaa ccgctgcaga ctccggctgc tcctggagca    240
gctgcaggac ctgcgctcga accggtgcca cctgtggtcc acctgaccct ccgccaggcc    300
ggcgacgact tctcccgccg ctaccgccgc gacttcgccg agatgtccag ccagctgcac    360
ctgacgccct tcaccgcgcg gggacgcttt gccacggtgg tggaggagct cttcagggac    420
ggggtgaact gggggaggat tgtggccttc tttgagttcg gtgggtcat gtgtgtggag    480 agcgtcaacc gggagatgtc gcccctggtg acaacatcg ccctgtggat gactgagtac    540
ctgaaccggc acctgcacac ctggatccag gataacggag gctgggatgc ctttgtggaa    600
ctgtacggcc ccagcatgcg gcctctgttt gatttctcct ggctgtctct gaagactctg    660
ctcagtttgg ccctggtggg agcttgcatc accctgggtg cctatctggg ccacaagtga    720
```

```
<210> SEQ ID NO 4
<211> LENGTH: 239
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 4
```

```
Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
             20                  25                  30

Gly Asp Val Gly Ala Ala Pro Pro Gly Ala Ala Pro Ala Pro Gly Ile
         35                  40                  45

Phe Ser Ser Gln Pro Gly His Thr Pro His Pro Ala Ala Ser Arg Asp
     50                  55                  60

Pro Val Ala Arg Glu Glu Pro Leu Gln Thr Pro Ala Ala Pro Gly Ala
 65                  70                  75                  80

Ala Ala Gly Pro Ala Leu Glu Pro Val Pro Pro Val Val His Leu Thr
                 85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235
```

```
<210> SEQ ID NO 5
<211> LENGTH: 80
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 5
ggacccggtc gccagagaag aaccgctgca gactccggct gctcctggag cagctgcagg    60
acctgcgctc gaaccggtgc                                                80

<210> SEQ ID NO 6
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgccggcctg gcggagggtc aggtggacca caggtggcac cggttcgagc gcaggtcctg    60
cagctgctcc aggagcagcc                                                80

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Glu Val Asp
  1

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atgtttcagg acccacagga gcga                                           24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttatggtttc tgagaacaga tggg                                           24

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tatatggacc cggtcgccag agaag                                          25

<210> SEQ ID NO 11
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttaatcgccg gcctggcgga gggtc                                         25
```